(12) United States Patent
Liu et al.

(10) Patent No.: US 7,592,315 B2
(45) Date of Patent: Sep. 22, 2009

(54) PEPTIDE VIRAL ENTRY INHIBITORS

(75) Inventors: Rong Liu, Scotch Plains, NJ (US); Rumin Zhang, Edison, NJ (US); Rong Kong, Scotch Plains, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/264,509

(22) Filed: Nov. 1, 2005

(65) Prior Publication Data

US 2006/0100148 A1    May 11, 2006

Related U.S. Application Data

(60) Provisional application No. 60/624,204, filed on Nov. 2, 2004.

(51) Int. Cl.
*A01N 37/18* (2006.01)
*A61K 38/16* (2006.01)
*A61K 38/21* (2006.01)
*A61K 39/42* (2006.01)
*G01N 33/00* (2006.01)

(52) U.S. Cl. ............... 514/13; 514/8; 514/11; 514/5; 514/6; 514/9; 514/7; 436/87; 530/317; 530/326; 435/69.1

(58) Field of Classification Search ....... None
See application file for complete search history.

(56) References Cited

U.S. PATENT DOCUMENTS 6,692,908 B1   2/2004   Foung et al.

FOREIGN PATENT DOCUMENTS

WO   WO2004/044220   5/2004

OTHER PUBLICATIONS

Tan et al. (1999) Proc. Natl. Acad. Sci. USA, vol. 96, p. 5533-5538.*
Brass et al. (2002) The Journal of Biological Chemistry, vol. 277, p. 8130-8139.*
Wang et al. (2002) Advanced Drug Delivery Review, vol. 54, p. 547-570.*
Ouzounov et al. (2002) Antiviral Research, vol. 55, p. 425-435.*
Martin et al. (1999) Protein Engineering, vol. 12, p. 1005-1011.*
Uno-Furuta et al. (2003) Vaccine, vol. 21, p. 3149-3156.*
Hsu et al., Hepatitis C virus glycoproteins mediate pH-dependent cell entry of pseudotyped retroviral particles, *Proc Natl Acad Sci U S A*. Jun. 10, 2003;100(12):7271-6. Epub May 21, 2003.
Bartosch et al., Infectious hepatitis C virus pseudo-particles containing functional E1-E2 envelope protein complexes, *J Exp Med*. Mar. 3, 2003;197(5):633-42.
Baldwin et al., Inhibiting HIV-1 entry with fusion inhibitors, *Curr Med Chem*. Sep. 2003;10(17):1633-42.
Vancompernolle et al., Small molecule inhibition of hepatitis C virus E2 binding to CD81, *Virology*. Sep. 15, 2003;314(1):371-80.
Sequence Disclosure under Accession No. NP_751920, (1997).
Sequence Disclosure under Accession No. NP_751921, (1997).
Sequence Disclosure under Accession No. AAB67038, (1997).
Sequence Disclosure under Accession No. AAB67036, (1997).
Sequence Disclosure under Accession No. P27958, (1991).
Sequence Disclosure under Accession No. NP_671491, (2002).
Sequence Disclosure under Accession No. AAG02099, (2000).
Sequence Disclosure under Accession No. AAB67037, (1997).
Sequence Disclosure under Accession No. AAP69952, (2005).
Sequence Disclosure under Accession No. NM_004356, (1990-2005).
Genbank Sequence Disclosure Accession No. AB049088; pp. 1-5, ( 2001 ).
Sarrazin et al., "Quasispecies heterogeneity of the carboxy-terminal part of the E2 gene including the PePHD and sensitivity of hepatitis C virus 1b isolates to antiviral therapy". Virology. Oct. 10, 2001; 289(1):150-163.
Takahashi et al., "Hepatitis C virus (HCV) genotype 1b sequences from fifteen patients with hepatocellular carcinoma; the 'progression score' revisited". Hepatology Res. Jun. 2001; 20(2):161-171.

* cited by examiner

*Primary Examiner*—Rebecca E Prouty
*Assistant Examiner*—Alexander D Kim

(57) ABSTRACT

The present invention provides, inter alia, peptide compositions and methods for treating and preventing Flaviviridae virus (e.g., hepatitis C virus) infections.

38 Claims, No Drawings

US 7,592,315 B2

PEPTIDE VIRAL ENTRY INHIBITORS

This application claims the benefit of U.S. provisional patent application No. 60/624,204, filed Nov. 2, 2004 which is herein incorporated by reference in its entirety.

FIELD OF THE INVENTION

The present invention comprises compositions and methods for treating or preventing a viral infection in subject.

BACKGROUND OF THE INVENTION

Approximately 170 million people are infected with hepatitis C virus (HCV) world-wide. Current therapies are helpful, but are not effective in every patient. Moreover, many of the current therapies result in unwanted side-effects.

HCV particles attach and enter target cells through interactions between their viral glycoproteins E1 and E2 and cell surface receptor molecules. The viral entry step has been difficult to study because there is no reliable, easy to detect system for performing HCV/tissue culture infection. Hsu et al. (Proc. Natl. Acad. Sci. USA. 100(12):7271-7276 (2003)) and Bartosch et al. (J. Exp. Med. 197(5):633-42 (2003)) reported the generation of HCV pseudoparticles that use the core proteins of HIV-1 and authentic HCV E1 and E2 proteins. The pseudoparticles specifically infect hepatocytes and liver-derived cell lines. Such pseudoparticle infection can be neutralized by HCV patient serum as well as antibodies against E1 and E2 glycoproteins. CD81 is a host cell protein required, but not sufficient, for HCV pseudoparticle entry.

Peptides derived from HIV-1 envelope glycoproteins can bind HIV-1 and inhibit infection at the cell fusion step (Baldwin et al., Curr. Med. Chem. 10(17): 1633-1642 (2003)). Foung et al. (U.S. Pat. No. 6,692,908) discuss use of antibodies which inhibit HCV E1 and E1 binding to CD81 for treatment of HCV infection. Garry et al. (WO 2004/044220) discuss use of the peptides from the E1 envelope glycoprotein of hepaciviruses and E2 envelope glycoprotein of pestiviruses for treatment of viral infection. Furthermore, VanCompernolle et al. disclose imidazole-based small molecules that inhibit E2/CD81 binding (Virology 314(1):371-380 (2003)).

As mentioned above, in spite of the current availability of treatments for HCV, infections in many patients are not responsive. There remains a need in the art for additional treatments to the prevention and treatment of HCV infection.

SUMMARY OF THE INVENTION

The present invention, inter alia, meets the need in the art for additional therapies for the treatment and prevention of HCV infection.

The present invention provides an isolated polypeptide comprising or consisting of an amino acid sequence selected from the group consisting of SEQ ID NOs: 3-139. In an embodiment of the invention, the polypeptide comprises or consists of the amino acid sequence of SEQ ID NO: 3, 7, 9, 10, 12-28, 30-38, 40, 42, 44-60, 62-68, 70, 71, 73-103, 106-120, 121-130, 132-138.

Another embodiment of the invention comprises an isolated polypeptide (i) comprising an amino acid sequence selected from the group consisting of SEQ ID NOs: 82-84, 87-97, 99, 101-103 and 117-138; or (ii) consisting of an amino acid sequence selected from the group consisting of SEQ ID NOs: 3-81, 85, 86, 98, 100, 104-116 and 139. A further embodiment of the invention comprises an isolated polypeptide (i) comprising an amino acid sequence selected from the group consisting of SEQ ID NOs: 82-84, 87-97, 99, 101-103, 117-130 and 132-138; or (ii) consisting of an amino acid sequence selected from the group consisting of SEQ ID NOs: 3, 7, 9, 10, 12-28, 30-38, 40, 42, 44-60, 62-68, 70-81, 85, 86, 98, 100 and 106-116.

Another embodiment of the invention comprises a pharmaceutical composition comprising an isolated polypeptide comprising or consisting of an amino acid sequence selected from the group consisting of SEQ ID NOs: 3-139 and a pharmaceutically acceptable carrier. A further embodiment of the invention comprises a composition comprising an isolated polypeptide comprising or consisting of an amino acid sequence selected from the group consisting of SEQ ID NOs: 3-139 in association with one or more members selected from the group consisting of anti-human CD81 antibody, ribavirin, interferon alfa-2a, interferon alfa-2b, interferon alfa-2c, interferon alfa n-1, interferon alfa n-3, consensus interferon, pegylated interferon alfa-2a, pegylated interferon alfa-2b, pegylated interferon alfa-2c, pegylated interferon alfa n-1, pegylated interferon alfa n-3, and pegylated consensus interferon (e.g., a kit). In an embodiment of the invention, an isolated peptide of the invention is combined in association with an HCV protease inhibitor or an HCV polymerase inhibitor.

The present invention also includes an oligonucleotide comprising the nucleotide sequence set forth in SEQ ID NO: 140 or 141.

The present invention also provides an isolated polynucleotide encoding a polypeptide comprising or consisting of an amino acid sequence selected from the group consisting of SEQ ID NOs: 3-139. In an embodiment of the invention, the polynucleotide encodes a polypeptide comprising or consisting of the amino acid sequence of SEQ ID NO: 3, 7, 9, 10, 12-28, 30-38, 40, 42, 44-60, 62-68, 70, 71, 73-103, 106-120, 121-130 or 132-138. A further embodiment of the invention comprises a recombinant vector comprising an isolated polynucleotide encoding a polypeptide comprising or consisting of an amino acid sequence selected from the group consisting of SEQ ID NOs: 3-139. Another embodiment of the invention comprises an isolated host cell comprising the vector.

The present invention also provides a method for making a polypeptide (e.g., any of SEQ ID NOs: 3-139) comprising culturing a host cell comprising a polynucleotide encoding the polypeptide under conditions in which the polynucleotide is expressed and, optionally, isolating the polypeptide from the culture.

The present invention also provides a method for inhibiting entry of a virus which is a member of the Flaviviridae family (e.g., hepatitis C virus) into a cell (e.g., in vitro or in vivo) comprising contacting the cell with a polypeptide comprising or consisting of an amino acid sequence selected from the group consisting of SEQ ID NOs: 3-139. Also provided by the present invention is a method for treating or preventing infection of a subject with a virus which is a member of the Flaviviridae family comprising administering to said subject a therapeutically effective amount of a polypeptide of the present invention (e.g., any of SEQ ID Nos 3-139). In an embodiment of the invention, the polypeptide (e.g., any of SEQ ID NOs: 3-139) is administered in association with one or more members selected from the group consisting of anti-human CD81 antibody, ribavirin, interferon alfa-2a, interferon alfa-2b, interferon alfa-2c, interferon alfa n-1, interferon alfa n-3, consensus interferon, pegylated interferon alfa-2a, pegylated interferon alfa-2b, pegylated interferon alfa-2c, pegylated interferon alfa n-1, pegylated interferon alfa n-3, and pegylated consensus interferon. In an embodiment of the invention, the pegylated interferon alfa that is administered is a pegylated interferon alfa-2b and wherein the amount of pegylated interferon alfa-2b that is administered in the treatment time period is about 0.5 to 1.5 micrograms per kilogram body weight of pegylated interferon alfa-2b protein per week on a weekly basis for at least twenty-four weeks (e.g., about 48 weeks). In an embodiment of the invention, said polypeptide (e.g., any of SEQ ID NOs: 3-139) is administered for a treatment time period sufficient to eradicate detectable hepatitis C virus-RNA and to maintain no detectable hepatitis C virus RNA for at least twelve weeks after the end of the treatment time period. In a further embodiment of the invention, said polypeptide (e.g., any of SEQ ID NOs: 3-139) is administered in association with a therapeutically effective amount of an interferon for a treatment time period sufficient to eradicate detectable hepatitis C virus-RNA and to maintain no detectable hepatitis C virus RNA for at least twelve weeks after the end of the treatment time period. In an embodiment of the invention, the host is infected with multiple hepatitis C virus genotypes (e.g., hepatitis C virus genotype 1 and/or hepatitis C virus genotype 2 and/or hepatitis C virus genotype 3).

The present invention also provides a method for preventing infection of a host, with a virus which is a member of the Flaviviridae family of viruses (e.g., hepatitis C virus), following transplantation of a liver into said host or transfusion of blood into said host comprising administering (e.g., parenterally (e.g., intramuscularly, intravenously, subcutaneously) or non-parenterally (e.g., orally)) to said host (e.g., before, during or after said transplantation or transfusion) a therapeutically effective amount of a polypeptide comprising or consisting of an amino acid sequence selected from the group consisting of SEQ ID NOs: 3-139. In an embodiment of the invention, the polypeptide (e.g., any of SEQ ID NOs: 3-139) is administered in association with anti-human CD81 antibody, interferon-alfa, pegylated interferon-alfa or albumin-interferon-alpha (e.g., interferon alfa-2a, interferon alfa-2b, interferon alfa-2c, interferon alfa n-1, interferon alfa n-3, consensus interferon, pegylated interferon alfa-2a, pegylated interferon alfa-2b, pegylated interferon alfa-2c, pegylated interferon alfa n-1, pegylated interferon alfa n-3, or pegylated consensus interferon). In an embodiment of the invention, the polypeptide (e.g., any of SEQ ID NOs: 3-139) is administered in association with ribavirin.

DETAILED DESCRIPTION OF THE INVENTION

The present invention provides peptide compositions (e.g., any of SEQ ID NOs: 3-139) and methods for treating or preventing an infection by a virus which is a member of the Flaviviridae family (e.g, HCV) in a subject (e.g., a patient who has received a liver transplant) by administering one or more of the peptides to the subject. In an embodiment of the invention, the peptide comprises the amino acid sequence of any of SEQ ID NOs: 3, 7, 9, 10, 12-28, 30-38, 40, 42, 44-60, 62-68, 70, 71, 73-103, 106-120, 121-130, 132-138.

A patient or host suffering from an infection by a Flaviviridae virus, such as HCV (e.g., a chronic or acute HCV infection), can be treated by administering to the patient an E1-E2 polypeptide (e.g., any of SEQ ID NOs: 3-139) or a pharmaceutically acceptable salt thereof.

An E1-E2 peptide (e.g., comprising the amino acid sequence of any of SEQ ID NO: 3-139) can also be administered to a patient in association with one or more other antiviral agents such as an anti-human CD81 antibody, pegylated or unpegylated interferon alfa-2a, pegylated or unpegylated interferon alfa-2b, pegylated or unpegylated interferon alfa-2c, pegylated or unpegylated interferon-alfa n-1, pegylated or unpegylated interferon alfa n-3 or pegylated or unpegylated consensus interferon.

In a liver transplantation procedure, the donor liver can come from a living donor (i.e., living donor liver transplantation (LDLT)) wherein a portion of the donor's liver is removed and introduced into the recipient. Alternatively, the transplant can be from a deceased donor wherein the entire liver is removed and transplanted.

For example, the present invention includes, but is not limited to methods for treating or preventing infections caused by members of the Hepacivirus genus which includes the hepatitis C virus (HCV). HCV includes several types, subtypes and isolates:

hepatitis C virus (isolate 1)
hepatitis C virus (isolate BK)
hepatitis C virus (isolate EC1)
hepatitis C virus (isolate EC10)
hepatitis C virus (isolate HC-J2)
hepatitis C virus (isolate HC-J5)
hepatitis C virus (isolate HC-J6)
hepatitis C virus (isolate HC-J7)
hepatitis C virus (isolate HC-J8)
hepatitis C virus (isolate HC-JT)
hepatitis C virus (isolate HCT18)
hepatitis C virus (isolate HCT27)
hepatitis C virus (isolate HCV-476)
hepatitis C virus (isolate HCV-KF)
hepatitis C virus (isolate Hunan)
hepatitis C virus (isolate Japanese)
hepatitis C virus (isolate Taiwan)
hepatitis C virus (isolate TH)
hepatitis C virus isolate H
hepatitis C virus type 1
hepatitis C virus type 1a
    hepatitis C virus strain H77
hepatitis C virus type 1b
hepatitis C virus type 1c
hepatitis C virus type 1d
hepatitis C virus type 1e
hepatitis C virus type 1f
hepatitis C virus type 10
hepatitis C virus type 2
hepatitis C virus type 2a
hepatitis C virus type 2b
hepatitis C virus type 2c
hepatitis C virus type 2d
hepatitis C virus type 2f
hepatitis C virus type 3
hepatitis C virus type 3a
hepatitis C virus type 3b
hepatitis C virus type 3g
hepatitis C virus type 4
hepatitis C virus type 4a
hepatitis C virus type 4c
hepatitis C virus type 4d
hepatitis C virus type 4f
hepatitis C virus type 4h
hepatitis C virus type 4k
hepatitis C virus type 5
hepatitis C virus type 5a
hepatitis C virus type 6
hepatitis C virus type 6a
hepatitis C virus type 7 hepatitis C virus type 7a hepatitis C virus type 7b hepatitis C virus type 8 hepatitis C virus type 8a

The present invention also includes methods for treating or preventing infection caused by members of the *Flavivirus* genus. The *Flavivirus* genus includes Yellow fever virus; Tick-borne viruses such as the Gadgets Gully virus, Kadam virus, Kyasanur Forest disease virus, Langat virus, Omsk hemorrhagic fever virus, Powassan virus, Royal Farm virus, Karshi virus, Tick-borne encephalitis virus, Neudoerfl virus, Neudoerfl virus, Sofin virus, Louping ill virus and the Negishi virus; seabird tick-borne viruses such as the Meaban virus, Saumarez Reef virus, and the Tyuleniy virus; mosquito-borne viruses such as the Aroa virus, Bussuquara virus, Iguape virus and the Naranjal virus; Dengue viruses such as the Dengue virus and the Kedougou virus; Japanese encephalitis viruses such as the Cacipacore virus, Koutango virus, Japanese encephalitis virus, Murray Valley encephalitis virus, Alfuy virus, St. Louis encephalitis virus, Usutu virus, West Nile virus, Kunjin virus and the Yaounde virus; Kokobera viruses such as the Kokobera virus and the Stratford virus; Ntaya viruses such as the Bagaza virus, Ilheus virus, Rocio virus, Israel turkey meningoencephalomyelitis virus, Ntaya virus and the Tembusu virus; Spondweni viruses such as the Zika virus and the Spondweni virus; Yellow fever viruses such as the Banzi virus, Bouboui virus, Edge Hill virus, Jugra virus, Saboya virus, Potiskum virus, Sepik virus, Uganda S virus, Wesselsbron virus and the Yellow fever virus; Entebbe viruses such as the Entebbe bat virus, Sokoluk virus, and the Yokose virus; Modoc viruses such as the Apoi virus, Cowbone Ridge virus, Jutiapa virus, Modoc virus, Sal Vieja virus and the San Perlita virus; Rio Bravo viruses such as the Bukalasa bat virus, Carey Island virus, Dakar bat virus, Montana myotis leukoencephalitis virus, Phnom Penh bat virus, Batu Cave virus, Rio Bravo virus, Tamana bat virus, and the Cell fusing agent virus.

The present invention also includes methods for treating or preventing infection caused by members of the Pestivirus genus. The Pestivirus genus includes Bovine viral diarrhea virus 1, Border disease virus (sheep), Bovine viral diarrhea virus 1, Bovine viral diarrhea virus 2, Classical swine fever virus, and Hog cholera virus.

Moreover, the present invention includes methods for treating or preventing infections caused by Hepatitis G virus or Hepatitis GB virus—A, B or C.

A "host", "subject" or "patient" may be any organism, such as a mammal (e.g., primate, dog, cat, cow, horse, pig, goat, rat, mouse, bird), preferably a human. A host, subject or patient can be an organism, such as a human, that is co-infected with another virus such as the human immunodeficiency virus (HIV; e.g., HIV-1 or HIV-2). Accordingly, the present invention comprises methods and compositions for treating Flaviviridae infection in a host this also infected with HIV.

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, et al. (eds.), *Current Protocols in Molecular Biology*, John Wiley & Sons, Inc. (1994).

The HCV E1 protein is well known in the art. For example, the an amino acid sequence of the HCV E1 protein is:

(SEQ ID NO: 1)
```
yqvrnssgly hvtndcpnss ivyeaadail htpgcvpcvr egnasrcwva vtptvatrdg klpttqlrrh idllvgsatl csalyvgdlc gsvflvgqlf tfsprrhwtt qdcncsiypg hitghrmawd mmmnwsptaa lvvaqllrip qaimdmiaga hwgvlagiay fsmvgnwakv lvvlllfagv da
```

(see also Genbank accession no. NP_751920)

The HCV E2 protein is well known in the art. For example, the an amino acid sequence of the HCV E2 protein is:

(SEQ ID NO: 2)
```
ethvtggsag rttaglvgll tpgakqniql intngswhin stalncnesl ntgwlaglfy qhkfnssgcp erlascrrlt dfaqgwgpis yangsglder pycwhypprp cgivpaksvc gpvycftpsp vvvgttdrsg aptyswgand tdvfvlnntr pplgnwfgct wmnstgftkv cgappcvigg vgnntllcpt dcfrkhpeat ysrcgsgpwi tprcmvdypy rlwhypctin ytifkvrmyv ggvehrleaa cnwtrgercd ledrdrsels plllsttqwq vlpcsfttlp alstglihlh qnivdvqyly gvgssiaswa ikweyvvllf llladarvcs clwmmllisq aea
```

(see also Genbank accession nos. NP_751921; AAB67038; AAB67036 and P27958).

The entire HCV genome is also disclosed, for example, under Genbank accession nos. AAB67038; NP_671491; MB67036; AAG02099; MB67037; and MP69952.

An example of a human CD81 is disclosed under Genbank accession no. NM004356.

A "polynucleotide", "nucleic acid" or "nucleic acid molecule" includes the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in single stranded form, double-stranded form or otherwise.

A "polynucleotide sequence", "nucleic acid sequence" or "nucleotide sequence" is a series of nucleotide bases (also called "nucleotides") in a nucleic acid, such as DNA or RNA, and means any chain of two or more nucleotides.

A "coding sequence" or a sequence "encoding" an expression product, such as a RNA, polypeptide, protein, or enzyme, is a nucleotide sequence that, when expressed, results in production of the product.

The term "gene" means a DNA sequence that codes for or corresponds to a particular sequence of ribonucleotides or amino acids which comprise all or part of one or more RNA molecules, proteins or enzymes, and may or may not include regulatory DNA sequences, such as promoter sequences, which determine, for example, the conditions under which the gene is expressed. Genes may be transcribed from DNA to RNA which may or may not be translated into an amino acid sequence.

The present invention includes any nucleic acid fragment encoding a polypeptide taken from of any of SEQ ID NOs: 1 and 2. An embodiment of the invention includes any nucleic acid including at least about 24 (e.g., 25, 26, 27, 28, 29, 30, 31, 32, 33, 34), preferably at least about 35 (e.g., 25, 26, 27, 28, 29, 30, 31, 32, 33 or 34), more preferably at least about 45 (e.g., 35, 36, 37, 38, 39, 40, 41, 42, 43 or 44), and most preferably at least about 126 or more contiguous nucleotides (e.g., 130, 131, 132, 133, 134, 135, 136, 137, 138, 139, 140, 150, 160, 170, 180, 190, 200, 300, 400, 500, 1000 or 1200) from any polynucleotide encoding a polypeptide of any of SEQ ID NOs: 1 or 2 (e.g., any of SEQ ID NOs: 3-139).

An embodiment of the invention includes any polynucleotide that encodes any of the polypeptides of the invention (e.g., any of SEQ ID NOs: 3-139), particularly any of SEQ ID NOs: 3, 7, 9, 10, 12-28, 30-38, 40, 42, 44-60, 62-68, 70, 71, 73-103, 106-120, 121-130, 132-138.

As used herein, the term "oligonucleotide" refers to a nucleic acid, generally of no more than about 100 nucleotides (e.g., 30, 40, 50, 60, 70, 80, or 90), that may be hybridizable to a genomic DNA molecule, a cDNA molecule, or an mRNA molecule encoding a gene, mRNA, cDNA, or other nucleic acid of interest. Oligonucleotides can be labeled, e.g., by incorporation of $^{32}$P-nucleotides, $^{3}$H-nucleotides, $^{14}$C-nucleotides, $^{35}$S-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the gene, or to detect the presence of nucleic acids. Generally, oligonucleotides are prepared synthetically, preferably on a nucleic acid synthesizer.

A "protein sequence", "peptide sequence" or "polypeptide sequence" or "amino acid sequence" includes a series of two or more amino acids in a protein, peptide or polypeptide.

"Protein", "peptide" or "polypeptide" includes a contiguous string of two or more amino acids. An embodiment of the invention includes any polypeptide comprising at least about 7 (e.g., 8, 9, 10, 11, 12, 13, 14, 15, 16, 17, 18 or 19), more preferably at least about 20 (e.g., 21, 22, 23, 24, 25, 26, 27, 28, 29, 30, 35, 40), and yet more preferably at least about 42 (e.g., 43, 44, 45, 46, 47, 48, 49, 50, 60, 70, 80, 90, 100, 110, 120 or 130) or more contiguous amino acid residues from SEQ ID NOs: 1 or 2 (e.g., any of SEQ ID NOs: 3-139).

The scope of the present invention includes any of the polypeptides described herein (e.g., any of SEQ ID NOs: 3-139) comprising either D- or L-amino acids or one or more of either. For example, the present invention includes LVal-L-Ser- L-Phe- L-Ala- L-Ile- L-Lys- L-Trp- L-Glu- L-Tyr- L-Val- L-Leu- L-Leu- L-Leu- L-Phe- L-Leu- L-Leu (SEQ ID NO: 77) as well as, for example. D-Val-D-Ser-D-Phe-D-Ala-D-Ile-D-Lys-D-Trp-D-Glu-D-Tyr-D-Val-D-Leu-D-Leu-D-Leu-D-Phe-D-Leu-D-Leu and L-Val-D-Ser-L-Phe-L-Ala-D-Ile-L-Lys-L-Trp-D-Glu-L-Tyr-L-Val-L-Leu-D-Leu-L-Leu-L-Phe-L-Leu-D-Leu. The present invention also includes any of the polypeptides described herein along with the reverse version of each peptide. For example, the present invention includes V-S-F-A-I-K-W-E-Y-V-L-L-L-F-L-L (SEQ ID NO: 77) along with the reverse of this peptide: L-L-F-L-L-L-V-Y-E-W-K-T-A-F-S-V (SEQ ID NO: 142).

The terms "isolated polynucleotide" or "isolated polypeptide" include a polynucleotide (e.g., RNA or DNA molecule, or a mixed polymer) or a polypeptide, respectively, which are partially or fully separated from other components that are normally found in cells or in recombinant DNA expression systems. These components include, but are not limited to, cell membranes, cell walls, ribosomes, polymerases, serum components and extraneous genomic sequences.

An isolated polynucleotide or polypeptide will, preferably, be an essentially homogeneous composition of molecules but may contain some heterogeneity.

"Amplification" of DNA as used herein includes the use of polymerase chain reaction (PCR) to increase the concentration of a particular DNA sequence within a mixture of DNA sequences. For a description of PCR see Saiki, et al., Science (1988) 239:487.

The term "host cell" includes any cell of any organism that is selected, modified, transfected, transformed, grown, or used or manipulated in any way, for the production of a substance by the cell, for example the expression or replication, by the cell, of a gene, a DNA or RNA sequence or a protein (e.g., chinese hamster ovary (CHO) cells and bacterial cells including *E. coli* (e.g., BL21, BL21 DE3, DH5, DH5α and HB101 cells)).

The nucleotide sequence of a nucleic acid may be determined by any method known in the art (e.g., chemical sequencing or enzymatic sequencing). "Chemical sequencing" of DNA includes methods such as that of Maxam and Gilbert (1977) (Proc. Natl. Acad. Sci. USA 74:560), in which DNA is randomly cleaved using individual base-specific reactions. "Enzymatic sequencing" of DNA includes methods such as that of Sanger (Sanger, et al., (1977) Proc. Natl. Acad. Sci. USA 74:5463).

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

In general, a "promoter" or "promoter sequence" is a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences or with a nucleic acid of the invention. Promoters which may be used to control gene expression include, but are not limited to, cytomegalovirus (CMV) promoter (U.S. Pat. Nos. 5,385,839 and 5,168,062), the SV40 early promoter region (Benoist, et al., (1981) Nature 290:304-310), the promoter contained in the 3' long terminal repeat of Rous sarcoma virus (Yamamoto, et al., (1980) Cell 22:787-797), the herpes thymidine kinase promoter (Wagner, et al., (1981) Proc. Natl. Acad. Sci. USA 78:1441-1445), the regulatory sequences of the metallothionein gene (Brinster, et al., (1982) Nature 296:39-42); prokaryotic promoters such as the β-lactamase promoter (Villa-Komaroff, et al., (1978) Proc. Natl. Acad. Sci. USA 75:3727-3731), or the tac promoter (DeBoer, et al., (1983) Proc. Natl. Acad. Sci. USA 80:21-25); see also "Useful proteins from recombinant bacteria" in Scientific American (1980) 242:74-94; and promoter elements from yeast or other fungi such as the Gal 4 promoter, the ADH (alcohol dehydrogenase) promoter, PGK (phosphoglycerol kinase) promoter or the alkaline phosphatase promoter.

A coding sequence is "under the control of", "functionally associated with" or "operably associated with" a transcriptional and translational control sequence in a cell (e.g., a promoter), for example, when the sequence directs RNA polymerase mediated transcription of the coding sequence into RNA, preferably mRNA, which then may be RNA spliced (if it contains introns) and, optionally, translated into a protein encoded by the coding sequence.

The terms "express" and "expression" mean allowing or causing the information in a gene, RNA or DNA sequence to become manifest; for example, producing a protein by activating the cellular functions involved in transcription and translation of a corresponding gene. A DNA sequence is expressed in or by a cell to form an "expression product" such as an RNA (e.g., mRNA) or a protein. The expression product itself may also be said to be "expressed" by the cell.

The term "transformation" means the introduction of a nucleic acid into a cell. The introduced gene or sequence may be called a "clone". A host cell that receives the introduced DNA or RNA has been "transformed" and is a "transformant" or a "clone." The DNA or RNA introduced to a host cell can come from any source, including cells of the same genus or species as the host cell, or from cells of a different genus or species. The introduced nucleic acid can be maintained in the cell episomally or may be integrated into a chromosome of the cell.

The term "vector" includes a vehicle (e.g., a plasmid) by which a DNA or RNA sequence can be introduced into a host cell, so as to transform the host and, optionally, promote expression and/or replication of the introduced sequence.

Vectors that can be used in this invention include plasmids, viruses, bacteriophage, integratable DNA fragments, and other vehicles that may facilitate introduction of the nucleic acids into the genome of the host. Plasmids are the most commonly used form of vector but all other forms of vectors which serve a similar function and which are, or become, known in the art are suitable for use herein. See, e.g., Pouwels, et al., *Cloning Vectors: A Laboratory Manual,* 1985 and Supplements, Elsevier, N.Y., and Rodriguez et al. (eds.), *Vectors: A Survey of Molecular Cloning Vectors and Their Uses,* 1988, Buttersworth, Boston, Mass.

The term "expression system" means a host cell and compatible vector which, under suitable conditions, can express a protein or nucleic acid which is carried by the vector and introduced to the host cell. Common expression systems include *E. coli* host cells and plasmid vectors, insect host cells and Baculovirus vectors, and mammalian host cells and vectors.

Expression of nucleic acids encoding the E1-E2 polypeptides of this invention (e.g., SEQ ID NOs: 3-139) can be carried out by conventional methods in either prokaryotic or eukaryotic cells. Although *E. coli* host cells are employed most frequently in prokaryotic systems, many other bacteria, such as various strains of *Pseudomonas* and *Bacillus,* are known in the art and can be used as well. Suitable host cells for expressing nucleic acids encoding the E1-E2 polypeptides include prokaryotes and higher eukaryotes. Prokaryotes include both gram-negative and gram-positive organisms, e.g., *E. coli* and *B. subtilis*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. A representative vector for amplifying DNA is pBR322 or many of its derivatives (e.g., pUC18 or 19). Vectors that can be used to express the E1-E2 polypeptides (e.g., SEQ ID NOs: 3-139) include, but are not limited to, those containing the lac promoter (pUC-series); trp promoter (pBR322-trp); lpp promoter (the pIN-series); lambda-pP or pR promoters (pOTS); or hybrid promoters such as ptac (pDR540). See Brosius et al., "Expression Vectors Employing Lambda-, trp-, lac-, and lpp-derived Promoters", in Rodriguez and Denhardt (eds.) *Vectors: A Survey of Molecular Cloning Vectors and Their Uses,* 1988, Buttersworth, Boston, pp. 205-236. Many polypeptides can be expressed, at high levels, in an *E. coli*/T7 bacteriophage expression system as disclosed in U.S. Pat. Nos. 4,952,496, 5,693,489 and 5,869,320 and in Davanloo, P., et al., (1984) Proc. Natl. Acad. Sci. USA 81: 2035-2039; Studier, F. W., et al., (1986) J. Mol. Biol. 189: 113-130; Rosenberg, A. H., et al., (1987) Gene 56: 125-135; and Dunn, J. J., et al., (1988) Gene 68: 259.

Higher eukaryotic tissue culture cells may also be used for the recombinant production of the E1-E2 polypeptides of the invention (e.g., SEQ ID NOs: 3-139). Although any higher eukaryotic tissue culture cell line might be used, including insect baculovirus expression systems, mammalian cells are preferred. Transformation or transfection and propagation of such cells have become a routine procedure. Examples of useful cell lines include HeLa cells, chinese hamster ovary (CHO) cell lines, J774 cells, Caco2 cells, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and/or a transcription termination site. These vectors also, usually, contain a selection gene or amplification gene. Suitable expression vectors may be plasmids, viruses, or retroviruses carrying promoters derived, e.g., from such sources as adenovirus, SV40, parvoviruses, vaccinia virus, or cytomegalovirus. Examples of expression vectors include pCR®3.1, pCDNA1, pCD (Okayama, et al., (1985)

Mol. Cell Biol. 5:1136), pMC1neo Poly-A (Thomas, et al., (1987) Cell 51:503), pREP8, pSVSPORT and derivatives thereof, and baculovirus vectors such as pAC373 or pAC610.

The present invention also includes fusions which include any of the E1-E2 polypeptides (e.g., SEQ ID NOs: 3-139) and E1-E2 polynucleotides encoding said polypeptides of the present invention or a fragment thereof (discussed above) and a second polypeptide or polynucleotide moiety, which may be referred to as a "tag". The fused polypeptides of the invention may be conveniently constructed, for example, by insertion of a polynucleotide of the invention or fragment thereof into an expression vector. The fusions of the invention may include tags which facilitate purification or detection. Such tags include glutathione-5-transferase (GST), hexahistidine (His6) tags, maltose binding protein (MBP) tags, haemagglutinin (HA) tags, cellulose binding protein (CBP) tags and myc tags. Detectable tags such as $^{32}P$, $^{35}S$, $^{3}H$, $^{99m}Tc$, $^{123}I$, $^{111}In$, $^{68}Ga$, $^{18}F$, $^{125}I$, $^{131}I$, $^{113m}In$, $^{76}Br$, $^{67}Ga$, $^{99m}Tc$, $^{123}I$, $^{111}In$ and $^{68}Ga$ may also be used to label the polypeptides and polynucleotides of the invention. Methods for constructing and using such fusions are very conventional and well known in the art.

Modifications (e.g., post-translational modifications) that occur in a polypeptide often will be a function of how it is made. For polypeptides made by expressing a cloned gene in a host, for instance, the nature and extent of the modifications, in large part, will be determined by the host cell's post-translational modification capacity and the modification signals present in the polypeptide amino acid sequence. For instance, as is well known, glycosylation often does not occur in bacterial hosts such as E. coli. Accordingly, when glycosylation is desired, a polypeptide can be expressed in a glycosylating host, generally a eukaryotic cell. Insect cells often carry out post-translational glycosylations which are similar to those of mammalian cells. For this reason, insect cell expression systems have been developed to express, efficiently, proteins having glycosylation. An insect cell which may be used in this invention is any cell derived from an organism of the class Insecta. For example, the insect can be Spodoptera fruigiperda (Sf9 or Sf21) or Trichoplusia ni (High 5). Examples of insect expression systems that can be used with the present invention, for example to produce E1-E2 polypeptide (e.g., SEQ ID NOs: 3-139), include Bac-To-Bac (Invitrogen Corporation, Carlsbad, Calif.) or Gateway (Invitrogen Corporation, Carlsbad, Calif.). If desired, deglycosylation enzymes can be used to remove carbohydrates attached during production in eukaryotic expression systems.

Other modifications may also include addition of aliphatic esters or amides to the polypeptide carboxyl terminus. The present invention also includes analogs of the E1-E2 polypeptides (e.g., SEQ ID NOs: 3-139) which contain modifications, such as incorporation of unnatural amino acid residues, or phosphorylated amino acid residues such as phosphotyrosine, phosphoserine or phosphothreonine residues. Other potential modifications include sulfonation, biotinylation, or the addition of other moieties. For example, the E1-E2 polypeptides of the invention (e.g., SEQ ID NOs: 3-139) may be appended with a polymer which increases the half-life of the peptide in the body of a subject. Polymers include polyethylene glycol (PEG) (e.g., PEG with a molecular weight of 2 kDa, 5 kDa, 10 kDa, 12 kDa, 20 kDa, 30 kDa and 40 kDa), dextran and monomethoxypolyethylene glycol (mPEG).

The peptides of the invention may also be cyclized. Specifically, the amino- and carboxy-terminal residues of an E1-E2 polypeptide (e.g., SEQ ID NOs: 3-139) or two internal residues of an E1-E2 polypeptide of the invention (e.g., SEQ ID NOs: 3-139) or a terminal and an internal residue of an E1-E3 polypeptide of the invention (e.g., SEQ ID NOs: 3-139) can be fused to create a cyclized peptide. Methods for cyclizing peptides are conventional and very well known in the art; for example see Gurrath, et al., (1992) Eur. J. Biochem. 210:911-921.

The present invention contemplates any superficial or slight modification to the amino acid or nucleotide sequences which correspond to the E1-E2 polypeptides of the invention (e.g., SEQ ID NOs: 3-139). In particular, the present invention contemplates sequence conservative variants of the nucleic acids which encode the polypeptides of the invention. "Sequence-conservative variants" of a polynucleotide sequence are those in which a change of one or more nucleotides in a given codon results in no alteration in the amino acid encoded at that position. Function-conservative variants of the polypeptides of the invention (e.g., any of SEQ ID NOs: 3-139) are also contemplated by the present invention along with nucleic acids encoding the variants. "Function-conservative variants" are those in which one or more amino acid residues in a protein or enzyme have been changed without significantly altering the overall conformation and/or function of the polypeptide, including, but, by no means limited to, replacement of an amino acid with one having similar properties. Amino acids with similar properties are well known in the art. For example, polar/hydrophilic amino acids which may be interchangeable include asparagine, glutamine, serine, cysteine, threonine, lysine, arginine, histidine, aspartic acid and glutamic acid; nonpolar/hydrophobic amino acids which may be interchangeable include glycine, alanine, valine, leucine, isoleucine, proline, tyrosine, phenylalanine, tryptophan and methionine; acidic amino acids which may be interchangeable include aspartic acid and glutamic acid and basic amino acids which may be interchangeable include histidine, lysine and arginine.

The present invention includes E1-E2 polynucleotides (e.g., any polynucleotide encoding a polypeptide comprising an amino acid sequence selected from SEQ ID NOs: 3-139) and fragments thereof as well as nucleic acids which hybridize to the polynucleotides. Preferably, the nucleic acids hybridize under low stringency conditions, more preferably under moderate stringency conditions and most preferably under high stringency conditions. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook, et al., supra). The conditions of temperature and ionic strength determine the "stringency" of the hybridization. Typical low stringency hybridization conditions are 55° C., 5×SSC, 0.1% SDS, 0.25% milk, and no formamide at 42° C.; or 30% formamide, 5×SSC, 0.5% SDS at 42° C. Typical, moderate stringency hybridization conditions are similar to the low stringency conditions except the hybridization is carried out in 40% formamide, with 5× or 6×SSC at 42° C. High stringency hybridization conditions are similar to low stringency conditions except the hybridization conditions are carried out in 50% formamide, 5× or 6×SSC and, optionally, at a higher temperature (e.g., higher than 42° C.: 57° C., 59° C., 60° C., 62° C., 63° C., 65° C. or 68° C.). In general, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.51). For hybridization with shorter nucleic acids, i.e., oligonucleotides, the position of mismatches becomes more important, and the length of the oligonucleotide determines its specificity (see Sambrook, et al., supra).

Also included in the present invention are polynucleotides comprising nucleotide sequences and polypeptides comprising amino acid sequences which are at least about 70% identical, preferably at least about 80% identical, more preferably at least about 90% identical and most preferably at least about 95% identical (e.g., 95%, 96%, 97%, 98%, 99%, 100%) to the reference E1-E2 nucleotide and amino acid sequences (e.g., SEQ ID NOs: 3-139) of the invention, when the comparison is performed by a BLAST algorithm wherein the parameters of the algorithm are selected to give the largest match between the respective sequences over the entire length of the respective reference sequences. Polypeptides comprising amino acid sequences which are at least about 70% similar, preferably at least about 80% similar, more preferably at least about 90% similar and most preferably at least about 95% similar (e.g., 95%, 96%, 97%, 98%, 99%, 100%) to the reference E1-E2 amino acid sequence of any of SEQ ID NOs: 3-139, when the comparison is performed with a BLAST algorithm wherein the parameters of the algorithm are selected to give the largest match between the respective sequences over the entire length of the respective reference sequences, are also included in the present invention.

Sequence identity refers to exact matches between the nucleotides or amino acids of two sequences which are being compared. Sequence similarity refers to both exact matches between the amino acids of two polypeptides which are being compared in addition to matches between nonidentical, biochemically related amino acids. Biochemically related amino acids which share similar properties and may be interchangeable are discussed above.

The following references regarding the BLAST algorithm are herein incorporated by reference: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M., et al., (1994) Comput. Appl. Biosci. 10:67-70; ALIGNMENT SCORING SYSTEMS: Dayhoff, M. O., et al., "A model of evolutionary change in proteins." in *Atlas of Protein Sequence and Structure*, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in *Atlas of Protein Sequence and Structure*, (1978) vol. 5, suppl. 3. M. O. Dayhoff (ed.), pp. 353-358, Natl. Biomed. Res. Found., Washington, D.C., Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in *Theoretical and Computational Methods in Genome Research* (S. Suhai, ed.), (1997) pp. 1-14, Plenum, N.Y.

Protein Purification

The polypeptides of this invention (e.g., SEQ ID NOs: 3-139) can be purified by standard methods, including, but not limited to, salt or alcohol precipitation, affinity chromatography (e.g., used in conjunction with a purification tagged E1-E2 polypeptide as discussed above), preparative disc-gel electrophoresis, isoelectric focusing, high pressure liquid chromatography (HPLC), reversed-phase HPLC, gel filtration, cation and anion exchange and partition chromatography, and countercurrent distribution. Such purification methods are well known in the art and are disclosed, e.g., in "*Guide to Protein Purification*". Methods in Enzymology, Vol. 182, M. Deutscher, Ed., 1990, Academic Press, New York, N.Y.

Where an E1-E2 polypeptide (e.g., any of SEQ ID NOs: 3-139) is being isolated from a cellular or tissue source, it is preferable to include one or more inhibitors of proteolytic enzymes in the assay system, such as phenylmethanesulfonyl fluoride (PMSF), Pefabloc SC, pepstatin, leupeptin, chymostatin and EDTA.

Pharmaceutical Compositions

The present invention includes methods for using a pharmaceutical composition comprising a peptide of the present invention (e.g., any of SEQ ID NOs: 3-139) and a pharmaceutically acceptable carrier for treating a Flaviviridae infection. The pharmaceutical compositions may be prepared by any methods well known in the art of pharmacy; see, e.g., Gilman, et al., (eds.) (1990), *The Pharmacological Bases of Therapeutics*, 8th Ed., Pergamon Press; A. Gennaro (ed.), *Remington's Pharmaceutical Sciences*, 18th Edition, (1990), Mack Publishing Co., Easton, Pa.; Avis, et al., (eds.) (1993) *Pharmaceutical Dosage Forms: Parenteral Medications* Dekker, New York; Lieberman, et al., (eds.) (1990) *Pharmaceutical Dosage Forms: Tablets* Dekker, New York; and Lieberman, et al., (eds.) (1990), *Pharmaceutical Dosage Forms: Disperse Systems* Dekker, New York.

A pharmaceutical composition containing an E1-E2 peptide of the present invention (e.g., any of SEQ ID NOs: 3-139) can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like. All routes of administration are contemplated including, but not limited to, parenteral (e.g., subcutaneous, intravenous, intraperitoneal, intramuscular) and non-parenteral (e.g., oral, transdermal, intranasal, intraocular, sublingual, inhalation, rectal and topical).

Unit forms of administration include oral forms such as tablets, capsules, powders, cachets, granules and solutions or suspensions, sublingual and buccal forms of administration, aerosols, implants, subcutaneous, intramuscular, intravenous, intranasal, intraocular, subcutaneous or rectal forms of administration.

When a solid composition is prepared in the form of tablets, e.g., a wetting agent such as sodium lauryl sulfate can be added to micronized or non-micronized compounds and mixed with a pharmaceutical vehicle such as silica, gelatin starch, lactose, magnesium stearate, talc, gum arabic or the like. The tablets can be coated with sucrose, various polymers, or other appropriate substances. Tablets can be treated so as to have a prolonged or delayed activity and so as to release a predetermined amount of active principle continuously or at predetermined intervals, e.g., by using ionic resins and the like.

A preparation in the form of gelatin capsules may be obtained, e.g., by mixing an E1-E2 peptide of the present invention (e.g., any of SEQ ID NOs: 3-139) with a diluent, such as a glycol or a glycerol ester, and incorporating the resulting mixture into soft or hard gelatin capsules.

A preparation in the form of a syrup or elixir can contain an E1-E2 peptide of the present invention (e.g., any of SEQ ID NOs: 3-139), e.g., with a sweetener, methylparaben and propylparaben as antiseptics, flavoring agents and an appropriate color.

Water-dispersible powders or granules can contain an E1-E2 peptide of the present invention (e.g., any of SEQ ID NOs: 3-139) mixed, e.g., with dispersants, wetting agents or suspending agents, such as polyvinylpyrrolidone, as well as with sweeteners and/or other flavoring agents.

Rectal administration may be provided by using suppositories which may be prepared, e.g., with binders melting at the rectal temperature, for example cocoa butter or polyethylene glycols.

Parenteral, intranasal or intraocular administration may be provided by using, e.g., aqueous suspensions, isotonic saline solutions or sterile and injectable solutions containing pharmacologically compatible dispersants and/or solubilizers, for example, propylene glycol or polyethylene glycol.

Thus, to prepare an aqueous solution for intravenous injection, it is possible to use a co-solvent, e.g., an alcohol such as ethanol or a glycol such as polyethylene glycol or propylene glycol, and a hydrophilic surfactant such as Tween® 80. An oily solution injectable intramuscularly can be prepared, e.g., by solubilizing the active principle with a triglyceride or a glycerol ester.

Transdermal administration can be provided by using patches in the form of a multilaminate, or with a reservoir, containing an a peptide of the present invention (e.g., any of SEQ ID NOs: 3-139) and an appropriate solvent.

Administration by inhalation can be provided by using, e.g., an aerosol containing sorbitan trioleate or oleic acid, for example, together with trichlorofluoromethane, dichlorofluoromethane, dichlorotetrafluoroethane or any other biologically compatible propellant gas; it is also possible to use a system containing an E1-E2 peptide of the present invention (e.g., any of SEQ ID NOs: 3-139), by itself or associated with an excipient, in powder form.

An E1-E2 peptide of the present invention (e.g., any of SEQ ID NOs: 3-139) can also be formulated as microcapsules or microspheres, e.g., liposomes, optionally with one or more carriers or additives.

Implants are among the prolonged release forms which can be used in the case of chronic treatments. They can be prepared in the form of an oily suspension or in the form of a suspension of microspheres in an isotonic medium.

Methods of the present invention can include administration of an E1-E2 peptide of the present invention (e.g., any of SEQ ID NOs: 3-139) in association with, for example, one or more known anti-viral agents. The administration and dosage of such agents is typically as according to the schedule listed in the product information sheet of the approved agents, in the *Physicians' Desk Reference* 2003 (*Physicians' Desk Reference,* 57th Ed); Medical Economics Company; ISBN: 1563634457; 57th edition (November 2002), as well as therapeutic protocols well known in the art.

Suitable anti-viral agents, with which a peptide of the invention (e.g., any of SEQ ID NOs: 3-139) can be administered or mixed or formulated include, but are not limited to, pegylated or unpegylated interferon alfa-2a, pegylated or unpegylated interferon alfa-2b, pegylated or unpegylated interferon alfa-2c, pegylated or unpegylated interferon alfa n-1, pegylated or unpegylated interferon alfa n-3 and pegylated, unpegylated consensus interferon or albumin-interferon-alpha.

The term "interferon alpha" as used herein means the family of highly homologous species-specific proteins that inhibit viral replication and cellular proliferation and modulate immune response. Typical suitable interferon-alphas include, but are not limited to, recombinant interferon alpha-2b, recombinant interferon alpha-2a, recombinant interferon alpha-2c, alpha 2 interferon, interferon alpha-n1 (INS), a purified blend of natural alpha interferons, a consensus alpha interferon such as those described in U.S. Pat. Nos. 4,897,471 and 4,695,623 (especially Examples 7, 8 or 9 thereof), or interferon alpha-n3, a mixture of natural alpha interferons.

Interferon alfa-2a is sold as ROFERON-A® by Hoffmann-La Roche (Nutley, N.J.).

Interferon alfa-2b is sold as INTRON-A® by Schering Corporation (Kenilworth, N.J.). Interferon alfa-2b is also sold, in combination with ribavirin, as REBETRON® by Schering Corporation (Kenilworth, N.J.). The manufacture of interferon alpha 2b is described, for example, in U.S. Pat. No. 4,530,901.

Interferon alfa-n3 is a mixture of natural interferons sold as ALFERON N INJECTION® by Hemispherx Biopharma, Inc. (Philadelphia, Pa.).

Interferon alfa-n1 (INS) is a mixture of natural interferons sold as WELLFERON® by Glaxo-Smith-Kline (Research Triangle Park, N.C.).

Consensus interferon is sold as INFERGEN® by Intermune, Inc. (Brisbane, Calif.).

Interferon alfa-2c is sold as BEROFOR® by Boehringer Ingelheim Pharmaceutical, Inc. (Ridgefield, Conn.).

A purified blend of natural interferons is sold as SUMIFERON® by Sumitomo; Tokyo, Japan.

A multi-subtype natural interferon derived from human white blood cells is sold by Viragen, Inc (Plantation, Fla.), as Omniferon™. Viragen, Inc. also sells a highly purified, multi-subtype, natural human alpha interferon derived from human white blood cells, as Multiferon™ (U.S. Pat. No. 6,743,624).

Pegylated interferon alpha may also be administered in association with an E1-E2 peptide of the present invention (e.g., any of SEQ ID NOs: 3-139). The term "pegylated interferon alpha" as used herein means polyethylene glycol modified conjugates of interferon alpha, preferably interferon alpha-2a and alpha-2b. The preferred polyethylene-glycol-interferon alpha-2b conjugate is PEG 12000-interferon alpha-2b. The phrases "12,000 molecular weight polyethylene glycol conjugated interferon alpha" and "PEG 12000-IFN alpha" as used herein include conjugates such as are prepared according to the methods of International Application No. WO 95/13090 and containing urethane linkages between the interferon alpha-2a or -2b amino groups and polyethylene glycol having an average molecular weight of 12000. The pegylated inteferon alpha, PEG 12000-IFN-alpha-2b is available from Schering-Plough Research Institute, Kenilworth, N.J.

The preferred PEG 12000-interferon alpha-2b can be prepared by attaching a PEG polymer to the epsilon amino group of a lysine residue in the interferon alpha-2b molecule. A single PEG 12000 molecule can be conjugated to free amino groups on an IFN alpha-2b molecule via a urethane linkage. This conjugate is characterized by the molecular weight of PEG 12000 attached. The PEG 12000-IFN alpha-2b conjugate can be formulated as a lyophilized powder for injection.

Pegylated interferon alfa-2b is sold as PEG-INTRON® by Schering Corporation (Kenilworth, N.J.).

Pegylated interferon-alfa-2a is sold as PEGASYS® by Hoffmann-La Roche (Nutley, N.J.).

Other interferon alpha conjugates can be prepared by coupling an interferon alpha to a water-soluble polymer. A non-limiting list of such polymers include other polyalkylene oxide homopolymers such as polypropylene glycols, polyoxyethylenated polyols, copolymers thereof and block copolymers thereof. As an alternative to polyalkylene oxide-based polymers, effectively non-antigenic materials such as dextran, polyvinylpyrrolidones, polyacrylamides, polyvinyl alcohols, carbohydrate-based polymers and the like can be used. Such interferon alpha-polymer conjugates are described, for example, in U.S. Pat. No. 4,766,106, U.S. Pat. No. 4,917,888, European Patent Application No. 0 236 987 or 0 593 868 or International Publication No. WO 95/13090.

Pharmaceutical compositions of pegylated interferon alpha suitable for parenteral administration can be formulated with a suitable buffer, e.g., Tris-HCl, acetate or phosphate such as dibasic sodium phosphate/monobasic sodium phosphate buffer, and pharmaceutically acceptable excipients (e.g., sucrose), carriers (e.g. human plasma albumin), toxicity agents (e.g., NaCl), preservatives (e.g., thimerosol, cresol or benzyl alcohol), and surfactants (e.g., tween or polysorbates) in sterile water for injection. The pegylated interferon alpha can be stored as lyophilized powders under refrigeration at 2'-8° C. The reconstituted aqueous solutions are stable when stored between 2° and 8° C. and used within 24 hours of reconstitution. See for example U.S. Pat. Nos. 4,492,537; 5,762,923 and 5,766,582. The reconstituted aqueous solutions may also be stored in pre-filled, multi-dose syringes such as those useful for delivery of drugs such as insulin. Typical, suitable syringes include systems comprising a prefilled vial attached to a pen-type syringe such as the NOVOLET® Novo Pen available from Novo Nordisk or the REDIPEN®, available from Schering Corporation, Kenilworth, N.J. Other syringe systems include a pen-type syringe comprising a glass cartridge containing a diluent and lyophilized pegylated interferon alpha powder in a separate compartment.

In an embodiment of the invention, one or more other anti-viral substances may be administered with one or more E1-E2 peptides of the present invention (e.g., any of SEQ ID NOs: 3-139).

Other types of compounds which may be administered with an E1-E2 peptide of the present invention (e.g., any of SEQ ID NOs: 3-139) include, but are not limited to, ribonucleoside analogues, IMPDH inhibitors, N-glycosylation inhibitors, N3 protease inhibitors, NS5B inhibitors, immunomodulatory compounds and CTP synthase inhibitors, thiazolidine derivatives, benzanilides, phenanthrenequinones, helicase inhibitors, polymerase inhibitors, antisense phosphothioate oligodeoxynucleotides, IRES-dependent translation inhibitors, nuclease resistant ribozymes, 1-amino-alkyloyclohexanes, alkyl lipids, antioxidants, squalene, amantadine, bile acids, N-(phosphonoacetyl)-L-aspartic acid, benzenedicarboxamides, polyadenylic acid derivatives, 2',3' dideoxyinosine and benzimidazoles.

In an embodiment of the present invention, ribavirin ( 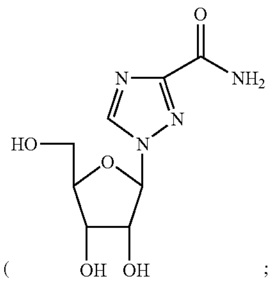  ;

1-β-D-ribofuranosyl-1H-1,2,4-triazole-3-carboxamide) is administered in association with an E1-E2 peptide of the present invention (e.g., any of SEQ ID NOs: 3-139). Ribavirin is sold as REBETOL® by Schering Corporation; Kenilworth, N.J. Its manufacture and formulation is described, for example, in U.S. Pat. No. 4,211,771. A combination of ribavirin and recombinant interferon alfa-2b (REBETRON®); Schering Corporation; Kenilworth, N.J.) may also be administered in association with an E1-E2 peptide of the present invention (e.g., any of SEQ ID NOs: 3-139).

In another embodiment of the invention, gemcitabine ( 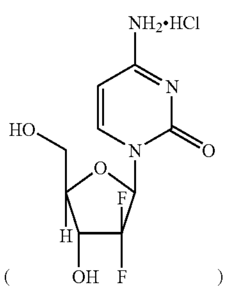  )

is administered in association with an E1-E2 peptide of the present invention (e.g., any of SEQ ID NOs: 3-139). Gemcitabine is sold as GEMZAR® by Eli Lilly and Co. (Indianapolis, Ind.).

A further embodiment of the present invention comprises administering an E1-E2 peptide of the present invention (e.g., any of SEQ ID NOs: 3-139) in association with VX497

( 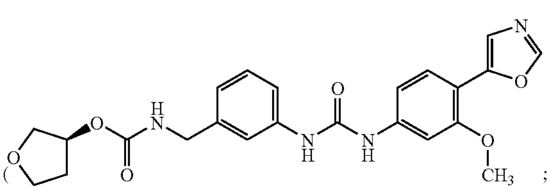  ;

Vertex Pharmaceuticals; Cambridge, Mass.).

An embodiment of the invention comprises administering mycophenolate mofetil (MMF; 2-morpholinoethyl (E)-6-(1, 3-dihydro-4-hydroxy-6-methoxy-7-methyl-3-oxo-5-isobenzofuranyl)-4-methyl-4-hexenoate) in association with an E1-E2 peptide of the present invention (e.g., any of SEQ ID NOs: 3-139). MMF is sold as CellCept® by Roche Laboratories; Nutley, N.J.

Another embodiment comprises administering EICAR

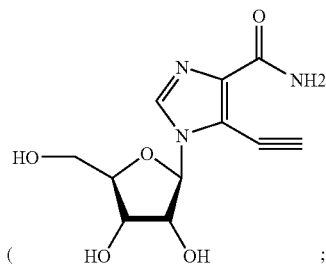

(5-ethynyl-1-beta-D-ribofuranosylimidazole-4-carboxamide; Balzarini et al., J. Biol. Chem. 268(33): 24591-24598 (1993)) in association with an E1-E2 peptide of the present invention (e.g., any of SEQ ID NOs: 3-139).

An embodiment of the present invention comprises administering tiazofurin

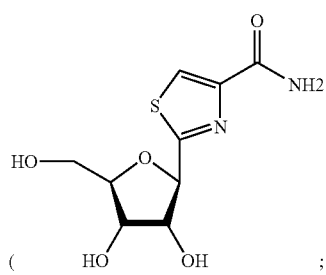

(Balzarini et al., J. Biol. Chem. 268(33): 24591-24598 (1993)) in association with an E1-E2 peptide of the present invention (e.g., any of SEQ ID NOs: 3-139).

Another embodiment of the invention comprises administering deoxynojirimycin and/or derivatives thereof, such as N-nonyl-deoxynojirimycin (De Clercq et al., Mini Rev Med. Chem. 2(2):163-75 (2002)) or n-butyl deoxynojirimycin (nB-DNJ; Ouzounov et al., Antiviral Res. 55(3):425-35 (2002)), in association with an E1-E2 peptide of the present invention (e.g., any of SEQ ID NOs: 3-139).

Another embodiment of the invention comprises administering colchicine

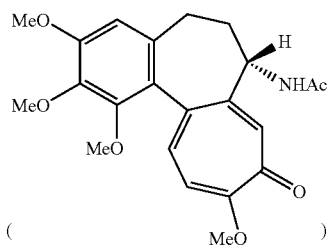

in association with an E1-E2 peptide of the invention (e.g., any of SEQ ID NOs: 3-139).

In one embodiment, an E1-E2 peptide of the present invention (e.g., any of SEQ ID NOs: 3-139) is administered in association with albumin-interferon alpha (ALBUFERON™). Albumin-interferon alpha is interferon-α fused to human serum albumin. ALBUFERON™ is available from Human Genome Sciences, Rockville, Md. ALBUFERON™ has been shown to be effective for treatment of hepatitis C virus infections (Blaire et al., J. Pharm and Exp. Therap. 303(2): 540-548 (2002)).

In another embodiment, BILN-2061

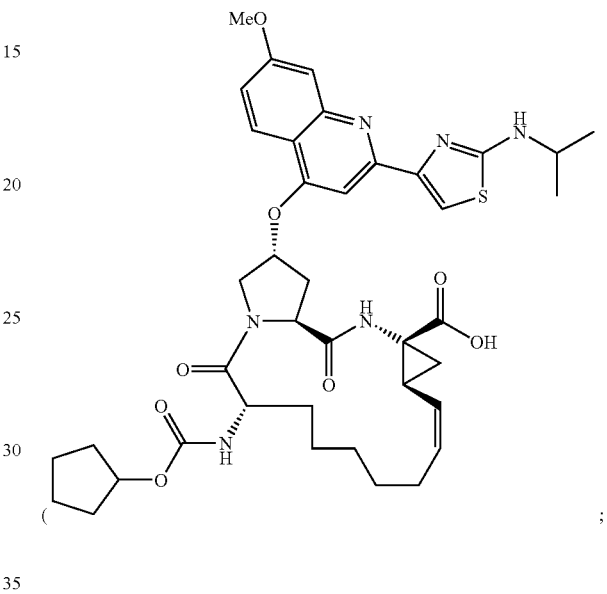

(Lamarre et al., Nature 426(6963):129-31 (2003)), is administered in association with an E1-E2 peptide of the present invention (e.g., any of SEQ ID NOs: 3-139).

In another embodiment, thymalfasin (e.g., ZADAXIN™) is administered in association with an E1-E2 peptide of the present invention (e.g., any of SEQ ID NOs: 3-139). ZADAXIN™ is available from SciClone Pharmaceuticals International, Ltd., San Mateo, Calif.

In yet another embodiment, isatoribine

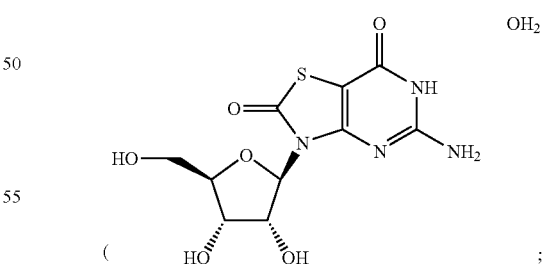

(ANA245; 5-Amino-3-beta-D-ribofuranosylthiazolo(4,5-d) pyrimidine-2,7(3H,6H)-dione monohydrate; Thiazolo(4,5-d)pyrimidine-2,7(3H,4H)-dione, 5-amino-3-beta-D-ribofuranosyl-, monohydrate) is administered in association with an E1-E2 peptide of the present invention (e.g., any of SEQ ID NOs: 3-139).

In another embodiment, an E1-E2 peptide of the invention (e.g., any of SEQ ID NOs: 3-139) is administered in association with an NS5B inhibitor such as NM283 or NM107 (Idenix Pharmaceuticals; Cambridge, Mass.).

In another embodiment, an E1-E2 peptide of the present invention (e.g., any of SEQ ID NOs: 3-139) is administered in association with SCH68631

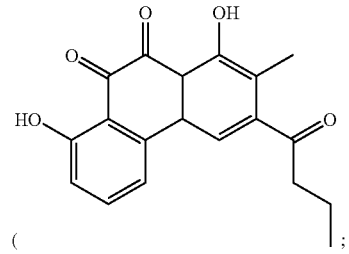

(Chu et al., Tetrahedron Letters 37(40): 7229-7232 (1996)) or SCH351633

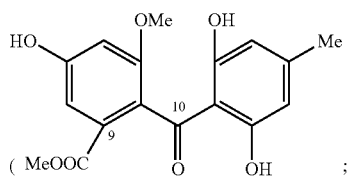

(Biorg. Med. Chem. Lett. 9(14): 1949-1952 (1999)).

In a further embodiment, an E1-E2 peptide of the present invention (e.g., any of SEQ ID NOs: 3-139) is administered in association with any of the $P_1$ variants of Elgin c disclosed in Qasim et al., Biochemistry 36: 1598-1607 (1997).

In yet another embodiment, an E1-E2 peptide of the present invention (e.g., any of SEQ ID NOs: 3-139) is administered in association with gliotoxin

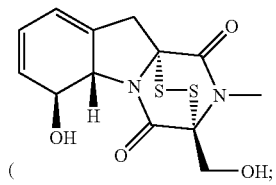

(Ferrari et al., J. Virology 73(2): 1649-1654 (1999)).

Other embodiments of the invention include administering an E1-E2 peptide of the present invention (e.g., any of SEQ ID NOs: 3-139) in association with RD3-4082

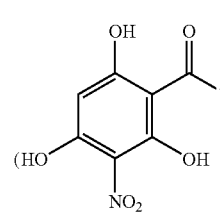

(Sudo et al., Anti-viral Chem. & Chemother. 9: 186 (1998)) or with RD3-4078

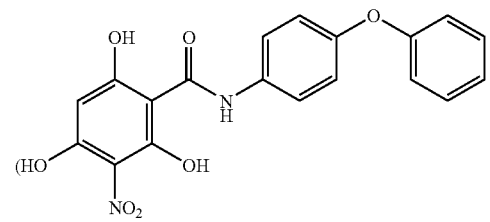

(Sudo et al., Anti-viral Chem. & Chemother. 9: 186 (1998)) or any other protease inhibitor disclosed in Sudo et al.

A further embodiment of the invention comprises administering an E1-E2 peptide of the present invention (e.g., any of SEQ ID NOs: 3-139) in association with

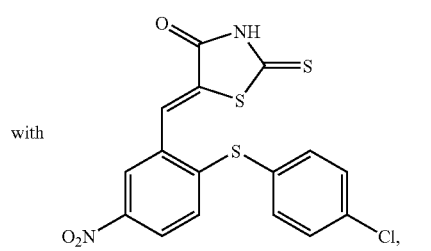

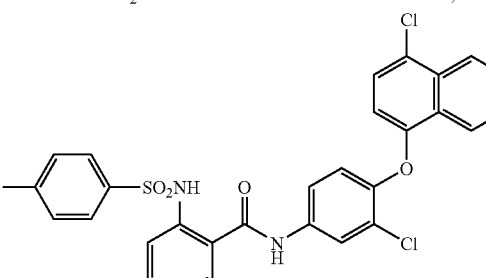

or

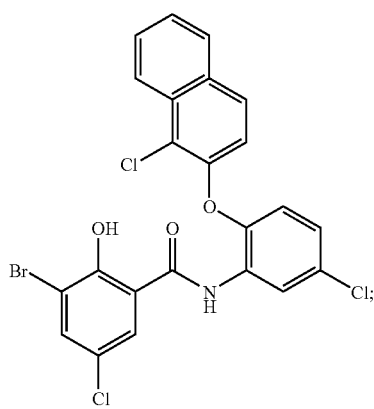

Kakiuchi et al., FEBS Letters 421: 217-220 (1998)) or any other proteinase inhibitor disclosed in Kakiuchi et al., A further embodiment of the invention comprises administering an E1-E2 peptide of the present invention (e.g., any of SEQ ID NOs: 3-139) in association with helioxanthin

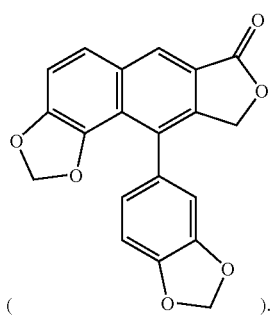

A further embodiment of the invention comprises administering an E1-E2 peptide of the present invention (e.g., any of SEQ ID NOs: 3-139) in association with HE2000 (16-Bromoepiandrosterone; 16-Br-Epi; 16alpha-Bromoepiandrosterone; Alpha-Epi-Br; 16alpha-Bromo-3beta-hydroxy-5alpha-androstan-17-one;

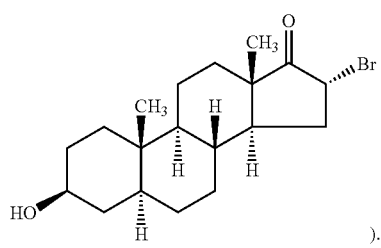

Another embodiment of the present invention comprises administering an E1-E2 peptide of the present invention (e.g., any of SEQ ID NOs: 3-139) in association with RD4-6205

Sudo et al., Biochem. Biophys. Res. Comm. 238: 643-647 (1997)) or any other protease inhibitor disclosed in Sudo et al.

An embodiment of the present invention comprises administering an E1-E2 peptide of the present invention (e.g., any of SEQ ID NOs: 3-139) in association with cerulenin

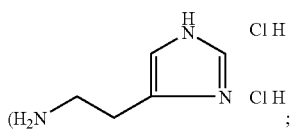

CAS Registry No. 17397-89-6; Lohmann et al., Virology 249: 108-118 (1998)) or any other HCV RNA-dependent RNA polymerase (RdRp) inhibitor disclosed in Lohmann et al.

An embodiment of the present invention comprises administering an E1-E2 peptide of the present invention (e.g., any of SEQ ID NOs: 3-139) in association with ceplene 2-(1H-Imidazol-4-yl)ethanamine dihydrochloride).

An additional embodiment of the present invention comprises administering an E1-E2 peptide of the present invention (e.g., any of SEQ ID NOs: 3-139) in association with

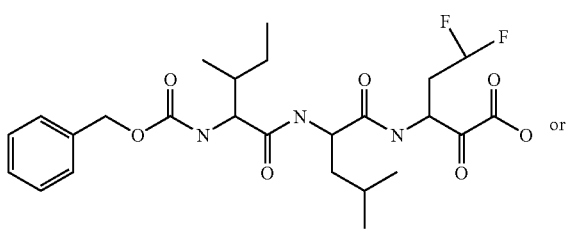

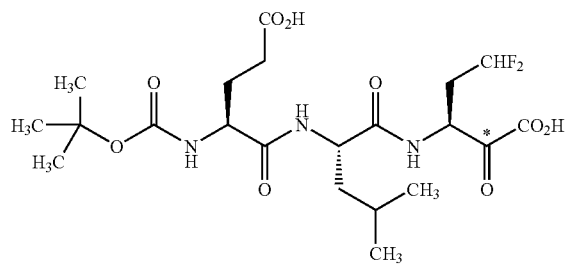

(DiMarco et al., J. Biol. Chem., Vol. 275 (10): 7152-71572000);

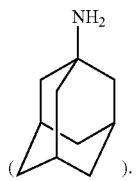

(Barbato et al., EMBO J 19: 1195-1206 (2000)) or any of the NS3/4a protease inhibitors disclosed by Ingallinella et al., Biochemistry, 41(17): 5483-5492 (2002).

Yet another embodiment of the present invention comprises administering an E1-E2 peptide of the present invention (e.g., any of SEQ ID NOs: 3-139) in association with amantadine

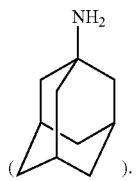

A further embodiment of the present invention comprises administering an E1-E2 peptide of the present invention (e.g., any of SEQ ID NOs: 3-139) in association with IDN-6556

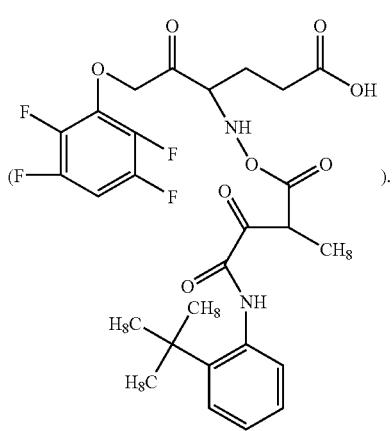

A further embodiment of the present invention comprises administering an E1-E2 peptide of the present invention (e.g., any of SEQ ID NOs: 3-139) in association with beta-Alethine (beta-alanyl-cysteamine disulfide).

Yet another embodiment of the present invention comprises administering an E1-E2 peptide of the present invention (e.g., any of SEQ ID NOs: 3-139) in association with naphthoquinone, 2-methylnaphthoquinone, 2-hydroxynaphthoquinone, 5-hydroxynaphthoquinone, 5,8-dihydroxynaphthoquinone, alkannin or shikonin (Takeshita et al., Analytical Biochem. 247: 242-246 (1997)).

A further embodiment of the present invention comprises administering an E1-E2 peptide of the present invention (e.g., any of SEQ ID NOs: 3-139) in association with 1-amino-1,3,5-trimethylcyclohexane, 1-amino-1 (trans),3(trans),5-trimethylcyclohexane, 1-amino-1(cis),3(cis),5-trimethylcyclohexane, 1-amino-1,3,3,5-tetramethylcyclohexane, 1-amino-1,3,3,5,5-pentamethylcyclohexane, 1-amino-1,3,5,5-tetramethyl-3-ethylcyclohexane, 1-amino-1,5,5-trimethyl-3,3-diethylcyclohexane, 1-amino-1,5,5-trimethyl-cis-3-ethylcyclohexane, 1-amino-(1S,5S)cis-3-ethyl-1,5,5-trimethylcyclohexane, 1-amino-1,5,5-trimethyl-trans-3-ethylcyclohexane, 1-amino-(1R,5S)trans-3-ethyl-1,5,5-trimethylcyclohexane, 1-amino-1-ethyl-3,3,5,5-tetramethylcyclohexane, 1-amino-1-propyl-3,3,5,5-tetramethylcyclohexane, N-methyl-1-amino-1,3,3,5,5-pentamethylcyclohexane, N-ethyl-1-amino-1,3,3,5,5-pentamethylcyclohexane, or N-(1,3,3,5,5-pentamethylcyclohexyl) pyrrolidine or any other 1-aminoalkylcyclohexane N-methyl-D-aspartate (NMDA) inhibitors disclosed in U.S. Pat. No. 6,034,134.

A further embodiment of the present invention comprises administering an E1-E2 peptide of the present invention (e.g., any of SEQ ID NOs: 3-139) in association with d-α-tocopherol or any other anti-HCV compound disclosed in U.S. Pat. No. 5,922,757.

Another embodiment of the present invention comprises administering an E1-E2 peptide of the present invention (e.g., any of SEQ ID NOs: 3-139) in association with tauroursodeoxycholic acid, chenodeoxycholic acid, ursodeoxycholic acid

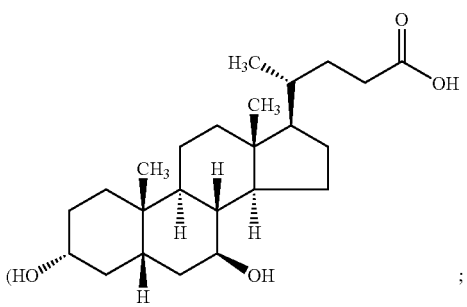

ursodiol) or free bile acid or any other bile acid HCV inhibitor disclosed in U.S. Pat. No. 5,846,964.

A further embodiment of the present invention comprises administering an E1-E2 peptide of the present invention (e.g., any of SEQ ID NOs: 3-139) in association with interleukin 23 (IL-23) or IL-27 (Matsui et al., J. Virol. 78(17):9093-104 (2004)).

Another embodiment of the present invention comprises administering an E1-E2 peptide of the present invention (e.g., any of SEQ ID NOs: 3-139) in association with 1,1'-[1,4-phenylenebis (methylene)]bis(4,4'-trans-(4,5,6,7,8,9-hexahydro) benzimidazoyl)piperidine, 1,1'-[1,4-phenylenebis(methylene)]bis(4,4'-benzimidazoyl) piperidine or any other anti-HCV compound disclosed in U.S. Pat. No. 5,830,905.

Another embodiment of the present invention comprises administering an E1-E2 peptide of the present invention (e.g., any of SEQ ID NOs: 3-139) in association with N,N'-4-[(2-benzimidazole)phenyl]-1,4-butanedicarboxamide, N,N'-4-[(2-benzimidazole)phenyl]-1,6-hexanedicarboxamide, N,N'-4-[(2-benzimidazole)phenyl]-1,8-octanedicarboxamide, N,N'-4-[(2-benzimidazole)phenyl]-1,9-nonanedicarboxamide, N,N'-4-[(2-benzimidazole)phenyl]-1,10-decanedicarboxamide or N,N'-4-[(2-benzimidazole)phenyl]-1,4-butenedicarboxamide or any other carboxamide HCV inhibitor disclosed in U.S. Pat. No. 5,633,388.

Another embodiment of the present invention comprises administering an E1-E2 peptide of the present invention (e.g., any of SEQ ID NOs: 3-139) in association with any of the polyadenylic acid (5') derivatives disclosed in U.S. Pat. No. 5,496,546.

A further embodiment of the present invention comprises administering an E1-E2 peptide of the present invention (e.g., any of SEQ ID NOs: 3-139) in association with 2',3'-dideoxyinosine (U.S. Pat. No. 5,026,687).

An embodiment of the present invention comprises administering an E1-E2 peptide of the present invention (e.g., any of SEQ ID NOs: 3-139) in association with

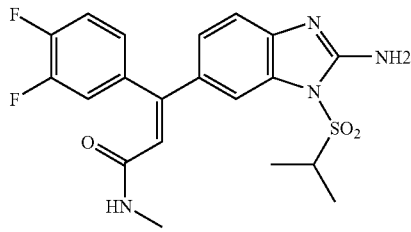

or any other benzimidazole disclosed in U.S. Pat. No. 5,891,874.

An additional embodiment of the invention comprises administering VX-950

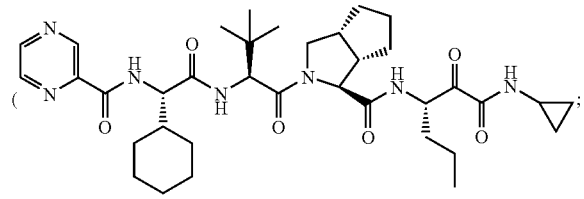

Lin et al., J. Biol. Chem. 279(17): 17508-17514 (2004)) in association with an E1-E2 peptide of the present invention (e.g., any of SEQ ID NOs: 3-139).

Another embodiment of the present invention comprises administering an E1-E2 peptide of the present invention (e.g., any of SEQ ID NOs: 3-139) in association with viramidine

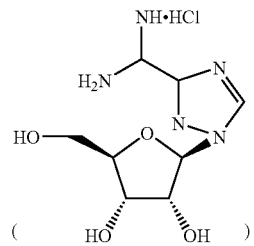

or levovirin

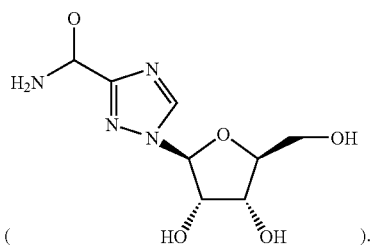

A further embodiment of the invention inclues adminstering an E1-E2 peptide of the invention (e.g., any of SEQ ID NOs: 3-139) in association with IDB-1016 (4H-1-Benzopyran-4-one, 2-(2,3-dihydro-3-(4-hydroxy-3-methoxyphenyl)-2-(hydroxymethyl)-1,4-benzodioxin-6-yl)-2,3-dihydro-3,5,7-trihydroxy-, (2R-(2alpha,3beta,6(2R*,3R*)))-, mixt. with soya phosphatidylcholines; CAS No. 134499-06-2).

Another embodiment of the present invention comprises administering an E1-E2 peptide of the present invention (e.g., any of SEQ ID NOs: 3-139) in association with the anti-sense polynucleotide ISIS-14803 (d(P-thio)(G-T-G-m5C-T-m5C-A-T-G-G-T-G-m5C-A-m5C-G-G-T-m5C-T) DNA).

Yet another embodiment of the present invention comprises administering an E1-E2 peptide of the present invention (e.g., any of SEQ ID NOs: 3-139) in association with any of the E2/CD81 binding inhibitors disclosed in VanCompernolle et al. (Virology 314: 371-380 (2003)), particularly compound 5 or 7 therein.

Moreover, in an embodiment of the invention, an E1-E2 peptide of the invention (e.g., any of SEQ ID NOs: 3-139) is administered in association with an anti-CD81 antibody (e.g., an anti-human CD81 antibody). Anti-CD81 antibodies are available commercially from several sources and can be made by any practitioner of ordinary skill in the art using conventionally known techniques. For example, BD Biosciences (San Jose, Calif.) sells an anti-human CD81 antibody (see also Oren, et al., Mol. Cell. Biol. 10: 4007 (1990); Bradbury, et al., J. Immunol. 149: 2841 (1992) or Schick, et al., J. Immunol. 151:4090 (1993)). The present invention includes embodiments wherein an E1-E2 peptide of the invention (e.g., any of SEQ ID NOs: 3-139) is administered in association with an anti-human CD81 antibody or a fragment thereof, preferably an antigen-binding fragment, thereof; including monoclonal antibodies, polyclonal antibodies, bispecific antibodies, Fab antibody fragments, F(ab)$_2$ antibody fragments, Fv antibody fragments (e.g., VH or VL), single chain Fv antibody fragments and dsFv antibody fragments. Furthermore, the antibodies of the invention may be fully human antibodies or chimeric antibodies. Preferably, the anti-CD81 antibody is a monoclonal, fully human antibody.

Combinations of the invention include an E1-E2 peptide of the present invention (e.g., any of SEQ ID NOs: 3-139) "in association" with one or more (e.g., 2, 3, 4, 5) additional anti-viral agents (e.g., ribavirin, interferon alfa-2a or 2b, or pegylated interferon alfa-2a or 2b). The term "in association" indicates that the components of the combinations of the invention can be formulated into a single composition for simultaneous delivery or formulated separately into two or more compositions (e.g., a kit). Furthermore, each component of a combination of the invention can be administered to a subject at a different time than when the other component is administered; for example, each administration may be given non-simultaneously (e.g., separately or sequentially) at several intervals over a given period of time. Moreover, the separate components may be administered to a subject by the same or by a different route (e.g., orally, intravenously, subcutaneously).

The present invention further comprises compositions comprising an E1-E2 peptide of the present invention (e.g., SEQ ID NOs: 3-139) in combination or in association with one or more anti-viral agents discussed above (e.g., pegylated interferon alfa-2a or 2b or ribavirin) along with pharmaceutical compositions thereof.

In addition, the present invention comprises compositions and methods for treating HCV infection in hosts that are co-infected with HIV. Accordingly, the present invention comprises compositions (e.g., kits) comprising an E1-E2 peptide of the invention (e.g., any of SEQ ID NO: 3-139) in association with one or more HIV protease inhibitors, various nucleoside analogs, nonnucleoside reverse transcriptase inhibitors, antivirals, immunomodulators, antiinfectives, tat antagonists, and glycosidase inhibitors. Numerous examples of such anti-HIV agents are set forth in U.S. Pat. Nos. 6,100,277 and 6,245,806, both incorporated herein by reference, and include, but are not limited to, Ro 31-859, KNI-272, AZT, DDI, DDC, 3TC, D4T, PMEA, Ro 5-3335, Ro 24-7429, indinavir, ritonavir, saquinavir, nelfinavir, amprenavir, abacavir, castanospremine, castanospermine 6-butryl ester, N-butyl-1-deoxy-nojirimycin, N-butyl-1-deoxynojirimycin per-butryl ester, 097, acemannan, acyclovir, AD-439, AD-519, adefovir clipivoxil, AL-721, alpha interferon, ansamycin, beta-fluoro-ddA, BMS-232623, BMS-234475, CI-1012, cidofovir, delaviridine, EL-10, efaviren, famciclovir, FTC, hypericin, Compound Q, ISIS 2922, lobucavir, nevirapine, novapren, peptide T, octapeptide, PNU-140690, probacol, stavudine, valaciclovir, virazole, zalcitabine, ABT-378, bropirimine, gamma interferon, interleukin-2, TNF, etanercept, infliximab, fluconalzole, piritrexim, trimetrexate, daunorubicin, leukotriene B4 receptor antagonist, and analogs and prodrugs thereof. Methods for treating HCV in a patient co-infected with HIV comprising administering an E1-E2 peptide of the invention (e.g., any of SEQ ID NOs: 3-139) in association with an anti-HIV agent (e.g., as discussed herein) are also part of the present invention.

Kits

Kits of the present invention include an E1-E2 peptide of the present invention (e.g., any of SEQ ID NOs: 3-139), preferably combined with a pharmaceutically acceptable carrier, in a pharmaceutical formulation, more preferably in a pharmaceutical dosage form such as a pill, a powder, an injectable liquid, a tablet, dispersible granules, a capsule, a cachet or a suppository. See for example, Gilman et al. (eds.) (1990), *The Pharmacological Bases of Therapeutics*, 8th Ed., Pergamon Press; and *Remington's Pharmaceutical Sciences*, supra, Easton, Pa.; Avis et al. (eds.) (1993) *Pharmaceutical Dosage Forms: Parenteral Medications* Dekker, New York; Lieberman et al. (eds.) (1990) *Pharmaceutical Dosage Forms: Tablets* Dekker, New York; and Lieberman et al. (eds.) (1990), *Pharmaceutical Dosage Forms: Disperse Systems* Dekker, New York. In an embodiment of the invention, a kit of the invention also includes one or more other anti-viral agents, for example, any of the substances discussed above (e.g., ribavirin, pegylated interferon alfa-2a, pegylated interferon alfa-2b or an anti-HIV agent).

A kit of the invention can also include a package insert. The package insert may include information concerning the pharmaceutical compositions and dosage forms in the kit. Generally, such information aids patients and physicians in using the enclosed pharmaceutical compositions and dosage forms effectively and safely. For example, the following information regarding an E1-E2 peptide of the invention or other anti-viral agent, included in the kit, may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references and patent information.

The E1-E2 peptide of the invention (e.g., SEQ ID NOs: 3-139) and the other anti-viral agent can be supplied, in the kit, as separate compositions or combined into a single composition. For example, the compositions can be supplied within a single, common pharmaceutical dosage form (e.g., pill or tablet) as in separate pharmaceutical dosage forms (e.g., two separate pills or tablets).

Dosage and Administration

Pharmaceutical composition of the invention may be administered, for example, by any parenteral (e.g., subcutaneous injection, intramuscular injection, intravenous injection) or non-parenteral route (e.g., orally, nasally).

Pills and capsules of the invention can be administered orally. Injectable compositions can be administered with medical devices known in the art; for example, by injection with a hypodermic needle including the REDIPEN® or the NOVOLET® Novo Pen discussed above.

Injectable pharmaceutical compositions of the invention can also be administered with a needleless hypodermic injection device; such as the devices disclosed in U.S. Pat. Nos. 5,399,163; 5,383,851; 5,312,335; 5,064,413; 4,941,880; 4,790,824 or 4,596,556.

Peptides of the invention can be administered, for example, three times a day, twice a day, once a day, three times weekly, twice weekly or once weekly.

The daily dose of an anti-viral agent administered in association with a peptide of the present invention (e.g., any of SEQ ID NOs: 3-139) is, where possible, administered accordance with the *Physicians' Desk Reference* 2003 (Physicians' Desk Reference, 57th Ed); Medical Economics Company; ISBN: 1563634457; 57th edition (November 2002). The proper dosage can, however, be altered by a clinician to compensate for particular characteristics of the subject receiving the therapy depending, for example, on the potency of the compound administered, side-effects, age, weight, medical condition, overall health and response.

The term "therapeutically effective amount" means that amount of a therapeutic agent or substance (e.g., peptide of the present invention (e.g., any of SEQ ID NOs: 3-139), interferon or ribavirin) that will elicit a biological or medical response of a tissue, system, subject or host that is being sought by the administrator (such as a researcher, doctor or veterinarian) which includes alleviation of the symptoms of Flaviviridae virus (e.g., HCV) infection and the prevention, slowing or halting of progression of Flaviviridae virus (e.g., HCV) infection and its symptom(s) to any degree including prevention of the infection of a host with a Flaviviridae virus (e.g., HCV) following transplant of a liver into said host. For example, in one embodiment, a "therapeutically effective dosage" of an E1-E2 peptide of the present invention (e.g., SEQ ID NOs: 3-139) or a combination including another anti-viral agent (e.g., ribavirin and/or pegylated or unpegylated interferon alfa-2a or 2b) results in the eradication of detectable Flaviviridae Viral RNA (e.g., HCV RNA) for any period of time, for example, 12 or more weeks (e.g., 24 weeks). Detection of viral RNA in a host can be done easily using conventional, well-known methods in the art. See also the Physicians' Desk Reference ("PDR") for the therapeutically effective dose and dosage regimens approved by the U.S. Food and Drug Administration.

A person suffering from chronic hepatitis C infection may exhibit one or more of the following signs or symptoms:
(a) elevated ALT,
(b) positive test for anti-HCV antibodies,
(c) presence of HCV as demonstrated by a positive test for HCV-RNA,
(d) clinical stigmata of chronic liver disease,
(e) hepatocelluar damage.

Ideally, though not necessarily, an infected host who is administered a composition of the invention will, eventually, exhibit no detectable HCV RNA is his body for a period of time (e.g., 12 or more weeks).

The term "no detectable HCV-RNA" in the context of the present invention means that there is less than about 100 copies of HCV-RNA per ml of serum of the patient as measured by quantitative, multi-cycle reverse transcriptase PCR (rtPCT) methodology. Such PCR based assays are conventional and very well known in the art. In general, rtPCR is performed by isolating the RNA from a specimen, reverse-transcribing it to generate cDNAs, amplifying specific nucleic acid sequences by PCR, and then using a variety of methods to detect the amplified sequences (Urdea et al., Clin. Chem. 43:1507-1511 (1997)). Preferably, a patient with no detectable HCV-RNA comprises 0 copies per ml of serum.

In one embodiment, a host administered a composition of the present invention exhibits a sustained virologic response. The term "sustained virologic response" as used in the context of the present invention means that there is no detectable HCV-RNA in the serum of patients treated in accordance with the present invention for at least 24 weeks after the end of the combined therapy treatment. Preferably, the period of sustained virologic response is at least one year—or longer—after the end of treatment.

A "therapeutically effective" dosage or amount of an E1-E2 peptide of the present invention (e.g., SEQ ID NOs: 3-139; e.g., for treating or preventing Flaviviridae virus (e.g., HCV) infection) is about 100 µg three times per day or about 300 µg once a day. However, as discussed above, this dosage may be adjusted up or down by a clinician depending on the circumstances of each particular case.

As discussed herein, methods of the present invention include administering an E1-E2 peptide of the present invention (e.g., any of SEQ ID NOs: 3-139) along with pegylated or unpegylated interferon alfa-2a, pegylated or unpegylated interferon alfa-2b, pegylated or unpegylated interferon alfa-2c, pegylated or unpegylated interferon alfa n-1, pegylated or unpegylated interferon alfa n-3, unpegylated pegylated consensus interferon, ribavirin or any combination thereof.

A therapeutically effective dosage of interferon alfa-2b (e.g., INTRON-A®), particularly for the treatment of chronic hepatitis C is 3 million IU (international units) three times a week (TIW) administered subcutaneously or intramuscularly. In patients tolerating therapy with normalization of serum alanine aminotransferase (ALT) at 16 weeks of treatment, INTRON A® therapy should be extended to 18 to 24 months (72 to 96 weeks) at 3 million IU TIW to improve the sustained response rate.

If severe adverse reactions develop during INTRON A® treatment, the dose should be modified (50% reduction) or therapy should be discontinued as indicated below. If intolerance persists after dose adjustment, INTRON A® therapy should be discontinued.

The recommended dose of PEG-interferon alfa-2b (e.g., PEG-INTRON®) regimen is from about 0.5 to about 1.5 µg/kg/week, preferably 1.0 µg/kg/week for one year.

A therapeutically effective dosage of interferon alfa-2a (e.g., ROFERON-A®), particularly for the treatment of chronic hepatitis C, is 3 MIU three times a week (TIW) administered subcutaneously or intramuscularly for 12 months (48 to 52 weeks). As an alternative, patients may be treated with an induction dose of 6 MIU TIW for the first 3 months (12 weeks) followed by 3 MIU TIW for 9 months (36 weeks).

Patients who tolerate and partially or completely respond to therapy with ROFERON-A® but relapse following its discontinuation may be re-treated. Re-treatment with either 3 MIU TIW or with 6 MIU TIW for 6 to 12 months may be considered.

A temporary dose reduction by 50% is recommended in patients who do not tolerate the prescribed dose of ROFERON-A®. If adverse events resolve, treatment with the original prescribed dose can be re-initiated. In patients who cannot tolerate the reduced dose, cessation of therapy, at least temporarily, is recommended.

The recommended dose of PEG-interferon alfa-2a (e.g., PEGASYS®) monotherapy is 180 µg (1.0 mL) once weekly for 48 weeks by subcutaneous (SC) administration in the abdomen or thigh.

A therapeutically effective dosage of consensus interferon alfa (e.g., INFERGEN®), particularly for treatment of chronic HCV infection, is 9 mcg TIW administered SC as a single injection for 24 weeks. At least 48 hours should elapse between doses of INFERGEN®.

Patients who tolerated previous interferon therapy and did not respond or relapsed following its discontinuation may be subsequently treated with 15 mcg of INFERGEN® TIW administered SC as a single injection for up to 48 weeks.

For patients who experience a severe adverse reaction on INFERGEN®, dosage should be withheld temporarily. If the adverse reaction does not become tolerable, therapy should be discontinued. Dose reduction to 7.5 mcg may be necessary following an intolerable adverse event.

If adverse reactions continue to occur at the reduced dosage, the physician may discontinue treatment or reduce dosage further. However, decreased efficacy may result from continued treatment at dosages below 7.5 mcg.

During subsequent treatment for 48 weeks with 15 mcg of INFERGEN®, up to 36% of patients required dose reductions in 3 mcg increments.

A therapeutically effective does of albumin-interferon-alpha (e.g., ALBUFERON®) is about 120 mcg or about 180 mcg or about 240 mcg or about 320 mcg or about 400 mcg or about 500 mcg per day subcutaneously.

A therapeutically effective dose of ribavirin (e.g., REBETROL®) depends on the patient's body weight. The recommended dose of REBETOL® is provided, below, in Table 1.

TABLE 1

Recommended Dosing

| Body weight | REBETOL Capsules |
|---|---|
| </=75 kg | 2 × 200-mg capsules AM, 3 × 200-mg capsules PM daily p.o. |
| >75 kg | 3 × 200 mg capsules AM, 3 × 200 mg capsules PM daily p.o. |

The recommended duration of treatment with ribavirin (e.g., REBETOL®) for patients previously untreated with interferon is 24 to 48 weeks. The duration of treatment should be individualized to the patient depending on baseline disease characteristics, response to therapy, and tolerability of the regimen. After 24 weeks of treatment, virologic response should be assessed. Treatment discontinuation should be considered in any patient who has not achieved an HCV RNA below the limit of detection of the assay by 24 weeks.

In patients who relapse following interferon therapy, the recommended duration of treatment with ribavirin (e.g., REBETOL®) is 24 weeks.

REBETOL® may be administered without regard to food, but should be administered in a consistent manner with respect to food intake.

A combination of interferon alfa-2b and ribavirin (e.g., REBETRON®) can also be administered in association with an E1-E2 peptide of the present invention (e.g., SEQ ID NOs: 3-139).

The recommended duration of REBETRON® treatment for patients previously untreated with interferon is 24 to 48 weeks. The duration of treatment should be individualized to the patient depending on baseline disease characteristics, response to therapy, and tolerability of the regimen. After 24 weeks of treatment, virologic response should be assessed. Treatment discontinuation should be considered in any patient who has not achieved an HCV RNA below the limit of detection of the assay by 24 weeks. In patients who relapse following interferon therapy, the recommended duration of treatment is 24 weeks.

The recommended dosage of a combination of ribavirin (e.g., REBETROL®) and interferon alfa-2b (e.g., INTRON-A®) depends on patient body weigh. The adult dosage regimen is set forth below in Table 2:

TABLE 2

Recommended Adult Dosing

| Body weight | REBETOL Capsules | INTRON A Injection |
|---|---|---|
| </=75 kg | 2 × 200-mg capsules AM, 3 × 200-mg capsules PM daily p.o. | 3 million IU 3 times weekly s.c. |
| >75 kg | 3 × 200-mg capsules AM, 3 × 200-mg capsules PM daily p.o. | 3 million IU 3 times weekly s.c. |

The pediatric dosage regimen, for the combination, is set forth below in Table 3:

TABLE 3

Pediatric Dosing

| Body weight | REBETOL Capsules | INTRON A Injection |
|---|---|---|
| 25-36 kg | 1 × 200-mg capsule AM, 1 × 200-mg capsule PM daily p.o. | 3 million IU/m$^2$ 3 times weekly s.c. |
| 37-49 kg | 1 × 200-mg capsule AM, 2 × 200-mg capsules PM daily p.o. | 3 million IU/m$^2$ 3 times weekly s.c. |
| 50-61 kg | 2 × 200-mg capsules AM, 2 × 200-mg capsules PM daily p.o. | 3 million IU/m$^2$ 3 times weekly s.c. |
| >61 kg | Refer to adult dosing table | Refer to adult dosing table |

Dosage modification of REBETOL®/INTRON-A® treatment is indicated when adverse reactions are observed in the patient. For example, in patients with a history of stable cardiovascular disease, a permanent dose reduction is required if the patient's hemoglobin decreases by >/=2 g/dL during any 4-week period. In addition, for these cardiac history patients, if the patient's hemoglobin remains <12 g/dL after 4 weeks on a reduced dose, the patient should discontinue combination REBETOL®/INTRON-A® therapy.

It is recommended that a patient whose hemoglobin level falls below 10 g/dL have his/her REBETOL® dose reduced to 600 mg daily (1×200-mg capsule AM, 2×200-mg capsules PM). A patient whose hemoglobin level falls below 8.5 g/dL should be permanently discontinued from REBETOL®/INTRON A® therapy.

When administered in combination with REBETOL®, the recommended dose of PEG-Intron® is 1.5 micrograms/kg/week. The recommended dose of REBETOL® is 800 mg/day in 2 divided doses: two capsules (400 mg) with breakfast and two capsules (400 mg) with dinner. REBETOL® should not be used in patients with creatinine clearance <50 mL/min.

EXAMPLES

The following examples are intended to exemplify and further clarify what is the present invention and should not be construed to limit the present invention. The present invention should not be limited by any mechanism or theory presented herein. Any composition disclosed in any of the following examples along with any disclosed method is part of the present invention.

Example 1

Identification and Characterization of Inhibitory E1-E2 Peptides

Expression of HCV envelope protein. The envelope region of HCV was PCR amplified from FKI389/core3' plasmid (Pietschmann et al., J. Virol. 76(8):4008-21 (2002)) with the primers GATCAAGCTTATGGGTTGCTCCTTTTC-TATCTTC (SEQ ID NO: 140) and GATCAGATCTAGT-GATAATCCGGAGTCGAACTCGATAGTC (SEQ ID NO: 141). The amplified product was digested with HindIII and XbaI and ligated into the pCMV-hygro (Invitrogen Corp.; Carlsbad, Calif.). The expression of the envelope proteins was confirmed with Western blot.

HCV pseudotype particle generation. Single cycle HCV pseudoparticles are composed of a replication-defective HIV genome and HCV envelope proteins. These pseudoparticles were made by transfecting 293T cells with 5 ug of each pNL43E-R-luc (Chen et al., J Virol. 68(2):654-60 (1994)) and plasmid expressing HCV envelope proteins pCMV/E1-2 with profection transfection kit from Promega (Madison, Wis.). The medium was refreshed 12-24 hours after transfection and supernatant was collected 48 hours after transfection. The supernatant from a transfection of only pNL43E-R-luc was used each time as a control for non specific entry events.

Peptide library preparation. The peptide library was synthetically assembled on MBHA Rink amide or NovaSyn TG Sieber resin (at 5 mmol per peptide) in 96-well microtiter plate by a MultiPep synthesizer (Intavis AG, Germany) with standard Fmoc chemistry. After successful completion of the synthesis, the resins were washed with dichloromethane five times and completely dried under vacuum in the MultiPep. The microtiter plate was removed from the MultiPep and placed on top of a 96-well collection plate (2 ml volume per well). 200 ul of concentrated (80-90%) TFA with proper scavengers such as water and triisopropylsilane were added to the microtiter wells containing the assembled peptide resin. This cleavage process was repeated three additional times with 10 min intervals. The collected cleavage solution was let to stand at room temperature for 2 hours of deprotection. Each peptide was then transferred to a 15-ml polypropylene tube containing 10 ml anhydrous ethyl ether. The tubes were spun down in a clinical centrifuge. The ether phase was carefully decanted. The precipitated peptides were taken up in water and lyophilized over night. LCMS analysis was conducted for each peptide to verify the molecular weight and assess purity. The peptides were finally dissolved in 100% DMSO and used in assays without further purification unless otherwise noted for selected bioactive peptides. Occasionally, the bioactive peptides were synthesized at larger scale (250 umol) by an ABI model 431A peptide synthesizer (Applied Biosystems, Foster City, Calif.) using the same chemistry as mentioned above.

Infection of hepatoma cell lines with HCV pseudotype particles and screen for inhibitory peptides. The hepatoma cells, Huh7, was seeded at 8000 cells in 90 ul medium in 96-well plate. In the case of the inhibitor screen, the inhibitor was incubated with cells for one hour at 37° C. and then 50 ul viral supernatant was added to the cells 24 hours after seeding. The viral stock was pre-tittered and diluted to yield approximately 10,000 to 20,000 RLU. The cells were incubated at 37° C. with 5% $CO_2$ for additional 72 hours and were harvested for luciferase assay. Peptide stocks were prepared in 100% DMSO at 10 mg/ml and were first screened at 100 ug/ml and then a dose responsive curve was generated with 10 points 3-fold titration starting from 100 ug/ml.

The specificity of the peptides were counter-screened with AMLV and HIV pseudotyped viruses using the same infection protocol. The results of the entry assay, corresponding to the peptides tested, are shown below in Table 4.

Results.

TABLE 4

Screen of the peptide library.

| Peptides | HCVpp % inh | AMLVpp % inh |
|---|---|---|
| Y-E-V-R-N-V-S-G-V-Y-H-V-T-N-D-C (SEQ ID NO:3) | 35 | 18 |
| G-V-Y-H-V-T-N-D-C-S-N-A-S-I-V-Y (SEQ ID NO:4) | -23 | -6 |
| D-C-S-N-A-S-I-V-Y-E-A-A-D-M-I-M (SEQ ID NO:5) | -4 | -2 |
| V-Y-E-A-A-D-M-I-M-H-T-P-G-C-V-P (SEQ ID NO:6) | -13 | 10 |
| I-M-H-T-P-G-C-V-P-C-V-R-E-N-N-S (SEQ ID NO:7) | 3 | -4 |
| V-P-C-V-R-E-N-N-S-S-R-C-W-V-A-L (SEQ ID NO:8) | -22 | 14 |
| N-S-S-R-C-W-V-A-L-T-P-T-L-A-A-R (SEQ ID NO:9) | 5 | 28 |
| A-L-T-P-T-L-A-A-R-N-A-S-V-P-T-T (SEQ ID NO:10) | 53 | 1 |
| A-R-N-A-S-V-P-T-T-T-I-R-R-H-V-D (SEQ ID NO:11) | -26 | 24 |
| T-T-T-I-R-R-H-V-D-L-L-V-G-A-A-A (SEQ ID NO:12) | 31 | -5 |
| V-D-L-L-V-G-A-A-A-L-C-S-A-M-Y-V (SEQ ID NO:13) | 39 | -13 |
| A-A-L-C-S-A-M-Y-V-G-D-L-C-G-S-V (SEQ ID NO:14) | 39 | -42 |
| Y-V-G-D-L-C-G-S-V-F-L-V-A-Q-L-F (SEQ ID NO:15) | 16 | -31 |
| S-V-F-L-V-A-Q-L-F-T-F-S-P-R-R-H (SEQ ID NO:16) | 3 | -148 |
| L-F-T-F-S-P-R-R-H-E-T-V-Q-D-C-N (SEQ ID NO:17) | 9 | 16 |
| R-H-E-T-V-Q-D-C-N-C-S-I-Y-P-G-H (SEQ ID NO:18) | 5 | 17 |
| C-N-C-S-I-Y-P-G-H-V-T-G-H-R-M-A (SEQ ID NO:19) | 49 | 26 |
| G-H-V-T-G-H-R-M-A-W-D-M-M-M-N-W (SEQ ID NO:20) | 43 | 6 |
| M-A-W-D-M-M-M-N-W-S-P-T-A-A-L-V (SEQ ID NO:21) | 32 | 3 |
| N-W-S-P-T-A-A-L-V-V-S-Q-L-L-R-I (SEQ ID NO:22) | 54 | -11 |

TABLE 4-continued

Screen of the peptide library.

| Peptides | HCVpp % inh | AMLVpp % inh |
|---|---|---|
| L-V-V-S-Q-L-L-R-I-P-Q-A-V-V-D-M (SEQ ID NO:23) | 3 | -1 |
| R-I-P-Q-A-V-V-D-M-V-A-G-A-H-W-G (SEQ ID NO:24) | 25 | -2 |
| D-M-V-A-G-A-H-W-G-V-L-A-G-L-A-Y (SEQ ID NO:25) | 27 | 14 |
| W-G-V-L-A-G-L-A-Y-Y-S-M-V-G-N-W (SEQ ID NO:26) | 50 | 27 |
| A-Y-Y-S-M-V-G-N-W-A-K-V-L-I-V-M (SEQ ID NO:27) | 39 | -2 |
| N-W-A-K-V-L-I-V-M-L-L-F-A-G-V-D (SEQ ID NO:28) | 13 | -1 |
| V-M-L-L-F-A-G-V-D-G-G-T-Y-V-T-G (SEQ ID NO:29) | -22 | 11 |
| V-D-G-G-T-Y-V-T-G-G-T-M-A-K-N-T (SEQ ID NO:30) | 2 | -9 |
| T-G-G-T-M-A-K-N-T-L-G-I-T-S-L-F (SEQ ID NO:31) | 41 | -2 |
| N-T-L-G-I-T-S-L-F-S-P-G-S-S-Q-K (SEQ ID NO:32) | 11 | 2 |
| L-F-S-P-G-S-S-Q-K-I-Q-L-V-N-T-N (SEQ ID NO:33) | 61 | -49 |
| Q-K-I-Q-L-V-N-T-N-G-S-W-H-I-N-R (SEQ ID NO:34) | 6 | 13 |
| T-N-G-S-W-H-I-N-R-T-A-L-N-C-N-D (SEQ ID NO:35) | 29 | 30 |
| N-R-T-A-L-N-C-N-D-S-L-N-T-G-F-L (SEQ ID NO:36) | 23 | 18 |
| N-D-S-L-N-T-G-F-L-A-A-L-F-Y-V-H (SEQ ID NO:37) | 14 | 15 |
| F-L-A-A-L-F-Y-V-H-K-F-N-S-S-G-C (SEQ ID NO:38) | 23 | -44 |
| V-H-K-F-N-S-S-G-C-P-E-R-M-A-S-C (SEQ ID NO:39) | -11 | -15 |
| G-C-P-E-R-M-A-S-C-S-P-I-D-A-F-A (SEQ ID NO:40) | 35 | -4 |
| S-C-S-P-I-D-A-F-A-Q-G-W-G-P-I-T (SEQ ID NO:41) | -11 | 25 |
| F-A-Q-G-W-G-P-I-T-Y-N-E-S-H-S-S (SEQ ID NO:42) | 49 | 15 |
| I-T-Y-N-E-S-H-S-S-D-Q-R-P-Y-C-W (SEQ ID NO:43) | -13 | 17 |
| S-S-D-Q-R-P-Y-C-W-H-Y-A-P-R-P-C (SEQ ID NO:44) | 14 | 15 |
| C-W-H-Y-A-P-R-P-C-G-I-V-P-A-A-Q (SEQ ID NO:45) | 63 | -8 |
| P-C-G-I-V-P-A-A-Q-V-C-G-P-V-Y-C (SEQ ID NO:46) | 29 | -2 |
| A-Q-V-C-G-P-V-Y-C-F-T-P-S-P-V-V (SEQ ID NO:47) | 40 | -8 |
| Y-C-F-T-P-S-P-V-V-V-G-T-T-D-R-F (SEQ ID NO:48) | 6 | 21 |
| V-V-V-G-T-T-D-R-F-G-V-P-T-Y-S-W (SEQ ID NO:49) | 37 | -22 |
| R-F-G-V-P-T-Y-S-W-G-E-N-E-T-D-V (SEQ ID NO:50) | 34 | 33 |
| S-W-G-E-N-E-T-D-V-L-L-L-N-N-T-R (SEQ ID NO:51) | 23 | 34 |
| D-V-L-L-N-N-T-R-P-P-Q-G-N-W-F (SEQ ID NO:52) | 10 | 16 |
| T-R-P-P-Q-G-N-W-F-G-C-T-W-M-N-S (SEQ ID NO:53) | 59 | -42 |
| W-F-G-C-T-W-M-N-S-T-G-F-T-K-T-C (SEQ ID NO:54) | 39 | -15 |
| N-S-T-G-F-T-K-T-C-G-G-P-P-C-N-I (SEQ ID NO:55) | 23 | 3 |
| T-C-G-G-P-P-C-N-I-G-G-I-G-N-K-T (SEQ ID NO:56) | 53 | 22 |
| N-I-G-G-I-G-N-K-T-L-T-C-P-T-D-C (SEQ ID NO:57) | 39 | 20 |
| K-T-L-T-C-P-T-D-C-F-R-K-H-P-E-A (SEQ ID NO:58) | 50 | 13 |
| D-C-F-R-K-H-P-E-A-T-Y-T-K-C-G-S (SEQ ID NO:59) | 26 | -14 |
| E-A-T-Y-T-K-C-G-S-G-P-W-L-T-P-R (SEQ ID NO:60) | 13 | 17 |

TABLE 4-continued

Screen of the peptide library.

| Peptides | HCVpp % inh[1] | AMLVpp % inh[2] |
|---|---|---|
| G-S-G-P-W-L-T-P-R-C-L-V-H-Y-P-Y (SEQ ID NO:61) | -15 | -8 |
| P-R-C-L-V-H-Y-P-Y-R-L-W-H-Y-P-C (SEQ ID NO:62) | 10 | -42 |
| P-Y-R-L-W-H-Y-P-C-T-V-N-F-T-I-F (SEQ ID NO:63) | 44 | 3 |
| P-C-T-V-N-F-T-I-F-K-V-R-M-Y-V-G (SEQ ID NO:64) | -2 | -30 |
| I-F-K-V-R-M-Y-V-G-G-V-E-H-R-L-E (SEQ ID NO:65) | 19 | -62 |
| V-G-G-V-E-H-R-L-E-A-A-C-N-W-T-R (SEQ ID NO:66) | 22 | 34 |
| L-E-A-A-C-N-W-T-R-G-E-R-C-N-L-E (SEQ ID NO:67) | 26 | 37 |
| T-R-G-E-R-C-N-L-E-D-R-D-R-S-E-L (SEQ ID NO:68) | 13 | -7 |
| L-E-D-R-D-R-S-E-L-S-P-L-L-L-S-T (SEQ ID NO:69) | -15 | 1 |
| E-L-S-P-L-L-L-S-T-T-E-W-Q-V-L-P (SEQ ID NO:70) | 10 | 44 |
| S-T-T-E-W-Q-V-L-P-C-S-F-T-T-L-P (SEQ ID NO:71) | 44 | 18 |
| L-P-C-S-F-T-T-L-P-A-L-S-T-G-L-I (SEQ ID NO:72) | -2 | 20 |
| L-P-A-L-S-T-G-L-I-H-L-H-Q-N-V-V (SEQ ID NO:73) | 19 | 0 |
| L-I-H-L-H-Q-N-V-V-D-V-Q-Y-L-Y-G (SEQ ID NO:74) | 22 | 5 |
| V-V-D-V-Q-Y-L-Y-G-I-G-S-A-V-V-S (SEQ ID NO:75) | 39 | 44 |
| Y-G-I-G-S-A-V-V-S-F-A-I-K-W-E-Y (SEQ ID NO:76) | 7 | 24 |
| V-S-F-A-I-K-W-E-Y-V-L-L-L-F-L-L (SEQ ID NO:77) | 96 | 3 |
| E-Y-V-L-L-L-F-L-L-L-A-D-A-R-V-C (SEQ ID NO:78) | 38 | 34 |
| L-L-L-A-D-A-R-V-C-A-C-L-W-M-M-L (SEQ ID NO:79) | 77 | 16 |
| V-C-A-C-L-W-M-M-L-L-I-A-Q-A-E-A (SEQ ID NO:80) | 16 | 7 |

[1] Percentage of cell entry inhibition of hepatitis C virus observed in the presence of the indicated peptide as compared to the uninhibited control.
[2] Percentage of cell entry inhibition of amphotropic murine leukemia virus observed in the presence of the indicated peptide as compared to the uninhibited control.

The data points for the dose response curve of peptide VSFAIKWEYVLLLFLL (SEQ ID NO: 77) are shown below in tables 5A (HCVpp) and 5B (HIVpp). The peptide of SEQ ID NO: 77 was first serial diluted by the factor of 3 in 100% DMSO from 100 ug/ml and then transferred to the assay plates at 100-fold dilution. The peptide was first incubated with cells and HCVpp (A) or HIVpp (B), respectively, for 30 minutes at 370 C in this experiment. Then, the medium containing the peptide was removed from the cells and virus with peptide was added to the cells. Cells were incubated for 72 hours and then were harvested for luciferase assay. Two separate trials were performed.

TABLE 5A

Dose response curve data points for SEQ ID NO: 77 (HCV).

| Peptide conc. (log ug/ml) | RLU units (1st trial) | RLU units (2nd trial) |
|---|---|---|
| 2 | 11 | 10 |
| 1.522879 | 22 | 67 |
| 1.045758 | 306 | 75 |
| 0.568636 | 544 | 500 |
| 0.091515 | 1044 | 833 |
| -0.38561 | 1279 | 1283 |
| -0.86273 | 1866 | 1762 |
| -1.33985 | 2564 | 2703 |
| -1.33985 | 2998 | 3512 |
| -1.33985 | 2090 | 3359 |
| | 1494 | |

TABLE 5B

Dose response curve data points for SEQ ID NO: 77 (HIV).

| Peptide conc. (log ug/ml) | RLU units (1st trial) | RLU units (2nd trial) |
|---|---|---|
| 2 | 435408 | 543239 |
| 1.522879 | 787025 | 683636 |
| 1.045758 | 740592 | 744482 |
| 0.568636 | 561454 | 612198 |
| 0.091515 | 674698 | 651004 |
| −0.38561 | 732652 | 734586 |
| −0.86273 | 676303 | 639921 |
| −1.33985 | 815312 | 754404 |

In addition, the peptide of SEQ ID NO: 77 was mutated at several positions and assayed in the HCV entry assay discussed above. The peptides generated are shown, below, in table 6 along with the results of the HCV entry assay using each peptide. Generally, the peptide of SEQ ID NO: 77 had its N-terminal three amino acids removed (13-mer) and various residues in the 13-mer were replace with alanine (Ala-scan), lysine (Lys-scan), proline (Pro-scan) or glycine (Gly-scan). The data shown in table 6 indicate the percentage of hepatitis C virus cellular entry, at 30 µM peptide concentration, as compared to the uninhibited control. The assays were performed essentially as described above.

TABLE 6

Screen of mutant peptides.

| Sequence | | Description | % of control at ~30 uM |
|---|---|---|---|
| A-I-K-W-E-Y-V-L-L-L-F-L-L | (SEQ ID NO: 81) | 13-mer | 17 |
| G-I-K-W-E-Y-V-L-L-L-F-L-L | (SEQ ID NO: 82) | Gly-scan | 22 |
| A-G-K-W-E-Y-V-L-L-L-F-L-L | (SEQ ID NO: 83) | Gly-scan | 9 |
| A-I-K-W-G-Y-V-L-L-L-F-L-L | (SEQ ID NO: 84) | Gly-scan | 19 |
| A-I-K-W-E-Y-V-L-L-L-F-L-L | (SEQ ID NO: 81) | 13-mer | 20 |
| A-I-K-W-E-Y-V-L-L-L-F-L-L | (SEQ ID NO: 81) | 13-mer | 13 |
| A-A-K-W-E-Y-V-L-L-L-F-L-L | (SEQ ID NO: 87) | Ala-scan | 14 |
| A-I-A-W-E-Y-V-L-L-L-F-L-L | (SEQ ID NO: 88) | Ala-scan | 9 |
| A-I-K-A-E-Y-V-L-L-L-F-L-L | (SEQ ID NO: 89) | Ala-scan | 8 |
| A-I-K-W-A-Y-V-L-L-L-F-L-L | (SEQ ID NO: 90) | Ala-scan | 13 |
| A-I-K-W-E-A-V-L-L-L-F-L-L | (SEQ ID NO: 91) | Ala-scan | 16 |
| A-I-K-W-E-Y-A-L-L-L-F-L-L | (SEQ ID NO: 92) | Ala-scan | 17 |
| A-I-K-W-E-Y-V-A-L-L-F-L-L | (SEQ ID NO: 93) | Ala-scan | 13 |
| A-I-K-W-E-Y-V-L-A-L-F-L-L | (SEQ ID NO: 94) | Ala-scan | 17 |
| A-I-K-W-E-Y-V-L-L-A-F-L-L | (SEQ ID NO: 95) | Ala-scan | 8 |
| A-I-K-W-E-Y-V-L-L-L-F-A-L | (SEQ ID NO: 96) | Ala-scan | 24 |
| A-I-K-W-E-Y-V-L-L-L-F-L-A | (SEQ ID NO: 97) | Ala-scan | 24 |
| A-I-K-W-E-Y-V-L-L-L-F-L-L | (SEQ ID NO: 81) | 13-mer | 10 |
| P-I-K-W-E-Y-V-L-L-L-F-L-L | (SEQ ID NO: 99) | Pro-scan | 21 |
| A-I-K-W-E-Y-V-L-L-L-F-L-L | (SEQ ID NO: 81) | 13-mer | 6 |
| K-I-K-W-E-Y-V-L-L-L-F-L-L | (SEQ ID NO: 101) | Lys-scan | 4 |
| A-K-K-W-E-Y-V-L-L-L-F-L-L | (SEQ ID NO: 102) | Lys-scan | 5 |
| A-I-K-W-K-Y-V-L-L-L-F-L-L | (SEQ ID NO: 103) | Lys-scan | 1 |

Example 2

The Combinational Effects of an Anti-CD81 Antibody and the Peptide of SEQ ID NO: 77 on HCV Pseudoparticle Entry This example demonstrated that the peptide of SEQ ID NO: 77 can enhance the potency of an anti-CD81 antibody and reduce the amount of anti-CD81 antibody that is needed to achieve HCV entry inhibition. The anti-CD81 antibody and the peptide were titrated in duplicates in a 96-well formatted matrix and tested in an HCV pseudoparticle entry assay. The assays were carried out essentially as described above. The data are shown below in the table 7.

TABLE 7

Results of HCV pseudoparticle entry assay in the presence of the peptide of SEQ ID NO: 77 and an anti-CD81 antibody.

| CD81 antibody ug/ml | | peptide ug/ml | | | | | | | | |
|---|---|---|---|---|---|---|---|---|---|---|
| | | 100 RLU | 100 RLU | 25 RLU | 25 RLU | 6.25 RLU | 6.25 RLU | 1.563 RLU | 1.563 RLU | 0.391 RLU |
| 10 | RLU | 11 | 54 | 9 | 11 | 59 | 8 | 12 | 8 | 11 |
| 1 | RLU | 15 | 1322 | 60 | 97 | 62 | 183 | 82 | 69 | 392 |
| 0.5 | RLU | 425 | 2378 | 465 | 547 | 639 | 379 | 886 | 1421 | 505 |
| 0.25 | RLU | 895 | 2056 | 1329 | 449 | 1716 | 1286 | 1177 | 1863 | 3172 |
| 0.125 | RLU | 2022 | 2646 | 1972 | 1953 | 3028 | 3033 | 5729 | 3990 | 5847 |
| 0.063 | RLU | 2490 | 1686 | 2866 | 3310 | 4473 | 4063 | 6595 | 4999 | 10137 |
| 0.031 | RLU | 3956 | 2902 | 2898 | 4125 | 5178 | 5950 | 7372 | 6792 | 9934 |
| 0.016 | RLU | 3651 | 3704 | 6733 | 3753 | 5114 | 3947 | 10490 | 8055 | 12692 |
| 0.008 | RLU | 3467 | 3174 | 7394 | 5876 | 8317 | 7338 | 7426 | 7750 | 15805 |
| 0.004 | RLU | 5596 | 2937 | 6870 | 4968 | 7406 | 7571 | 13281 | 7992 | 14122 |
| 0.002 | RLU | 3192 | 3875 | 6206 | 5485 | 7305 | 7703 | 10717 | 9978 | 13906 |
| 0.002 | RLU | 2317 | 4082 | 5297 | 5697 | 5277 | 8751 | 11221 | 9543 | 9828 |

| CD81 antibody ug/ml | peptide ug/ml | | | | | | |
|---|---|---|---|---|---|---|---|
| | 0.391 RLU | 0.098 RLU | 0.098 RLU | 0 RLU | 0 RLU | 0 RLU | 0 RLU |
| 10 | 9 | 16 | 7 | 106 | 9 | 85 | 45 |
| 1 | 312 | 298 | 141 | 779 | 303 | 1005 | 470 |
| 0.5 | 1120 | 1402 | 491 | 1608 | 1338 | 1686 | 1356 |
| 0.25 | 1404 | 2168 | 2740 | 6099 | 4330 | 9891 | 5351 |
| 0.125 | 4578 | 3503 | 7501 | 14512 | 9507 | 15468 | 8386 |
| 0.063 | 7624 | 10587 | 9989 | 17164 | 12430 | 16250 | 12146 |
| 0.031 | 8742 | 15376 | 12424 | 16998 | 13731 | 19768 | 16741 |
| 0.016 | 9424 | 15036 | 12663 | 17381 | 17712 | 17123 | 15484 |
| 0.008 | 9670 | 17882 | 13398 | 19216 | 16711 | 23553 | 15269 |
| 0.004 | 13155 | 18445 | 6152 | 18053 | 19403 | 18423 | 16197 |
| 0.002 | 13219 | 20304 | 13319 | 10409 | 14130 | 17576 | 15204 |
| 0.002 | 12349 | 14565 | 17382 | 15086 | 16310 | 13542 | 17922 |

RLU = luciferase units (relative light units).

Dose response curves of anti-CD81 antibody with various amounts of peptide were plotted vs. RLU, and the results are summarized below. The data indicate that the concentrations for anti-CD81 antibody to achieve 50% and 90% inhibition were decreased in the presence of the increasing amount of the peptide. When the peptide was present at 10-30% of its IC50 concentration, the IC50 for anti-CD81 was reduced by 3 to 6-fold. Similarly, when the peptide was present at 1% to 25% of its IC75 concentration, the IC75 for the anti-CD81 antibody was reduced by 3 to 9 fold. Thus, the peptide enhances the potency of the anti-CD81 antibody.

TABLE 8

IC50 and IC90 of the anti-CD81 antibody in the presence of increasing concentrations of peptide of SEQ ID NO: 77.

| CD81 + pp75 ug/ml | IC50 | IC90 |
|---|---|---|
| 0.000 | 0.214 | 0.639 |
| 0.000 | 0.189 | 0.482 |
| 0.098 | 0.090 | 0.319 |
| 0.391 | 0.063 | 0.378 |
| 1.563 | 0.024 | 0.371 |
| 6.250 | | 0.253 |
| 25.000 | | 0.139 |
| 100.000 | | 0.266 |

Example 3

Amino Acid Sequence Requirement for Peptide Activity

To determine which amino acids are required to inhibit HCVpp entry, sequential deletions were generated at the amino and carboxy terminus of the peptide of SEQ ID NO: 77 (Table 9). Sequential deletion of the first six amino acids from the amino terminus retained 80 to 90% of inhibition activity; however, a series removal of the six amino acids from the carboxy terminus lost approximately 50% activity. The sensitivity to the carboxy terminus deletions indicates the importance of the residues from the transmembrane domain. The peptide, A-I-K-W-E-Y-V-L-L-L-F-L-L (SEQ ID NO: 81), retained about 90% activity and is three amino acids shorter than the peptide of SEQ ID NO: 77.

TABLE 9

Truncated peptides.°

| Peptides | Comments | HCVpp % inh | |
|---|---|---|---|
| V-S-F-A-I-K-W-E-Y-V-L-L-L-F-L-L | wild type | | (SEQ ID NO: 77) |
| S-F-A-I-K-W-E-Y-V-L-L-L-F-L-L | N-terminal truncation | 91 | (SEQ ID NO: 104) |
| F-A-I-K-W-E-Y-V-L-L-L-F-L-L | N-terminal truncation | 95 | (SEQ ID NO: 105) |
| A-I-K-W-E-Y-V-L-L-L-F-L-L | N-terminal truncation | 92 | (SEQ ID NO: 81) |
| I-K-W-E-Y-V-L-L-L-F-L-L | N-terminal truncation | 88 | (SEQ ID NO: 107) |
| K-W-E-Y-V-L-L-L-F-L-L | N-terminal truncation | 78 | (SEQ ID NO: 108) |
| W-E-Y-V-L-L-L-F-L-L | N-terminal truncation | 82 | (SEQ ID NO: 109) |
| V-S-F-A-I-K-W-E-Y-V-L-L-L-F-L-L | wild type | | (SEQ ID NO: 77) |
| V-S-F-A-I-K-W-E-Y-V-L-L-L-F-L | C-terminal truncation | 63 | (SEQ ID NO: 111) |
| V-S-F-A-I-K-W-E-Y-V-L-L-L-F | C-terminal truncation | 49 | (SEQ ID NO: 112) |
| V-S-F-A-I-K-W-E-Y-V-L-L-L | C-terminal truncation | 49 | (SEQ ID NO: 113) |
| V-S-F-A-I-K-W-E-Y-V-L-L | C-terminal truncation | 44 | (SEQ ID NO: 114) |
| V-S-F-A-I-K-W-E-Y-V-L | C-terminal truncation | 17 | (SEQ ID NO: 115) |
| V-S-F-A-I-K-W-E-Y-V | C-terminal truncation | 60 | (SEQ ID NO: 116) |

°Peptides were dissolved at 5 mM in 100% DMSO and tested at 50 uM in 1% DMSO.

Compared to the wild type 13-mer peptide (SEQ ID NO: 81), the retro peptide of SEQ ID NO: 81 (i.e., LLFLLLVYEWKIA (SEQ ID NO: 107)) and retro-inverso peptide of SEQ ID NO: 81 (i.e., LLFLLLVYEWKIA (SEQ ID NO: 107) with all D-amino acids) peptides completely lost activity, indicating that the overall hydrophobic nature of the retro and retro-inverso peptides is not enough for activity and the sequential order of certain key amino acids plays a leading role. The inverso peptides (SEQ ID NO: 81 with all D-amino acids), however, retained partial but weakened activity.

TABLE 10

Dose response curve for HCV entry at various concentrations of inverso, retro and retro-inverso peptides[¥]

| nM of peptide | inverso | | inverso | | inverso | | retro | | retro | | retro | |
|---|---|---|---|---|---|---|---|---|---|---|---|---|
| 30000 | 30 | 68 | 12 | 54 | 19 | 34 | 90 | 96 | 80 | 73 | 104 | 110 |
| 10000 | 40 | 44 | 41 | 46 | 27 | 52 | 54 | 99 | 55 | 79 | 34 | 63 |
| 300 | 78 | 62 | 70 | 77 | 46 | 41 | 66 | 79 | 119 | 69 | 54 | 62 |
| 100 | 67 | 74 | 106 | 84 | 60 | 82 | 101 | 79 | 99 | 72 | 65 | 62 |
| 30 | 120 | 94 | 91 | 86 | 72 | 45 | 58 | 93 | 92 | 94 | 45 | 64 |
| 10 | 115 | 97 | 99 | 74 | 86 | 89 | 95 | 93 | 81 | 52 | 68 | 77 |
| 3 | 109 | 86 | 108 | 74 | 80 | 90 | 99 | 121 | 76 | 62 | 77 | 66 |
| 1 | 98 | 87 | 73 | 123 | 99 | 88 | 86 | 97 | 81 | 94 | 51 | 88 |
| 0.3 | 118 | 102 | 110 | 112 | 73 | 69 | 98 | 86 | 95 | 88 | 88 | 91 |
| 0.1 | 139 | 111 | 90 | 93 | 117 | 94 | 87 | 114 | 83 | 82 | 72 | 67 |
| 0.1 | 116 | 69 | 91 | 88 | 68 | 101 | 93 | 109 | 96 | 90 | 90 | 102 |
| 0.1 | 122 | 92 | 109 | 112 | 124 | 108 | 98 | 100 | 107 | 107 | 92 | 116 |

TABLE 10-continued

Dose response curve for HCV entry at various concentrations of inverso, retro and retro-inverso peptides[¥]

| nM of peptide | retro-inverso | | retro-inverso | | retro-inverso | | SEQ ID NO: 81 | |
|---|---|---|---|---|---|---|---|---|
| 30000 | 107 | 87 | 103 | 125 | 107 | 95 | 30 | 26 |
| 10000 | 32 | 55 | 80 | 70 | 90 | 73 | 22 | 34 |
| 300 | 57 | 71 | 64 | 79 | 94 | 115 | 39 | 31 |
| 100 | 99 | 62 | 91 | 102 | 142 | 81 | 69 | 24 |
| 30 | 68 | 62 | 76 | 113 | 121 | 110 | 51 | 38 |
| 10 | 66 | 100 | 76 | 84 | 128 | 104 | 70 | 71 |
| 3 | 88 | 68 | 78 | 92 | 86 | 98 | 82 | 66 |
| 1 | 83 | 72 | 91 | 115 | 106 | 115 | 94 | 114 |
| 0.3 | 91 | 81 | 74 | 99 | 126 | 117 | 90 | 105 |
| 0.1 | 81 | 100 | 82 | 113 | 98 | 97 | 103 | 79 |
| 0.1 | 85 | 99 | 92 | 95 | 103 | 88 | 86 | 77 |
| 0.1 | 106 | 110 | 106 | 107 | 112 | 97 | 104 | 134 |

[¥]Numbers represent viral entry in the presence of the indicated peptide as a percentage of the uninhibited control.

TABLE 11

Dose response curve for HCV entry at various peptide concentrations.[£]

| uM of peptide | scrambled SEQ ID NO: 138 | | scrambled SEQ ID NO: 138 | | scrambled SEQ ID NO: 138 | | SEQ ID NO: 81 | | SEQ ID NO: 81 | |
|---|---|---|---|---|---|---|---|---|---|---|
| 30 | 7047 | 5340 | 7406 | 5158 | 5107 | 5826 | 990 | 667 | 907 | 406 |
| 10 | 9469 | 9957 | 12877 | 7340 | 8434 | 6401 | 2584 | 3853 | 2865 | 3393 |
| 3.333333 | 7729 | 11535 | 12632 | 8653 | 8028 | 10288 | 1152 | 2683 | 2490 | 2239 |
| 1.111111 | 6456 | 7681 | 9683 | 9482 | 9053 | 7359 | 2065 | 2449 | 2918 | 4380 |
| 0.3703704 | 7620 | 8597 | 9180 | 5716 | 8494 | 8291 | 2133 | 2617 | 3430 | 3658 |
| 0.1234568 | 9257 | 8961 | 11382 | 10746 | 7229 | 6598 | 1665 | 1759 | 2304 | 5077 |
| 0.04115226 | 12287 | 13159 | 13838 | 13589 | 10645 | 10230 | 3138 | 5487 | 6444 | 7203 |
| 0.01371742 | 13068 | 15343 | 14994 | 12097 | 11863 | 11748 | 4392 | 3561 | 7335 | 8987 |
| 0.01371742 | 15761 | 17272 | 24285 | 16582 | 13218 | 17842 | 13679 | 16041 | 14360 | 13526 |
| 0.01371742 | 20329 | 16998 | 20395 | 15327 | 17640 | 13895 | 12493 | 16554 | 13698 | 15168 |

| uM of peptide | SEQ ID NO: 81 | | SEQ ID NO: 81 | | SEQ ID NO: 81 | | SEQ ID NO: 103 | |
|---|---|---|---|---|---|---|---|---|
| 30 | 1899 | 1645 | 1938 | 2251 | 1262 | 1073 | 2946 | 4314 |
| 10 | 2867 | 1216 | 2186 | 2352 | 1538 | 1360 | 2732 | 4879 |
| 3.333333 | 2746 | 2356 | 2647 | 2056 | 4131 | 3158 | 3098 | 4136 |
| 1.111111 | 3652 | 3574 | 3285 | 2555 | 3041 | 2870 | 3136 | 4198 |
| 0.3703704 | 5748 | 3127 | 2830 | 5272 | 4161 | 2767 | 2800 | 5362 |
| 0.1234568 | 6445 | 3869 | 4583 | 6873 | 4241 | 3590 | 5848 | 7916 |
| 0.04115226 | 8349 | 8612 | 6486 | 6677 | 7066 | 7585 | 10722 | 14319 |
| 0.01371742 | 10981 | 12701 | 9747 | 12623 | 9526 | 11368 | 13380 | 14899 |
| 0.01371742 | 17159 | 18427 | 16027 | 17299 | 13637 | 13231 | 14290 | 13421 |
| 0.01371742 | 19121 | 16287 | 19079 | 17575 | 14358 | 15831 | 19490 | 13601 |

TABLE 12

Dose response curve for AMLV entry at various peptide concentrations.[£]

| uM of peptide | scrambled SEQ ID NO: 81 | | scrambled SEQ ID NO: 81 | | scrambled SEQ ID NO: 81 | | SEQ ID NO: 81 | | SEQ ID NO: 81 | |
|---|---|---|---|---|---|---|---|---|---|---|
| 30 | 87785 | 60410 | 83010 | 77083 | 85612 | 79287 | 86600 | 64937 | 83257 | 72040 |
| 10 | 70668 | 50409 | 97446 | 87834 | 101416 | 64206 | 153900 | 69448 | 172763 | 129890 |
| 3.333333 | 50674 | 41738 | 60859 | 50020 | 51236 | 49388 | 62658 | 51388 | 118949 | 92146 |
| 1.111111 | 49084 | 39443 | 53349 | 51341 | 46069 | 46019 | 54439 | 53032 | 48628 | 42996 |
| 0.3703704 | 48158 | 45212 | 49139 | 49219 | 51358 | 50551 | 48861 | 55221 | 43073 | 44659 |
| 0.1234568 | 39298 | 28711 | 46132 | 49974 | 42958 | 51726 | 51789 | 49401 | 44739 | 41483 |
| 0.04115226 | 43854 | 39721 | 46556 | 44480 | 40734 | 47413 | 40104 | 51496 | 42604 | 32390 |
| 0.01371742 | 49759 | 43879 | 46668 | 38054 | 46277 | 49423 | 46029 | 39655 | 43767 | 55532 |
| 0.01371742 | 37110 | 39504 | 40808 | 46160 | 44415 | 52102 | 41740 | 42548 | 44812 | 32138 |
| 0.01371742 | 37232 | 42195 | 45601 | 44163 | 52921 | 49326 | 45150 | 45203 | 40068 | 41172 |

TABLE 12-continued

Dose response curve for AMLV entry at various peptide concentrations.[£]

| uM of peptide | SEQ ID NO: 81 | | SEQ ID NO: 81 | | SEQ ID NO: 81 | | SEQ ID NO: 103 | |
|---|---|---|---|---|---|---|---|---|
| 30 | 76174 | 71333 | 81103 | 70832 | 76883 | 56072 | 116018 | 90397 |
| 10 | 70573 | 72462 | 111324 | 59835 | 135633 | 74847 | 182409 | 156275 |
| 3.3333 | 53350 | 39047 | 59984 | 48300 | 70934 | 59407 | 60851 | 69213 |
| 1.1111 | 40296 | 43593 | 45508 | 44147 | 45723 | 43633 | 49626 | 41878 |
| 0.3704 | 43543 | 47987 | 42748 | 48710 | 42008 | 39907 | 49219 | 41944 |
| 0.1235 | 37163 | 47412 | 45455 | 45030 | 46954 | 44234 | 53044 | 67129 |
| 0.0412 | 42084 | 47952 | 41463 | 41610 | 39784 | 45324 | 45898 | 42568 |
| 0.0137 | 42295 | 44556 | 44492 | 44531 | 45888 | 43209 | 44656 | 41299 |
| 0.0137 | 43059 | 48854 | 47406 | 49869 | 52210 | 102903 | 45140 | 43684 |
| 0.0137 | 37783 | 49462 | 51067 | 61382 | 41952 | 46766 | 39179 | 81198 |

[£]Numbers represent luciferase units observed in the viral entry assays conducted. SEQ ID Nos: 81, 85, 86, 98 and 100 represent the identical wild type 13-mer sequence from independent synthesis.

Scrambled 13-mer peptides were clearly different from the wild type 13-mer but yet retained some HCVpp-specific inhibition. The fact that the scrambled 13-mer LKLFEVYLIL-WLA (SEQ ID NO: 138) still showed some activity, though weakened, implies that what matters for the activity is either the overall hydrophobicity of the peptide and/or the preeminent importance of perhaps as few as two or three of the residues, or the accumulative small contributions from residues in the right places. However, as noted above, since the equally hydrophobic retro and retro-inverso peptides were inactive, and as we shall see below, the contributions to activity are most likely from many residues, thus it is more likely that a significant portion of anti-viral activity comes from residues that happen to be at the approximate right places in the overall scrambled context. The amino acid scanning experiments, below, reaffirmed the notion of collective contributions by many residues.

Gly scanning: Glycine substitutions not only eliminated the side chains, but they were expected to introduce much greater local backbone conformational flexibilities. This enhanced conformational freedom can effectively dilute the presence of bioactive conformations, leading to weaker activities. Peptides of SEQ ID NOs: 82-84 and 111 are similarly active or slightly better than wild-type, others were less active. It appears that the N-terminal A/I/E/Y (SEQ ID NO: 139) sequence can tolerate four (A/I/E/Y) of six substitutions, whereas the Leu-rich carboxy terminal segment is less forgiving to glycine replacement.

The data generated in the glycine scanning experiments is set forth below in Table 13.

TABLE 13

Glycine scanning experiments

| uM of peptide | SEQ ID NO: 81 (% control) | | SEQ ID NO: 82 (% control) | | SEQ ID NO: 83 (% control) | | SEQ ID NO: 109 (% control) | | SEQ ID NO: 77 (% control) | | SEQ ID NO: 84 (% control) | | SEQ ID NO: 111 (% control) | | SEQ ID NO: 112 (% control) | | SEQ ID NO: 113 (% control) | | SEQ ID NO: 114 (% control) | |
|---|---|---|---|---|---|---|---|---|---|---|---|---|---|---|---|---|---|---|---|---|
| 30 | 30 | 26 | 18 | 29 | 18 | 15 | 50 | 28 | 3 | 23 | 22 | 38 | 10 | 22 | 24 | 37 | 41 | 147 | 118 | 19 |
| 10 | 22 | 34 | 33 | 29 | 27 | 89 | 66 | 80 | 24 | 18 | 10 | 40 | 22 | 21 | 34 | 51 | 38 | 36 | 30 | 28 |
| 0.3 | 39 | 31 | 33 | 25 | 17 | 56 | 40 | 69 | 51 | 54 | 37 | 57 | 36 | 42 | 51 | 61 | 46 | 56 | 51 | 34 |
| 0.1 | 69 | 24 | 33 | 27 | 19 | 47 | 60 | 77 | 61 | 82 | 41 | 39 | 50 | 46 | 67 | 62 | 78 | 72 | 46 | 64 |
| 0.03 | 51 | 38 | 46 | 41 | 43 | 62 | 61 | 72 | 87 | 71 | 62 | 52 | 42 | 52 | 64 | 79 | 76 | 78 | 93 | 101 |
| 0.01 | 70 | 71 | 53 | 43 | 76 | 56 | 84 | 111 | 77 | 81 | 72 | 53 | 49 | 81 | 71 | 69 | 101 | 95 | 82 | 113 |
| 0.003 | 82 | 66 | 71 | 80 | 51 | 66 | 99 | 139 | 102 | 65 | 70 | 70 | 56 | 79 | 83 | 121 | 94 | 116 | 92 | 102 |
| 0.001 | 94 | 114 | 90 | 66 | 70 | 67 | 93 | 96 | 109 | 91 | 74 | 73 | 65 | 92 | 100 | 88 | 101 | 94 | 101 | 84 |
| 0.0003 | 90 | 105 | 68 | 71 | 94 | 83 | 94 | 100 | 107 | 97 | 91 | 81 | 111 | 59 | 71 | 88 | 87 | 121 | 84 | 92 |
| 0.0001 | 103 | 79 | 62 | 61 | 75 | 94 | 86 | 103 | 84 | 100 | 62 | 75 | 81 | 86 | 103 | 112 | 89 | 92 | 93 | 85 |
| 0.00003 | 86 | 77 | 74 | 88 | 98 | 80 | 88 | 110 | 119 | 104 | 118 | 84 | 82 | 99 | 112 | 74 | 103 | 115 | 85 | 89 |
| 0.00003 | 104 | 134 | 118 | 120 | 128 | 94 | 93 | 109 | 87 | 90 | 87 | 110 | 114 | 106 | 111 | 103 | 80 | 101 | 111 | 115 |

Ala scanning: Contrary to glycine, devoid of any side chain, alanine still maintains similar backbone conformational rigidity as other L-amino acids. Most alanine mutants are similar to the wild-type, except for the peptide of SEQ ID NO: 115. These data suggested that the expression of viral entry blocking activity is contributed largely collectively by many constituent residues, except somewhat more significantly by the leucine amino terminal to phenylalanine.

The data generated in the alanine scanning experiments is set forth below in Table 14.

TABLE 14

Alanine scanning experiments

| nM of peptide | SEQ ID NO: 81 (% control) | | SEQ ID NO: 81 (% control) | | SEQ ID NO: 87 (% control) | | SEQ ID NO: 88 (% control) | | SEQ ID NO: 89 (% control) | | SEQ ID NO: 90 (% control) | | SEQ ID NO: 91 (% control) | |
|---|---|---|---|---|---|---|---|---|---|---|---|---|---|---|
| 30000 | 70 | 103 | 15 | 27 | 11 | 6 | 8 | 45 | 4 | 12 | 29 | 4 | 12 | 18 |
| 10000 | 13 | 18 | 27 | 25 | 15 | 23 | 27 | 32 | 24 | 17 | 40 | 14 | 30 | 15 |
| 300 | 18 | 22 | 25 | 30 | 16 | 13 | 42 | 45 | 24 | 27 | 55 | 55 | 17 | 27 |
| 100 | 45 | 50 | 48 | 33 | 19 | 15 | 37 | 57 | 41 | 38 | 51 | 43 | 35 | 32 |
| 30 | 62 | 57 | 59 | 60 | 42 | 51 | 53 | 66 | 66 | 71 | 69 | 63 | 49 | 48 |
| 10 | 90 | 107 | 69 | 67 | 45 | 57 | 56 | 60 | 63 | 57 | 66 | 46 | 59 | 66 |
| 3 | 71 | 88 | 90 | 118 | 92 | 68 | 81 | 93 | 63 | 76 | 106 | 81 | 86 | 110 |
| 1 | 95 | 83 | 80 | 102 | 110 | 93 | 100 | 69 | 85 | 96 | 66 | 98 | 120 | 102 |
| 0.3 | 79 | 96 | 96 | 133 | 84 | 75 | 91 | 101 | 71 | 64 | 73 | 94 | 81 | 84 |
| 0.1 | 79 | 81 | 86 | 90 | 90 | 108 | 96 | 85 | 84 | 76 | 105 | 98 | 101 | 73 |
| 0.1 | 101 | 74 | 87 | 103 | 113 | 90 | 87 | 108 | 104 | 95 | 82 | 106 | 107 | 89 |
| 0.1 | 113 | 112 | 103 | 108 | 93 | 104 | 96 | 109 | 96 | 105 | 116 | 96 | 93 | 111 |

| nM of peptide | SEQ ID NO: 92 (% control) | | SEQ ID NO: 93 (% control) | | SEQ ID NO: 94 (% control) | | SEQ ID NO: 115 (% control) | | SEQ ID NO: 95 (% control) | | SEQ ID NO: 96 (% control) | | SEQ ID NO: 97 (% control) | |
|---|---|---|---|---|---|---|---|---|---|---|---|---|---|---|
| 30000 | 5 | 15 | 32 | 32 | 14 | 28 | 36 | 0 | 7 | 23 | 31 | 31 | 53 | 50 |
| 10000 | 12 | 27 | 41 | 32 | 36 | 34 | 11 | 38 | 25 | 15 | 33 | 20 | 19 | 37 |
| 300 | 21 | 30 | 32 | 27 | 42 | 33 | 64 | 40 | 18 | 13 | 36 | 26 | 30 | 47 |
| 100 | 32 | 25 | 47 | 42 | 45 | 41 | 54 | 53 | 35 | 53 | 24 | 41 | 46 | 51 |
| 30 | 42 | 64 | 58 | 51 | 58 | 48 | 88 | 72 | 75 | 35 | 63 | 67 | 55 | 80 |
| 10 | 82 | 59 | 71 | 67 | 79 | 86 | 105 | 78 | 64 | 47 | 58 | 73 | 79 | 69 |
| 3 | 68 | 99 | 78 | 87 | 58 | 89 | 102 | 86 | 85 | 52 | 76 | 85 | 72 | 92 |
| 1 | 90 | 80 | 85 | 87 | 81 | 82 | 66 | 93 | 91 | 72 | 124 | 78 | 76 | 92 |
| 0.3 | 85 | 61 | 86 | 105 | 104 | 92 | 82 | 91 | 62 | 70 | 91 | 98 | 72 | 102 |
| 0.1 | 73 | 115 | 91 | 83 | 99 | 96 | 83 | 118 | 89 | 82 | 95 | 86 | 80 | 101 |
| 0.1 | 82 | 89 | 80 | 104 | 79 | 101 | 108 | 124 | 114 | 76 | 100 | 96 | 105 | 102 |
| 0.1 | 99 | 130 | 134 | 81 | 115 | 105 | 81 | 86 | 113 | 97 | 72 | 132 | 95 | 97 |

Pro scanning: Unlike the conformationally permissive glycine, proline is far more restrictive due to the side chain to backbone nitrogen ring closure. Introducing proline into the peptide was aimed at creating local contortion of the peptide backbone and probing if a less aggregating and more water soluble but active mutant peptide can emerge. Only the very amino terminal alanine to proline mutant (SEQ ID NO: 99) was similar to the wild-type peptide, others are less active. This suggested that local backbone contortion would ablate activity.

The data generated in the proline scanning experiments is set forth below in Table 15.

TABLE 15

Proline scanning experiments.

| nM of peptide | SEQ ID NO: 81 (% control) | | SEQ ID NO: 99 (% control) | | SEQ ID NO: 116 (% control) | | SEQ ID NO: 117 (% control) | | SEQ ID NO: 118 (% control) | | SEQ ID NO: 119 (% control) | | SEQ ID NO: 120 (% control) | |
|---|---|---|---|---|---|---|---|---|---|---|---|---|---|---|
| 30000 | 19 | 6 | 2 | 9 | 2 | 5 | 49 | 4 | 24 | 33 | 28 | 17 | 38 | 42 |
| 10000 | 27 | 24 | 24 | 16 | 15 | 19 | 54 | 31 | 16 | 41 | 21 | 7 | 24 | 24 |
| 300 | 21 | 29 | 21 | 29 | 18 | 34 | 48 | 41 | 38 | 29 | 40 | 47 | 33 | 39 |
| 100 | 31 | 41 | 21 | 34 | 49 | 28 | 38 | 54 | 47 | 53 | 40 | 46 | 39 | 39 |
| 30 | 41 | 35 | 28 | 36 | 29 | 46 | 58 | 71 | 63 | 93 | 39 | 79 | 72 | 40 |
| 10 | 47 | 50 | 45 | 53 | 61 | 58 | 75 | 75 | 116 | 83 | 54 | 48 | 73 | 76 |
| 3 | 86 | 52 | 68 | 56 | 68 | 86 | 89 | 66 | 108 | 84 | 94 | 62 | 66 | 76 |
| 1 | 93 | 94 | 75 | 89 | 81 | 93 | 68 | 87 | 74 | 99 | 72 | 68 | 91 | 75 |
| 0.3 | 90 | 68 | 84 | 80 | 86 | 76 | 66 | 117 | 101 | 92 | 78 | 77 | 90 | 75 |
| 0.1 | 85 | 77 | 64 | 84 | 89 | 74 | 128 | 93 | 80 | 87 | 93 | 76 | 82 | 78 |
| 0.1 | 86 | 109 | 108 | 70 | 98 | 105 | 91 | 97 | 103 | 108 | 87 | 85 | 102 | 80 |
| 0.1 | 109 | 95 | 101 | 121 | 120 | 77 | 144 | 68 | 110 | 79 | 102 | 126 | 101 | 117 |

TABLE 15-continued

Proline scanning experiments.

| nM of peptide | SEQ ID NO: 121 (% control) | | SEQ ID NO: 122 (% control) | | SEQ ID NO: 123 (% control) | | SEQ ID NO: 124 (% control) | | SEQ ID NO: 125 (% control) | | SEQ ID NO: 126 (% control) | | SEQ ID NO: 127 (% control) | |
|---|---|---|---|---|---|---|---|---|---|---|---|---|---|---|
| 30000 | 32 | 41 | 51 | 23 | 31 | 49 | 98 | 67 | 68 | 59 | 55 | 80 | 57 | 29 |
| 10000 | 50 | 23 | 54 | 43 | 61 | 51 | 85 | 60 | 73 | 54 | 43 | 44 | 29 | 27 |
| 300 | 42 | 30 | 76 | 53 | 41 | 44 | 85 | 68 | 63 | 76 | 72 | 85 | 63 | 72 |
| 100 | 44 | 63 | 75 | 59 | 72 | 61 | 66 | 83 | 60 | 58 | 68 | 81 | 77 | 74 |
| 30 | 70 | 82 | 70 | 113 | 74 | 75 | 48 | 71 | 80 | 102 | 83 | 82 | 78 | 83 |
| 10 | 75 | 66 | 85 | 67 | 78 | 76 | 67 | 102 | 97 | 109 | 86 | 76 | 102 | 74 |
| 3 | 85 | 87 | 106 | 80 | 92 | 78 | 80 | 86 | 85 | 82 | 98 | 89 | 66 | 53 |
| 1 | 76 | 110 | 73 | 100 | 108 | 77 | 89 | 102 | 75 | 99 | 88 | 93 | 71 | 85 |
| 0.3 | 68 | 84 | 105 | 83 | 80 | 91 | 74 | 88 | 104 | 104 | 88 | 91 | 84 | 81 |
| 0.1 | 77 | 95 | 81 | 70 | 78 | 81 | 87 | 98 | 91 | 99 | 83 | 66 | 90 | 86 |
| 0.1 | 91 | 115 | 89 | 86 | 104 | 86 | 89 | 104 | 111 | 92 | 89 | 87 | 90 | 75 |
| 0.1 | 104 | 90 | 115 | 111 | 117 | 94 | 109 | 97 | 95 | 101 | 104 | 119 | 122 | 113 |

Lys scanning: Lysine was positively charged under the assay condition. Lysine scanning was aimed at reversing the local hydrophobic character and assessing the consequence to potency. Similar to glycine scanning, the amino terminal substitutions were more tolerant; thus peptides of SEQ ID NOs: 101, 102 and 129 were similar or slightly more potent than the wild-type peptide, while others were less potent than the wild-type peptide.

The data generated in the lysine scanning experiments is set forth below in Table 16.

TABLE 16

Lysine scanning experiments

| nM of peptide | SEQ ID NO: 81 (% control) | | SEQ ID NO: 101 (% control) | | SEQ ID NO: 102 (% control) | | SEQ ID NO: 103 (% control) | | SEQ ID NO: 128 (% control) | | SEQ ID NO: 103 (% control) | | SEQ ID NO: 130 (% control) | |
|---|---|---|---|---|---|---|---|---|---|---|---|---|---|---|
| 30000 | 6 | 22 | 7 | 1 | 7 | 2 | 2 | 18 | 1 | 9 | 9 | 2 | 26 | 4 |
| 10000 | 5 | 20 | 2 | 18 | 17 | 7 | 9 | 23 | 4 | 7 | 6 | 17 | 38 | 3 |
| 300 | 32 | 29 | 26 | 29 | 29 | 23 | 30 | 29 | 28 | 22 | 15 | 19 | 33 | 19 |
| 100 | 31 | 19 | 26 | 25 | 16 | 25 | 28 | 27 | 46 | 52 | 15 | 27 | 58 | 24 |
| 30 | 53 | 44 | 37 | 28 | 33 | 41 | 29 | 29 | 55 | 59 | 27 | 35 | 74 | 75 |
| 10 | 62 | 58 | 54 | 57 | 67 | 62 | 84 | 67 | 92 | 63 | 43 | 50 | 90 | 102 |
| 3 | 61 | 83 | 52 | 77 | 70 | 66 | 80 | 81 | 81 | 84 | 91 | 81 | 95 | 81 |
| 1 | 76 | 68 | 65 | 90 | 96 | 83 | 104 | 61 | 72 | 99 | 97 | 85 | 114 | 89 |
| 0.3 | 88 | 75 | 96 | 103 | 141 | 107 | 93 | 79 | 88 | 64 | 104 | 83 | 103 | 100 |
| 0.1 | 110 | 85 | 83 | 107 | 104 | 102 | 117 | 92 | 86 | 80 | 80 | 93 | 122 | 84 |
| 0.1 | 115 | 83 | 77 | 104 | 89 | 108 | 104 | 77 | 102 | 107 | 92 | 87 | 106 | 96 |
| 0.1 | 92 | 111 | 119 | 101 | 98 | 106 | 131 | 88 | 103 | 87 | 101 | 120 | 105 | 93 |

| nM of peptide | SEQ ID NO: 131 (% control) | | SEQ ID NO: 132 (% control) | | SEQ ID NO: 133 (% control) | | SEQ ID NO: 134 (% control) | | SEQ ID NO: 135 (% control) | | SEQ ID NO: 136 (% control) | | SEQ ID NO: 137 (% control) | |
|---|---|---|---|---|---|---|---|---|---|---|---|---|---|---|
| 30000 | 30 | 44 | 42 | 41 | 16 | 42 | 56 | 45 | 29 | 37 | 26 | 62 | 27 | 9 |
| 10000 | 16 | 14 | 49 | 50 | 24 | 39 | 60 | 47 | 43 | 57 | 34 | 68 | 23 | 28 |
| 300 | 29 | 42 | 46 | 44 | 41 | 56 | 75 | 68 | 70 | 87 | 81 | 84 | 54 | 77 |
| 100 | 49 | 62 | 59 | 62 | 75 | 60 | 89 | 87 | 107 | 75 | 98 | 84 | 68 | 74 |
| 30 | 71 | 68 | 71 | 89 | 80 | 68 | 101 | 76 | 89 | 90 | 65 | 84 | 78 | 94 |
| 10 | 74 | 66 | 54 | 56 | 77 | 113 | 105 | 77 | 104 | 79 | 80 | 71 | 100 | 89 |
| 3 | 71 | 85 | 78 | 75 | 95 | 79 | 94 | 92 | 74 | 67 | 76 | 98 | 82 | 97 |
| 1 | 85 | 68 | 67 | 79 | 96 | 82 | 128 | 81 | 84 | 76 | 71 | 90 | 80 | 106 |
| 0.3 | 105 | 81 | 100 | 71 | 108 | 78 | 104 | 85 | 99 | 72 | 103 | 70 | 58 | 92 |
| 0.1 | 97 | 80 | 73 | 89 | 78 | 85 | 80 | 96 | 63 | 96 | 67 | 81 | 72 | 123 |
| 0.1 | 97 | 94 | 95 | 92 | 96 | 101 | 108 | 75 | 74 | 85 | 82 | 94 | 80 | 82 |
| 0.1 | 96 | 113 | 117 | 96 | 87 | 116 | 138 | 79 | 129 | 112 | 116 | 108 | 103 | 135 |

The peptides generated in the Ala-, Lys- and Pro-scanning experiments are set forth below in table 17.

TABLE 17

Peptides generated in Ala-, Lys- and Pro- scanning experiments

| Amino acid sequence | Sequence identifier |
|---|---|
| A-I-K-W-E-Y-V-L-L-F-L-L | SEQ ID NO: 81 |
| G-I-K-W-E-Y-V-L-L-F-L-L | SEQ ID NO: 82 |
| A-G-K-W-E-Y-V-L-L-F-L-L | SEQ ID NO: 83 |
| A-I-G-W-E-Y-V-L-L-F-L-L | SEQ ID NO: 109 |
| A-I-K-G-E-Y-V-L-L-F-L-L | SEQ ID NO: 77 |
| A-I-K-W-G-Y-V-L-L-F-L-L | SEQ ID NO: 84 |
| A-I-K-W-E-G-V-L-L-F-L-L | SEQ ID NO: 111 |
| A-I-K-W-E-Y-G-L-L-F-L-L | SEQ ID NO: 112 |
| A-I-K-W-E-Y-V-L-L-F-G-L | SEQ ID NO: 113 |
| A-I-K-W-E-Y-V-L-L-F-L-G | SEQ ID NO: 114 |
| A-I-K-W-E-Y-V-L-L-F-L-L | SEQ ID NO: 81 |
| A-I-K-W-E-Y-V-L-L-F-L-L | SEQ ID NO: 86 |
| A-A-K-W-E-Y-V-L-L-F-L-L | SEQ ID NO: 87 |
| A-I-A-W-E-Y-V-L-L-F-L-L | SEQ ID NO: 88 |
| A-I-K-A-E-Y-V-L-L-F-L-L | SEQ ID NO: 89 |
| A-I-K-W-A-Y-V-L-L-F-L-L | SEQ ID NO: 90 |
| A-I-K-W-E-A-V-L-L-F-L-L | SEQ ID NO: 91 |
| A-I-K-W-E-Y-A-L-L-F-L-L | SEQ ID NO: 92 |
| A-I-K-W-E-Y-V-A-L-F-L-L | SEQ ID NO: 93 |
| A-I-K-W-E-Y-V-L-A-F-L-L | SEQ ID NO: 94 |
| A-I-K-W-E-Y-V-L-L-A-L-L | SEQ ID NO: 115 |
| A-I-K-W-E-Y-V-L-L-F-A-L | SEQ ID NO: 95 |
| A-I-K-W-E-Y-V-L-L-F-A-L | SEQ ID NO: 96 |
| A-I-K-W-E-Y-V-L-L-F-L-A | SEQ ID NO: 97 |
| A-I-K-W-E-Y-V-L-L-F-L-L | SEQ ID NO: 81 |
| P-I-K-W-E-Y-V-L-L-F-L-L | SEQ ID NO: 99 |
| A-P-K-W-E-Y-V-L-L-F-L-L | SEQ ID NO: 116 |
| A-I-P-W-E-Y-V-L-L-F-L-L | SEQ ID NO: 117 |
| A-I-K-P-E-Y-V-L-L-F-L-L | SEQ ID NO: 118 |
| A-I-K-W-P-Y-V-L-L-F-L-L | SEQ ID NO: 119 |
| A-I-K-W-E-P-V-L-L-F-L-L | SEQ ID NO: 120 |
| A-I-K-W-E-Y-P-L-L-F-L-L | SEQ ID NO: 121 |
| A-I-K-W-E-Y-V-P-L-F-L-L | SEQ ID NO: 122 |
| A-I-K-W-E-Y-V-L-P-F-L-L | SEQ ID NO: 123 |
| A-I-K-W-E-Y-V-L-L-P-F-L-L | SEQ ID NO: 124 |
| A-I-K-W-E-Y-V-L-L-P-L-L | SEQ ID NO: 125 |
| A-I-K-W-E-Y-V-L-L-F-P-L | SEQ ID NO: 126 |
| A-I-K-W-E-Y-V-L-L-F-L-P | SEQ ID NO: 127 |
| A-I-K-W-E-Y-V-L-L-F-L-L | SEQ ID NO: 81 |
| K-I-K-W-E-Y-V-L-L-F-L-L | SEQ ID NO: 101 |
| A-K-K-W-E-Y-V-L-L-F-L-L | SEQ ID NO: 102 |
| A-I-K-W-E-Y-V-L-L-F-L-L | SEQ ID NO: 103 |
| A-I-K-K-E-Y-V-L-L-F-L-L | SEQ ID NO: 128 |
| A-I-K-W-K-Y-V-L-L-F-L-L | SEQ ID NO: 129 |
| A-I-K-W-E-K-V-L-L-F-L-L | SEQ ID NO: 130 |
| A-I-K-W-E-Y-K-L-L-F-L-L | SEQ ID NO: 131 |
| A-I-K-W-E-Y-V-K-L-F-L-L | SEQ ID NO: 132 |
| A-I-K-W-E-Y-V-L-K-F-L-L | SEQ ID NO: 133 |
| A-I-K-W-E-Y-V-L-L-K-F-L-L | SEQ ID NO: 134 |
| A-I-K-W-E-Y-V-L-L-K-L-L | SEQ ID NO: 135 |
| A-I-K-W-E-Y-V-L-L-F-K-L | SEQ ID NO: 136 |
| A-I-K-W-E-Y-V-L-L-F-L-K | SEQ ID NO: 137 |

Taken together, the scanning data, establish that the amino terminal segment (AIKWE) (SEQ ID NO: 139) was more tolerant to substitutions whereas the carboxy terminal hydrophobic segment was less so. The potency was contributed collectively by many residues (as seen in alanine scanning). Peptide backbone contortion (as in proline scanning) or conformational de-constraining (as in glycine scanning) was not well tolerated. Perturbing the hydrophobic character in the carboxy terminal segment is also detrimental to activity (as seen with lysine scanning).

Example 3

Steps of HCVpp Entry Affected by the Peptide

To identify if the peptides of the invention bind to the cells and therefore inhibit entry, anti-CD81 antibody or peptide (SEQ ID NO: 77) was tested at four conditions:
 (A) peptide or anti-CD81 antibody was pre-incubated with cells and virus separately, cells were washed and virus together with peptide was added;
 (B) peptide or anti-CD81 antibody was pre-incubated with virus only first and then virus together with peptide was added to the cells;
 (C) peptide or anti-CD81 antibody was preincubated with cells only and washed off, and then virus was added; and
 (D) same as C except that virus was washed off after 1 hour of incubation.

Realizing that during virus incubation, the pre-bond peptide or antibody could dissociate from the cells and therefore lose the effects on HCVpp entry, virus was removed at time points from 15 minutes to 4 hours and we compared the inhibition effects to that from leaving viruses on until harvest for luciferase. As shown in the data of table 18, when virus was removed at earlier time points, stronger inhibition was observed compared to leaving virus on until harvest.

TABLE 18

Results of time course wherein virus was removed at various points.*

| anti-CD81 ug/ml | 5 min | | 15 min | | 30 min | | 1 hr | | 2 hr | | 3 hr | | 4 hr | | leaving on | | no wash off | |
|---|---|---|---|---|---|---|---|---|---|---|---|---|---|---|---|---|---|---|
| 10 | 63 | 60 | 19 | 29 | 21 | 25 | 25 | 35 | 31 | 67 | 45 | 48 | 61 | 88 | 29 | 73 | 0 | 1 |
| 3.3333 | 54 | 27 | 34 | 41 | 36 | 33 | 27 | 34 | 32 | 59 | 54 | 45 | 58 | 65 | 61 | 73 | 4 | 3 |
| 1.1111 | 36 | 56 | 87 | 57 | 25 | 46 | 11 | 61 | 51 | 56 | 63 | 63 | 72 | 90 | 54 | 83 | 6 | 2 |
| 0.3704 | 68 | 98 | 55 | 59 | 75 | 71 | 27 | 43 | 61 | 86 | 89 | 71 | 76 | 112 | 67 | 95 | 22 | 22 |
| 0.1235 | 25 | 59 | 39 | 33 | 50 | 32 | 39 | 21 | 45 | 42 | 66 | 52 | 50 | 41 | 74 | 98 | 99 | 122 |
| 0.0412 | 22 | 27 | 69 | 37 | 89 | 86 | 52 | 49 | 53 | 78 | 58 | 69 | 62 | 51 | 72 | 111 | 88 | 101 |
| 0.0137 | 36 | 56 | 79 | 64 | 71 | 93 | 33 | 49 | 60 | 64 | 62 | 87 | 65 | 74 | 69 | 110 | 106 | 124 |
| 0.0046 | 85 | 27 | 55 | 66 | 61 | 72 | 65 | 66 | 57 | 73 | 71 | 87 | 65 | 53 | 71 | 112 | 84 | 97 |
| 0.0015 | 83 | 67 | 142 | 104 | 109 | 122 | 72 | 71 | 87 | 79 | 103 | 91 | 99 | 104 | 80 | 118 | 117 | 97 |
| 0.0005 | 127 | 117 | 68 | 74 | 75 | 92 | 88 | 74 | 63 | 91 | 87 | 91 | 92 | 79 | 77 | 114 | 94 | 92 |
| 0.0002 | 80 | 79 | 89 | 75 | 90 | 120 | 145 | 78 | 119 | 119 | 82 | 108 | 126 | 97 | 74 | 108 | | |
| 0.0002 | 95 | 145 | 138 | 98 | 89 | 101 | 94 | 83 | 70 | 92 | 100 | 110 | 94 | 83 | 93 | 124 | | |

*Numbers represent the viral entry observed at each time point and antibody concentration tested as a percentage of the uninhibited control The majority of difference seen before the 4-hour timepoint is in line with the model wherein most of the entry events occur during the first four hours (data not shown). As expected, the RLU signal was reduced at earlier time points and lead to higher variation of the assay. In general, when anti-CD81 antibody was removed, the earlier removal of virus seemed to correlate with a greater inhibition, indicating dissociation of anti-CD81 antibody from cells. In anticipating similar phenomena might exist with the peptide, we applied the one hour virus incubation in the following studies. In tables 19-22, condition D was identical to condition C except that virus was removed after 1 hour of incubation. The dose-response curves from condition A superimposed that from condition B, and little inhibition was observed at condition C, indicating the pre-bond antibody or peptide on cell offered no advantages in blocking HCVpp entry, or alternatively, the affinity of peptide and antibody to cells is low and can dissociate from cells rather quickly. The experiments performed under condition D suggested that the latter might be the case, in that the earlier the infection was terminated, there seemed to be a greater inhibition effect from the prebond peptide and antibody. Anti-CD81 antibody binds to CD81 expressed on the cells and therefore blocks HCVpp entry. Comparing to anti-CD81 antibody, the peptide exhibited more inhibition when pre-incubated with cells at 37° C. and 4° C. in the wash-off experiment, indicating that it most likely interacted with the cells and inhibited HCVpp entry.

The data in tables 19 and 20 were generated in assays conducted at 37° C. The date generated in tables 21 and 22 were generated in assays conducted at 4° C. The numbers in each table (19-22) represent the luciferase units observed in the entry assay under each indicated condition.

TABLE 19

Wash off study of anti-CD-81 antibody at 37° C.

| anti-CD81 antibody (ug/ml) | condition A | | condition B | | condition C | | condition D | |
|---|---|---|---|---|---|---|---|---|
| 10 | 179 | 609 | 885 | 1378 | 35920 | 35648 | 5002 | 1964 |
| 3.333333 | 1923 | 1259 | 1481 | 1643 | 39146 | 32572 | 2063 | 3976 |
| 1.111111 | 2437 | 719 | 3672 | 1402 | 35842 | 33312 | 3158 | 2386 |
| 0.3703704 | 9829 | 9696 | 9224 | 11247 | 39546 | 36517 | 1192 | 3805 |
| 0.1234568 | 43590 | 53450 | 53230 | 41923 | 41983 | 46677 | 3801 | 8524 |
| 0.04115226 | 38615 | 44249 | 45687 | 40315 | 51423 | 45565 | 2736 | 4057 |
| 0.01371742 | 46405 | 54468 | 38470 | 48976 | 38356 | 42778 | 2755 | 5184 |
| 0.004572474 | 36968 | 42764 | 46670 | 44647 | 38239 | 42076 | 3899 | 4580 |
| 0.004572474 | 51599 | 42409 | 56802 | 46508 | 41564 | 49023 | 3482 | 7151 |
| 0.004572474 | 41187 | 40579 | 34004 | 46112 | 38135 | 44170 | 5511 | 6649 |

TABLE 20

Wash off study of peptide (SEQ ID NO: 77) at 37° C.

| peptide V-2b (SEQ ID NO: 77) (ug/ml) | condition A | | condition B | | condition C | | condition D | |
|---|---|---|---|---|---|---|---|---|
| 100.0000 | 9216 | 7419 | 8074 | 4093 | 19088 | 14073 | 780 | 1531 |
| 33.3333 | 6467 | 6356 | 7146 | 4501 | 23383 | 19309 | 2351 | 2058 |
| 11.1111 | 12402 | 6768 | 10212 | 6902 | 28818 | 33022 | 3302 | 3259 |
| 3.7037 | 15025 | 10613 | 15213 | 12233 | 31857 | 32265 | 2974 | 3707 |
| 1.2346 | 21301 | 21733 | 25204 | 14452 | 36450 | 40467 | 2078 | 4828 |
| 0.4115 | 28106 | 25559 | 26979 | 31819 | 40225 | 43467 | 3257 | 2555 |
| 0.1372 | 44159 | 41959 | 43468 | 36136 | 34241 | 44163 | 2443 | 4834 |
| 0.0457 | 50460 | 53231 | 47929 | 53377 | 36956 | 46680 | 3531 | 2785 |
| 0.0046 | 74772 | 76125 | 65028 | 60343 | 40529 | 45271 | 4566 | 6407 |
| 0.0046 | 57485 | 58523 | 57349 | 51858 | 37116 | 32831 | 3984 | 2714 |

TABLE 21

Wash off study of anti-CD-81 antibody at 4° C.

| anti-CD81 antibody (ug/ml) | condition A | | condition B | | condition C | |
|---|---|---|---|---|---|---|
| 10 | 42 | 242 | 78 | 37 | 6720 | 8027 |
| 3.3333 | 14 | 135 | 382 | 470 | 11036 | 10783 |
| 1.1111 | 1733 | 253 | 1815 | 706 | 10112 | 11783 |
| 0.3704 | 1885 | 1046 | 2988 | 1939 | 9220 | 18281 |
| 0.1235 | 6160 | 5063 | 7111 | 5662 | 11651 | 11051 |
| 0.0412 | 11764 | 8052 | 16527 | 11566 | 10723 | 11422 |
| 0.0137 | 12944 | 10622 | 13979 | 15817 | 7207 | 12271 |
| 0.0046 | 10693 | 11365 | 12812 | 11119 | 11552 | 15524 |
| 0.0046 | 9969 | 11238 | 15082 | 15072 | 12008 | 9342 |
| 0.0046 | 15243 | 12178 | 10078 | 12548 | 8921 | 9666 |

TABLE 22

Wash off study of peptide (SEQ ID NO: 77) at 4° C.

| peptide V-2b (SEQ ID No: 77) (ug/ml) | condition A | | condition B | | condition C | |
|---|---|---|---|---|---|---|
| 100 | 1924 | 1845 | 1233 | 2486 | 5118 | 8821 |
| 33.3333 | 1677 | 2383 | 2900 | 1914 | 8294 | 8104 |
| 11.1111 | 2833 | 2954 | 996 | 2597 | 7352 | 4725 |
| 3.7037 | 2824 | 3255 | 3059 | 3424 | 9414 | 8570 |
| 1.2346 | 3584 | 5974 | 5542 | 4382 | 6131 | 6853 |
| 0.4115 | 5517 | 5574 | 4724 | 3648 | 9027 | 11381 |
| 0.1372 | 5745 | 7826 | 7670 | 6880 | 9444 | 10124 |
| 0.0457 | 7498 | 7299 | 6703 | 9954 | 16101 | 13757 |
| 0.0046 | 22435 | 18765 | 26860 | 23215 | 13903 | 13795 |
| 0.0046 | 17613 | 22306 | 23633 | 21213 | 14095 | 10535 |

In an effort to determine if the peptides of the invention inhibited HCVpp entry at attachment or post-attachment steps, the peptide (SEQ ID NO: 77) was pre-incubated with cells at 4° C. followed by incubation with HCV pseudoparticles at 4° C. The entry process was allowed to complete after the cells were washed and incubated at 37° C. for 72 hours. If the peptide blocked or interfered with the attachment, few HCVpp particles should bind to the cells and lead to reduced luciferase signal. The peptide had approximately 50% inhibition whereas the anti-CD81 antibody inhibited entry by 20%. Alternatively, an explanation could be that the cell-associated peptide or antibody had no effects on virus attachment, but rather inhibit post-attachment steps, e.g. fusion. When we allowed the HCV pseudoparticles to attach first at 4° C., a nonpermissive temperature for fusion, and added the peptide or anti-CD81 antibody when post-attachment events occurred, anti-CD81 antibody almost inhibited entry by 100%, whereas, the peptide inhibited by approximately 80%. Our observation that anti-CD81 antibody inhibited HCVpp entry at a post-attachment step is consistent with published results (Cormier et al, Proc. Natl. Acad. Sci 101:7270-7274). Our data also indicates that the peptide largely inhibits a post-attachment step.

The incubation scheme for the fusion/attachment experiments is summarized as follows:

TABLE 23

| | | | | | | |
|---|---|---|---|---|---|---|
| A and P | cpd | →4C, 30′→ | HCVpp | →4C, 30′→ | wash → | medium + cpd, 4° C. 15′, then 37° C. |
| A | cpd | →4C, 30′→ | HCVpp | →4C, 30′→ | wash → | medium, 4° C. 15′, then 37° C. |
| P | medium | →4C, 30′→ | HCVpp | →4C, 30′→ | wash → | medium + cpd, 4° C. 15′, then 37° C. |
| No inhibition | medium | →4C, 30′→ | HCVpp | →4C, 30′→ | wash → | medium, 4° C. 15′, then 37° C. |

Data generated in fusion/attachment experiments

| RLU | V-2b (SEQ ID NO: 77) | | | average (peptide) | anti-CD81 antibody | | | average (antibody) | % control peptide | % control anti-CD81 antibody |
|---|---|---|---|---|---|---|---|---|---|---|
| A + P | 527 | 1541 | 520 | 863 | 13 | 10 | 12 | 12 | 6 | 0 |
| A | 5196 | 7987 | 4644 | 5942 | 10851 | 6692 | 9662 | 9068 | 39 | 82 |
| P | 1984 | 2412 | 545 | 1647 | 13 | 15 | 714 | 247 | 11 | 0 |
| Noinh. | 13359 | 14364 | 17778 | 15167 | 13164 | 13994 | 14957 | 14038 | 100 | 100 |

A = attachment; P = post attachment; Noinh = no inhibition

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, publications, product descriptions, and protocols are cited throughout this application, the disclosures of which are incorporated herein by reference in their entireties for all purposes.

We claim:

1. An isolated polypeptide consisting of the amino acid sequence set forth in SEQ ID NO: 81 fused to a tag selected from the group consisting of a glutathione-S-transferase (GST) tag, a hexahistidine (His6) tag, a maltose binding protein (MBP) tag, a haemagglutinin (HA) tag, a cellulose binding protein (CBP) tag and a myc tag; which is optionally
    (i) labeled with $^{32}$P, $^{35}$S, $^{3}$H, $^{99m}$Tc $^{123I}$, $^{111}$In, $^{68}$Ga, $^{18}$F, $^{125}$I, $^{131}$I, $^{113m}$In, $^{76}$Br, $^{67}$Ga, $^{99m}$Tc, $^{123}$I, $^{111}$In or $^{68}$Ga;
    (ii) fused to a polyethylene glycol molecule;
    (iii) fused to a polyethylene glycol molecule which is characterized by a molecular weight of 2 kDa, 5 kDa, 10 kDa, 12 kDa, 20 kDa, 30 kDa or 40 kDa; or
    (iv) cyclic.

2. A pharmaceutical composition comprising the polypeptide of claim 1 and a pharmaceutically acceptable carrier.

3. A composition comprising the polypeptide of claim 1 in association with one or more members selected from the group consisting of anti-human CD81 antibody, ribavirin, interferon alfa2a, interferon alfa2b, interferon alfa-2c, interferon alfa n-1, interferon alfa n-3, consensus interferon, pegylated interferon alfa-2a, pegylated interferon alfa-2b, pegylated interferon alfa-2c, pegylated interferon alfa n-1, pegylated interferon alfa n-3, and pegylated consensus interferon.

4. The composition of claim 3 comprising said polypeptide in association with interferon alfa-2b.

5. The composition of claim 3 comprising said polypeptide in association with interferon alfa-2a.

6. The composition of claim 3 comprising said polypeptide in association with pegylated interferon alfa-2b.

7. The composition of claim 3 comprising said polypeptide in association with pegylated interferon alfa-2a.

8. The composition of claim 3 comprising said polypeptide in association with ribavirin.

9. A kit comprising the polypeptide of claim 1 and a member selected from the group consisting of an anti-human CD81 antibody, ribavirin, interferon alfa-2a, interferon alfa-2b, interferon alfa-2c, interferon alfa n-1, interferon alfa n-3, consensus interferon, pegylated interferon alfa-2a, pegylated interferon alfa-2b, pegylated interferon alfa-2c, pegylated interferon alfa n-1, pegylated interferon alfa n-3, and pegylated consensus interferon.

10. The polypeptide of claim 1 which is labeled with a member selected from the group consisting of $^{32}$P, $^{35}$S, $^{3}$H, $^{99m}$Tc, $^{123}$I, $^{111}$In, $^{68}$Ga, $^{18}$F, $^{125}$I, $^{131}$I, $^{113m}$In, $^{76}$Br, $^{67}$Ga, $^{99m}$Tc, $^{123}$I, $^{111}$In and $^{68}$Ga.

11. The polypeptide of claim 1 which is fused to a polyethylene glycol molecule.

12. The polypeptide of claim 11 where the polyethylene glycol molecule comprises a molecular weight selected from the group consisting of 2 kDa, 5 kDa, 10 kDa, 12 kDa, 20 kDa, 30 kDa and 40 kDa.

13. The polypeptide of claim 1 which is cyclic.

14. The polypeptide of claim 1 consisting of the amino acid sequence set forth in SEQ ID NO: 81.

15. A polypeptide consisting of the amino acid sequence set forth in SEQ ID NO: 77; which is optionally
    (i) labeled with $^{32}$P, $^{35}$S, $^{3}$H, $^{99m}$Tc, $^{123}$I, $^{111}$In, $^{68}$Ga, $^{18}$F, $^{125}$I, $^{131}$I, $^{113m}$In, $^{76}$Br, $^{67}$Ga, $^{99m}$Tc, $^{123}$I, $^{111}$In or $^{68}$Ga;
    (ii) fused to a polyethylene glycol molecule;
    (iii) fused to a polyethylene glycol molecule which is characterized by a molecular weight of 2 kDa, 5 kDa, 10 kDa, 12 kDa, 20 kDa, 30 kDa or 40 kDa; or
    (iv) cyclic.

16. The polypeptide of claim 15 consisting of the amino acid sequence set forth in SEQ ID NO: 77.

17. The polypeptide of claim 1 fused to a tag selected from the group consisting of a glutathione-S-transferase (GST) tag, a hexahistidine (His6) tag, a maltose binding protein (MBP) tag, a haemagglutinin (HA) tag, a cellulose binding protein (CBP) tag and a myc tag.

18. A method for making a polypeptide comprising culturing a host cell comprising a vector which comprises a polynucleotide encoding a polypeptide consisting of the amino acid sequence V-S-F-A-I-K-W-E-Y-V-L-L-L-F-L-L (SEQ ID NO: 77) or A-I-K-W-E-Y-V-L-L-L-F-L-L (SEQ ID NO: 81) under conditions in which the polynucleotide is expressed.

19. The method of claim 18 wherein the polypeptide is isolated from the culture.

20. A method for inhibiting entry of a virus which is a member of the Flaviviridae family into a cell comprising contacting the cell with an isolated polypeptide consisting of the amino acid sequence set forth in SEQ ID NO: 77 or 81; which is optionally
    (i) fused to a polyethylene glycol molecule;
    (ii) fused to a polyethylene glycol molecule which is characterized by a molecular weight of 2 kDa, 5 kDa, 10 kDa, 12 kDa, 20 kDa, 30 kDa or 40 kDa; or
    (iii) cyclic.

21. The method of claim 20 wherein the cell is in vitro.

22. A method for treating infection of a subject with a virus which is a member of the Flaviviridae family comprising administering to said subject a therapeutically effective amount of an isolated polypeptide consisting of the amino acid sequence set forth in SEQ ID NO: 77 or 81; which is optionally
    (i) fused to a polyethylene glycol molecule;
    (ii) fused to a polyethylene glycol molecule which is characterized by a molecular weight of 2 kDa, 5 kDa, 10 kDa, 12 kDa, 20 kDa, 30 kDa or 40 kDa; or
    (iii) cyclic.

23. The method of claim 22 wherein the subject is a human.

24. The method of claim 22 wherein the virus is hepatitis C virus.

25. The method of claim 24, wherein the host is infected with multiple hepatitis C virus genotypes.

26. The method of claim 25, wherein the host is infected with hepatitis C virus genotype 1, hepatitis C virus genotype 2 or hepatitis C virus genotype 3.

27. The method of claim 22 wherein the polypeptide is administered to the subject parenterally.

28. The method of claim 27 wherein the polypeptide is administered to the subject intramuscularly, intravenously or subcutaneously.

29. The method of claim 22 wherein said polypeptide is administered in association with one or more members selected from the group consisting of anti-human CD81 antibody, ribavirin, interferon alfa-2a, interferon alfa-2b, interferon alfa-2c, interferon alfa n-1, interferon alfa n-3, consensus interferon, pegylated interferon alfa-2a, pegylated interferon alfa-2b, pegylated interferon alfa-2c, pegylated interferon alfa n-1, pegylated interferon alfa n-3, and pegylated consensus interferon.

30. The method of claim 18 wherein said polypeptide is administered in association with one or more members selected from the group consisting of ribavirin, interferon alfa-2a, interferon alfa-2b, pegylated interferon alfa-2a and pegylated interferon alfa-2b.

31. The method of claim 22 wherein the subject is co-infected with human immunodeficiency virus.

32. The method of claim 22 wherein the polypeptide consists of the amino acid sequence set forth in SEQ ID NO: 77.

33. The method of claim 22 wherein the polypeptide consists of the amino acid sequence set forth in SEQ TD NO: 81.

34. A method for treating infection of a subject, with a virus which is a member of the Flaviviridae family of viruses, following transplantation of a liver into said subject or transfusion of blood into said subject comprising administering to said subject a therapeutically effective amount of an isolated polypeptide consisting of the amino acid sequence set forth in SEQ ID NO: 77 or 81; which is optionally
   (i) fused to a polyethylene glycol molecule;
   (ii) fused to a polyethylene glycol molecule which is characterized by a molecular weight of 2 kDa, 5 kDa, 10 kDa, 12 kDa, 20 kDa, 30 kDa or 40 kDa; or
   (iii) cyclic.

35. The method claim 34 wherein the virus is hepatitis C virus.

36. The method of claim 34 wherein the polypeptide is administered in association with a member selected from the group consisting of anti-human CD81 antibody, ribavirin, interferon alfa2a, interferon alfa-2b, interferon alfa-2c, interferon alfa n-1, interferon alfa n-3, consensus interferon, pegylated interferon alfa-2a, pegylated interferon alfa-2b, pegylated interferon alfa-2c, pegylated interferon alfa n-1, pegylated interferon alfa n3, and pegylated consensus interferon.

37. The method of claim 34 wherein the polypeptide is administered to the subject parenterally.

38. The method of claim 37 wherein the polypeptide is administered to the subject intramuscularly, intravenously or subcutaneously.

* * * * *

```
                       SEQUENCE LISTING

<160> NUMBER OF SEQ ID NOS: 141

<210> SEQ ID NO 1
<211> LENGTH: 192
<212> TYPE: PRT
<213> ORGANISM: Hepatitis C virus

<400> SEQUENCE: 1

Tyr Gln Val Arg Asn Ser Ser Gly Leu Tyr His Val Thr Asn Asp Cys
1               5                   10                  15

Pro Asn Ser Ser Ile Val Tyr Glu Ala Ala Asp Ala Ile Leu His Thr
            20                  25                  30

Pro Gly Cys Val Pro Cys Val Arg Glu Gly Asn Ala Ser Arg Cys Trp
        35                  40                  45

Val Ala Val Thr Pro Thr Val Ala Thr Arg Asp Gly Lys Leu Pro Thr
    50                  55                  60

Thr Gln Leu Arg Arg His Ile Asp Leu Leu Val Gly Ser Ala Thr Leu
65                  70                  75                  80

Cys Ser Ala Leu Tyr Val Gly Asp Leu Cys Gly Ser Val Phe Leu Val
                85                  90                  95

Gly Gln Leu Phe Thr Phe Ser Pro Arg Arg His Trp Thr Thr Gln Asp
            100                 105                 110

Cys Asn Cys Ser Ile Tyr Pro Gly His Ile Thr Gly His Arg Met Ala
        115                 120                 125

Trp Asp Met Met Met Asn Trp Ser Pro Thr Ala Ala Leu Val Val Ala
    130                 135                 140

Gln Leu Leu Arg Ile Pro Gln Ala Ile Met Asp Met Ile Ala Gly Ala
145                 150                 155                 160
```

```
His Trp Gly Val Leu Ala Gly Ile Ala Tyr Phe Ser Met Val Gly Asn
                165                 170                 175

Trp Ala Lys Val Leu Val Val Leu Leu Leu Phe Ala Gly Val Asp Ala
            180                 185                 190

<210> SEQ ID NO 2
<211> LENGTH: 363
<212> TYPE: PRT
<213> ORGANISM: Hepatitis C virus

<400> SEQUENCE: 2

Glu Thr His Val Thr Gly Gly Ser Ala Gly Arg Thr Thr Ala Gly Leu
1               5                   10                  15

Val Gly Leu Leu Thr Pro Gly Ala Lys Gln Asn Ile Gln Leu Ile Asn
            20                  25                  30

Thr Asn Gly Ser Trp His Ile Asn Ser Thr Ala Leu Asn Cys Asn Glu
        35                  40                  45

Ser Leu Asn Thr Gly Trp Leu Ala Gly Leu Phe Tyr Gln His Lys Phe
    50                  55                  60

Asn Ser Ser Gly Cys Pro Glu Arg Leu Ala Ser Cys Arg Arg Leu Thr
65                  70                  75                  80

Asp Phe Ala Gln Gly Trp Gly Pro Ile Ser Tyr Ala Asn Gly Ser Gly
                85                  90                  95

Leu Asp Glu Arg Pro Tyr Cys Trp His Tyr Pro Pro Arg Pro Cys Gly
            100                 105                 110

Ile Val Pro Ala Lys Ser Val Cys Gly Pro Val Tyr Cys Phe Thr Pro
        115                 120                 125

Ser Pro Val Val Val Gly Thr Thr Asp Arg Ser Gly Ala Pro Thr Tyr
    130                 135                 140

Ser Trp Gly Ala Asn Asp Thr Asp Val Phe Val Leu Asn Asn Thr Arg
145                 150                 155                 160

Pro Pro Leu Gly Asn Trp Phe Gly Cys Thr Trp Met Asn Ser Thr Gly
                165                 170                 175

Phe Thr Lys Val Cys Gly Ala Pro Pro Cys Val Ile Gly Gly Val Gly
            180                 185                 190

Asn Asn Thr Leu Leu Cys Pro Thr Asp Cys Phe Arg Lys His Pro Glu
        195                 200                 205

Ala Thr Tyr Ser Arg Cys Gly Ser Gly Pro Trp Ile Thr Pro Arg Cys
    210                 215                 220

Met Val Asp Tyr Pro Tyr Arg Leu Trp His Tyr Pro Cys Thr Ile Asn
225                 230                 235                 240

Tyr Thr Ile Phe Lys Val Arg Met Tyr Val Gly Gly Val Glu His Arg
                245                 250                 255

Leu Glu Ala Ala Cys Asn Trp Thr Arg Gly Glu Arg Cys Asp Leu Glu
            260                 265                 270

Asp Arg Asp Arg Ser Glu Leu Ser Pro Leu Leu Leu Ser Thr Thr Gln
        275                 280                 285

Trp Gln Val Leu Pro Cys Ser Phe Thr Thr Leu Pro Ala Leu Ser Thr
    290                 295                 300

Gly Leu Ile His Leu His Gln Asn Ile Val Asp Val Gln Tyr Leu Tyr
305                 310                 315                 320

Gly Val Gly Ser Ser Ile Ala Ser Trp Ala Ile Lys Trp Glu Tyr Val
                325                 330                 335

Val Leu Leu Phe Leu Leu Leu Ala Asp Ala Arg Val Cys Ser Cys Leu
```

```
                340                 345                 350
Trp Met Met Leu Leu Ile Ser Gln Ala Glu Ala
        355                 360

<210> SEQ ID NO 3
<211> LENGTH: 16
<212> TYPE: PRT
<213> ORGANISM: Artificial Sequence
<220> FEATURE:
<223> OTHER INFORMATION: HCV peptide

<400> SEQUENCE: 3

Tyr Glu Val Arg Asn Val Ser Gly Val Tyr His Val Thr Asn Asp Cys
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: HCV peptide

<400> SEQUENCE: 4

Gly Val Tyr His Val Thr Asn Asp Cys Ser Asn Ala Ser Ile Val Tyr
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: HCV peptide

<400> SEQUENCE: 5

Asp Cys Ser Asn Ala Ser Ile Val Tyr Glu Ala Ala Asp Met Ile Met
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: HCV peptide

<400> SEQUENCE: 6

Val Tyr Glu Ala Ala Asp Met Ile Met His Thr Pro Gly Cys Val Pro
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: HCV peptide

<400> SEQUENCE: 7

Ile Met His Thr Pro Gly Cys Val Pro Cys Val Arg Glu Asn Asn Ser
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: HCV peptide

<400> SEQUENCE: 8
```

```
Val Pro Cys Val Arg Glu Asn Asn Ser Ser Arg Cys Trp Val Ala Leu
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: HCV peptide

<400> SEQUENCE: 9

Asn Ser Ser Arg Cys Trp Val Ala Leu Thr Pro Thr Leu Ala Ala Arg
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: HCV peptide

<400> SEQUENCE: 10

Ala Leu Thr Pro Thr Leu Ala Ala Arg Asn Ala Ser Val Pro Thr Thr
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: HCV peptide

<400> SEQUENCE: 11

Ala Arg Asn Ala Ser Val Pro Thr Thr Thr Ile Arg Arg His Val Asp
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: HCV peptide

<400> SEQUENCE: 12

Thr Thr Thr Ile Arg Arg His Val Asp Leu Leu Val Gly Ala Ala Ala
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: HCV peptide

<400> SEQUENCE: 13

Val Asp Leu Leu Val Gly Ala Ala Ala Leu Cys Ser Ala Met Tyr Val
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: HCV peptide

<400> SEQUENCE: 14
```

```
Ala Ala Leu Cys Ser Ala Met Tyr Val Gly Asp Leu Cys Gly Ser Val
1               5                   10                  15
```

<210> SEQ ID NO 15
<211> LENGTH: 16
<212> TYPE: PRT
<213> ORGANISM: Artificial Sequence
<220> FEATURE:
<223> OTHER INFORMATION: HCV peptide

<400> SEQUENCE: 15

```
Tyr Val Gly Asp Leu Cys Gly Ser Val Phe Leu Val Ala Gln Leu Phe
1               5                   10                  15
```

<210> SEQ ID NO 16
<211> LENGTH: 16
<212> TYPE: PRT
<213> ORGANISM: Artificial Sequence
<220> FEATURE:
<223> OTHER INFORMATION: HCV peptide

<400> SEQUENCE: 16

```
Ser Val Phe Leu Val Ala Gln Leu Phe Thr Phe Ser Pro Arg Arg His
1               5                   10                  15
```

<210> SEQ ID NO 17
<211> LENGTH: 16
<212> TYPE: PRT
<213> ORGANISM: Artificial Sequence
<220> FEATURE:
<223> OTHER INFORMATION: HCV peptide

<400> SEQUENCE: 17

```
Leu Phe Thr Phe Ser Pro Arg Arg His Glu Thr Val Gln Asp Cys Asn
1               5                   10                  15
```

<210> SEQ ID NO 18
<211> LENGTH: 16
<212> TYPE: PRT
<213> ORGANISM: Artificial Sequence
<220> FEATURE:
<223> OTHER INFORMATION: HCV peptide

<400> SEQUENCE: 18

```
Arg His Glu Thr Val Gln Asp Cys Asn Cys Ser Ile Tyr Pro Gly His
1               5                   10                  15
```

<210> SEQ ID NO 19
<211> LENGTH: 16
<212> TYPE: PRT
<213> ORGANISM: Artificial Sequence
<220> FEATURE:
<223> OTHER INFORMATION: HCV peptide

<400> SEQUENCE: 19

```
Cys Asn Cys Ser Ile Tyr Pro Gly His Val Thr Gly His Arg Met Ala
1               5                   10                  15
```

<210> SEQ ID NO 20
<211> LENGTH: 16
<212> TYPE: PRT
<213> ORGANISM: Artificial Sequence
<220> FEATURE:
<223> OTHER INFORMATION: HCV peptide

<400> SEQUENCE: 20

```
Gly His Val Thr Gly His Arg Met Ala Trp Asp Met Met Met Asn Trp
```

-continued

```
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: HCV peptide

<400> SEQUENCE: 21

Met Ala Trp Asp Met Met Met Asn Trp Ser Pro Thr Ala Ala Leu Val
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: HCV peptide

<400> SEQUENCE: 22

Asn Trp Ser Pro Thr Ala Ala Leu Val Val Ser Gln Leu Leu Arg Ile
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: HCV peptide

<400> SEQUENCE: 23

Leu Val Val Ser Gln Leu Leu Arg Ile Pro Gln Ala Val Val Asp Met
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: HCV peptide

<400> SEQUENCE: 24

Arg Ile Pro Gln Ala Val Val Asp Met Val Ala Gly Ala His Trp Gly
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: HCV peptide

<400> SEQUENCE: 25

Asp Met Val Ala Gly Ala His Trp Gly Val Leu Ala Gly Leu Ala Tyr
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: HCV peptide

<400> SEQUENCE: 26

Trp Gly Val Leu Ala Gly Leu Ala Tyr Tyr Ser Met Val Gly Asn Trp
1               5                   10                  15
```

```
<210> SEQ ID NO 27
<211> LENGTH: 16
<212> TYPE: PRT
<213> ORGANISM: Artificial Sequence
<220> FEATURE:
<223> OTHER INFORMATION: HCV peptide

<400> SEQUENCE: 27

Ala Tyr Tyr Ser Met Val Gly Asn Trp Ala Lys Val Leu Ile Val Met
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: HCV peptide

<400> SEQUENCE: 28

Asn Trp Ala Lys Val Leu Ile Val Met Leu Leu Phe Ala Gly Val Asp
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: HCV peptide

<400> SEQUENCE: 29

Val Met Leu Leu Phe Ala Gly Val Asp Gly Gly Thr Tyr Val Thr Gly
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: HCV peptide

<400> SEQUENCE: 30

Val Asp Gly Gly Thr Tyr Val Thr Gly Gly Thr Met Ala Lys Asn Thr
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: HCV peptide

<400> SEQUENCE: 31

Thr Gly Gly Thr Met Ala Lys Asn Thr Leu Gly Ile Thr Ser Leu Phe
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: HCV peptide

<400> SEQUENCE: 32

Asn Thr Leu Gly Ile Thr Ser Leu Phe Ser Pro Gly Ser Ser Gln Lys
1               5                   10                  15
```

```
<210> SEQ ID NO 33
<211> LENGTH: 16
<212> TYPE: PRT
<213> ORGANISM: Artificial Sequence
<220> FEATURE:
<223> OTHER INFORMATION: HCV peptide

<400> SEQUENCE: 33

Leu Phe Ser Pro Gly Ser Ser Gln Lys Ile Gln Leu Val Asn Thr Asn
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: HCV peptide

<400> SEQUENCE: 34

Gln Lys Ile Gln Leu Val Asn Thr Asn Gly Ser Trp His Ile Asn Arg
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: HCV peptide

<400> SEQUENCE: 35

Thr Asn Gly Ser Trp His Ile Asn Arg Thr Ala Leu Asn Cys Asn Asp
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: HCV peptide

<400> SEQUENCE: 36

Asn Arg Thr Ala Leu Asn Cys Asn Asp Ser Leu Asn Thr Gly Phe Leu
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: HCV peptide

<400> SEQUENCE: 37

Asn Asp Ser Leu Asn Thr Gly Phe Leu Ala Ala Leu Phe Tyr Val His
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: HCV peptide

<400> SEQUENCE: 38

Phe Leu Ala Ala Leu Phe Tyr Val His Lys Phe Asn Ser Ser Gly Cys
1               5                   10                  15
```

<210> SEQ ID NO 39
<211> LENGTH: 16
<212> TYPE: PRT
<213> ORGANISM: Artificial Sequence
<220> FEATURE:
<223> OTHER INFORMATION: HCV peptide

<400> SEQUENCE: 39

Val His Lys Phe Asn Ser Ser Gly Cys Pro Glu Arg Met Ala Ser Cys
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: HCV peptide

<400> SEQUENCE: 40

Gly Cys Pro Glu Arg Met Ala Ser Cys Ser Pro Ile Asp Ala Phe Ala
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: HCV peptide

<400> SEQUENCE: 41

Ser Cys Ser Pro Ile Asp Ala Phe Ala Gln Gly Trp Gly Pro Ile Thr
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: HCV peptide

<400> SEQUENCE: 42

Phe Ala Gln Gly Trp Gly Pro Ile Thr Tyr Asn Glu Ser His Ser Ser
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: HCV peptide

<400> SEQUENCE: 43

Ile Thr Tyr Asn Glu Ser His Ser Ser Asp Gln Arg Pro Tyr Cys Trp
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: HCV peptide

<400> SEQUENCE: 44

Ser Ser Asp Gln Arg Pro Tyr Cys Trp His Tyr Ala Pro Arg Pro Cys
1               5                   10                  15

<210> SEQ ID NO 45

```
<211> LENGTH: 16
<212> TYPE: PRT
<213> ORGANISM: Artificial Sequence
<220> FEATURE:
<223> OTHER INFORMATION: HCV peptide

<400> SEQUENCE: 45

Cys Trp His Tyr Ala Pro Arg Pro Cys Gly Ile Val Pro Ala Ala Gln
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: HCV peptide

<400> SEQUENCE: 46

Pro Cys Gly Ile Val Pro Ala Ala Gln Val Cys Gly Pro Val Tyr Cys
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: HCV peptide

<400> SEQUENCE: 47

Ala Gln Val Cys Gly Pro Val Tyr Cys Phe Thr Pro Ser Pro Val Val
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: HCV peptide

<400> SEQUENCE: 48

Tyr Cys Phe Thr Pro Ser Pro Val Val Val Gly Thr Thr Asp Arg Phe
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: HCV peptide

<400> SEQUENCE: 49

Val Val Val Gly Thr Thr Asp Arg Phe Gly Val Pro Thr Tyr Ser Trp
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: HCV peptide

<400> SEQUENCE: 50

Arg Phe Gly Val Pro Thr Tyr Ser Trp Gly Glu Asn Glu Thr Asp Val
1               5                   10                  15

<210> SEQ ID NO 51
<211> LENGTH: 16
```

```
<212> TYPE: PRT
<213> ORGANISM: Artificial Sequence
<220> FEATURE:
<223> OTHER INFORMATION: HCV peptide

<400> SEQUENCE: 51

Ser Trp Gly Glu Asn Glu Thr Asp Val Leu Leu Leu Asn Asn Thr Arg
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: HCV peptide

<400> SEQUENCE: 52

Asp Val Leu Leu Leu Asn Asn Thr Arg Pro Pro Gln Gly Asn Trp Phe
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: HCV peptide

<400> SEQUENCE: 53

Thr Arg Pro Pro Gln Gly Asn Trp Phe Gly Cys Thr Trp Met Asn Ser
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: HCV peptide

<400> SEQUENCE: 54

Trp Phe Gly Cys Thr Trp Met Asn Ser Thr Gly Phe Thr Lys Thr Cys
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: HCV peptide

<400> SEQUENCE: 55

Asn Ser Thr Gly Phe Thr Lys Thr Cys Gly Gly Pro Pro Cys Asn Ile
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: HCV peptide

<400> SEQUENCE: 56

Thr Cys Gly Gly Pro Pro Cys Asn Ile Gly Gly Ile Gly Asn Lys Thr
1               5                   10                  15

<210> SEQ ID NO 57
<211> LENGTH: 16
<212> TYPE: PRT
```

```
<213> ORGANISM: Artificial Sequence
<220> FEATURE:
<223> OTHER INFORMATION: HCV peptide

<400> SEQUENCE: 57

Asn Ile Gly Gly Ile Gly Asn Lys Thr Leu Thr Cys Pro Thr Asp Cys
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: HCV peptide

<400> SEQUENCE: 58

Lys Thr Leu Thr Cys Pro Thr Asp Cys Phe Arg Lys His Pro Glu Ala
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: HCV peptide

<400> SEQUENCE: 59

Asp Cys Phe Arg Lys His Pro Glu Ala Thr Tyr Thr Lys Cys Gly Ser
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: HCV peptide

<400> SEQUENCE: 60

Glu Ala Thr Tyr Thr Lys Cys Gly Ser Gly Pro Trp Leu Thr Pro Arg
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: HCV peptide

<400> SEQUENCE: 61

Gly Ser Gly Pro Trp Leu Thr Pro Arg Cys Leu Val His Tyr Pro Tyr
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: HCV peptide

<400> SEQUENCE: 62

Pro Arg Cys Leu Val His Tyr Pro Tyr Arg Leu Trp His Tyr Pro Cys
1               5                   10                  15

<210> SEQ ID NO 63
<211> LENGTH: 16
<212> TYPE: PRT
<213> ORGANISM: Artificial Sequence
```

-continued

<220> FEATURE:
<223> OTHER INFORMATION: HCV peptide

<400> SEQUENCE: 63

Pro Tyr Arg Leu Trp His Tyr Pro Cys Thr Val Asn Phe Thr Ile Phe
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: HCV peptide

<400> SEQUENCE: 64

Pro Cys Thr Val Asn Phe Thr Ile Phe Lys Val Arg Met Tyr Val Gly
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: HCV peptide

<400> SEQUENCE: 65

Ile Phe Lys Val Arg Met Tyr Val Gly Gly Val Glu His Arg Leu Glu
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: HCV peptide

<400> SEQUENCE: 66

Val Gly Gly Val Glu His Arg Leu Glu Ala Ala Cys Asn Trp Thr Arg
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: HCV peptide

<400> SEQUENCE: 67

Leu Glu Ala Ala Cys Asn Trp Thr Arg Gly Glu Arg Cys Asn Leu Glu
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: HCV peptide

<400> SEQUENCE: 68

Thr Arg Gly Glu Arg Cys Asn Leu Glu Asp Arg Asp Arg Ser Glu Leu
1               5                   10                  15

<210> SEQ ID NO 69
<211> LENGTH: 16
<212> TYPE: PRT
<213> ORGANISM: Artificial Sequence
<220> FEATURE:

```
<223> OTHER INFORMATION: HCV peptide

<400> SEQUENCE: 69

Leu Glu Asp Arg Asp Arg Ser Glu Leu Ser Pro Leu Leu Ser Thr
1               5                   10                  15

<210> SEQ ID NO 70
<211> LENGTH: 16
<212> TYPE: PRT
<213> ORGANISM: Artificial Sequence
<220> FEATURE:
<223> OTHER INFORMATION: HCV peptide

<400> SEQUENCE: 70

Glu Leu Ser Pro Leu Leu Leu Ser Thr Thr Glu Trp Gln Val Leu Pro
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: HCV peptide

<400> SEQUENCE: 71

Ser Thr Thr Glu Trp Gln Val Leu Pro Cys Ser Phe Thr Thr Leu Pro
1               5                   10                  15

<210> SEQ ID NO 72
<211> LENGTH: 16
<212> TYPE: PRT
<213> ORGANISM: Artificial Sequence
<220> FEATURE:
<223> OTHER INFORMATION: HCV peptide

<400> SEQUENCE: 72

Leu Pro Cys Ser Phe Thr Thr Leu Pro Ala Leu Ser Thr Gly Leu Ile
1               5                   10                  15

<210> SEQ ID NO 73
<211> LENGTH: 16
<212> TYPE: PRT
<213> ORGANISM: Artificial Sequence
<220> FEATURE:
<223> OTHER INFORMATION: HCV peptide

<400> SEQUENCE: 73

Leu Pro Ala Leu Ser Thr Gly Leu Ile His Leu His Gln Asn Val Val
1               5                   10                  15

<210> SEQ ID NO 74
<211> LENGTH: 16
<212> TYPE: PRT
<213> ORGANISM: Artificial Sequence
<220> FEATURE:
<223> OTHER INFORMATION: HCV peptide

<400> SEQUENCE: 74

Leu Ile His Leu His Gln Asn Val Val Asp Val Gln Tyr Leu Tyr Gly
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: HCV peptide
```

<400> SEQUENCE: 75

Val Val Asp Val Gln Tyr Leu Tyr Gly Ile Gly Ser Ala Val Val Ser
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: HCV peptide

<400> SEQUENCE: 76

Tyr Gly Ile Gly Ser Ala Val Val Ser Phe Ala Ile Lys Trp Glu Tyr
1               5                   10                  15

<210> SEQ ID NO 77
<211> LENGTH: 16
<212> TYPE: PRT
<213> ORGANISM: Artificial Sequence
<220> FEATURE:
<223> OTHER INFORMATION: HCV peptide

<400> SEQUENCE: 77

Val Ser Phe Ala Ile Lys Trp Glu Tyr Val Leu Leu Leu Phe Leu Leu
1               5                   10                  15

<210> SEQ ID NO 78
<211> LENGTH: 16
<212> TYPE: PRT
<213> ORGANISM: Artificial Sequence
<220> FEATURE:
<223> OTHER INFORMATION: HCV peptide

<400> SEQUENCE: 78

Glu Tyr Val Leu Leu Leu Phe Leu Leu Leu Ala Asp Ala Arg Val Cys
1               5                   10                  15

<210> SEQ ID NO 79
<211> LENGTH: 16
<212> TYPE: PRT
<213> ORGANISM: Artificial Sequence
<220> FEATURE:
<223> OTHER INFORMATION: HCV peptide

<400> SEQUENCE: 79

Leu Leu Leu Ala Asp Ala Arg Val Cys Ala Cys Leu Trp Met Met Leu
1               5                   10                  15

<210> SEQ ID NO 80
<211> LENGTH: 16
<212> TYPE: PRT
<213> ORGANISM: Artificial Sequence
<220> FEATURE:
<223> OTHER INFORMATION: HCV peptide

<400> SEQUENCE: 80

Val Cys Ala Cys Leu Trp Met Met Leu Leu Ile Ala Gln Ala Glu Ala
1               5                   10                  15

<210> SEQ ID NO 81
<211> LENGTH: 13
<212> TYPE: PRT
<213> ORGANISM: Artificial Sequence
<220> FEATURE:
<223> OTHER INFORMATION: HCV peptide

```
<400> SEQUENCE: 81

Ala Ile Lys Trp Glu Tyr Val Leu Leu Leu Phe Leu Leu
1               5                   10

<210> SEQ ID NO 82
<211> LENGTH: 13
<212> TYPE: PRT
<213> ORGANISM: Artificial Sequence
<220> FEATURE:
<223> OTHER INFORMATION: HCV peptide

<400> SEQUENCE: 82

Gly Ile Lys Trp Glu Tyr Val Leu Leu Leu Phe Leu Leu
1               5                   10

<210> SEQ ID NO 83
<211> LENGTH: 13
<212> TYPE: PRT
<213> ORGANISM: Artificial Sequence
<220> FEATURE:
<223> OTHER INFORMATION: HCV peptide

<400> SEQUENCE: 83

Ala Gly Lys Trp Glu Tyr Val Leu Leu Leu Phe Leu Leu
1               5                   10

<210> SEQ ID NO 84
<211> LENGTH: 13
<212> TYPE: PRT
<213> ORGANISM: Artificial Sequence
<220> FEATURE:
<223> OTHER INFORMATION: HCV peptide

<400> SEQUENCE: 84

Ala Ile Lys Trp Gly Tyr Val Leu Leu Leu Phe Leu Leu
1               5                   10

<210> SEQ ID NO 85
<211> LENGTH: 13
<212> TYPE: PRT
<213> ORGANISM: Artificial Sequence
<220> FEATURE:
<223> OTHER INFORMATION: HCV peptide

<400> SEQUENCE: 85

Ala Ile Lys Trp Glu Tyr Val Leu Leu Leu Phe Leu Leu
1               5                   10

<210> SEQ ID NO 86
<211> LENGTH: 13
<212> TYPE: PRT
<213> ORGANISM: Artificial Sequence
<220> FEATURE:
<223> OTHER INFORMATION: HCV peptide

<400> SEQUENCE: 86

Ala Ile Lys Trp Glu Tyr Val Leu Leu Leu Phe Leu Leu
1               5                   10

<210> SEQ ID NO 87
<211> LENGTH: 13
<212> TYPE: PRT
<213> ORGANISM: Artificial Sequence
<220> FEATURE:
<223> OTHER INFORMATION: HCV peptide

<400> SEQUENCE: 87
```

-continued

Ala Ala Lys Trp Glu Tyr Val Leu Leu Leu Phe Leu Leu
1               5                   10

<210> SEQ ID NO 88
<211> LENGTH: 13
<212> TYPE: PRT
<213> ORGANISM: Artificial Sequence
<220> FEATURE:
<223> OTHER INFORMATION: HCV peptide

<400> SEQUENCE: 88

Ala Ile Ala Trp Glu Tyr Val Leu Leu Leu Phe Leu Leu
1               5                   10

<210> SEQ ID NO 89
<211> LENGTH: 13
<212> TYPE: PRT
<213> ORGANISM: Artificial Sequence
<220> FEATURE:
<223> OTHER INFORMATION: HCV peptide

<400> SEQUENCE: 89

Ala Ile Lys Ala Glu Tyr Val Leu Leu Leu Phe Leu Leu
1               5                   10

<210> SEQ ID NO 90
<211> LENGTH: 13
<212> TYPE: PRT
<213> ORGANISM: Artificial Sequence
<220> FEATURE:
<223> OTHER INFORMATION: HCV peptide

<400> SEQUENCE: 90

Ala Ile Lys Trp Ala Tyr Val Leu Leu Leu Phe Leu Leu
1               5                   10

<210> SEQ ID NO 91
<211> LENGTH: 13
<212> TYPE: PRT
<213> ORGANISM: Artificial Sequence
<220> FEATURE:
<223> OTHER INFORMATION: HCV peptide

<400> SEQUENCE: 91

Ala Ile Lys Trp Glu Ala Val Leu Leu Leu Phe Leu Leu
1               5                   10

<210> SEQ ID NO 92
<211> LENGTH: 13
<212> TYPE: PRT
<213> ORGANISM: Artificial Sequence
<220> FEATURE:
<223> OTHER INFORMATION: HCV peptide

<400> SEQUENCE: 92

Ala Ile Lys Trp Glu Tyr Ala Leu Leu Leu Phe Leu Leu
1               5                   10

<210> SEQ ID NO 93
<211> LENGTH: 13
<212> TYPE: PRT
<213> ORGANISM: Artificial Sequence
<220> FEATURE:
<223> OTHER INFORMATION: HCV peptide

<400> SEQUENCE: 93

```
Ala Ile Lys Trp Glu Tyr Val Ala Leu Leu Phe Leu Leu
 1               5                   10
```

<210> SEQ ID NO 94
<211> LENGTH: 13
<212> TYPE: PRT
<213> ORGANISM: Artificial Sequence
<220> FEATURE:
<223> OTHER INFORMATION: HCV peptide

<400> SEQUENCE: 94

```
Ala Ile Lys Trp Glu Tyr Val Leu Ala Leu Phe Leu Leu
 1               5                   10
```

<210> SEQ ID NO 95
<211> LENGTH: 13
<212> TYPE: PRT
<213> ORGANISM: Artificial Sequence
<220> FEATURE:
<223> OTHER INFORMATION: HCV peptide

<400> SEQUENCE: 95

```
Ala Ile Lys Trp Glu Tyr Val Leu Leu Leu Ala Leu Leu
 1               5                   10
```

<210> SEQ ID NO 96
<211> LENGTH: 13
<212> TYPE: PRT
<213> ORGANISM: Artificial Sequence
<220> FEATURE:
<223> OTHER INFORMATION: HCV peptide

<400> SEQUENCE: 96

```
Ala Ile Lys Trp Glu Tyr Val Leu Leu Leu Phe Ala Leu
 1               5                   10
```

<210> SEQ ID NO 97
<211> LENGTH: 13
<212> TYPE: PRT
<213> ORGANISM: Artificial Sequence
<220> FEATURE:
<223> OTHER INFORMATION: HCV peptide

<400> SEQUENCE: 97

```
Ala Ile Lys Trp Glu Tyr Val Leu Leu Leu Phe Leu Ala
 1               5                   10
```

<210> SEQ ID NO 98
<211> LENGTH: 13
<212> TYPE: PRT
<213> ORGANISM: Artificial Sequence
<220> FEATURE:
<223> OTHER INFORMATION: HCV peptide

<400> SEQUENCE: 98

```
Ala Ile Lys Trp Glu Tyr Val Leu Leu Leu Phe Leu Leu
 1               5                   10
```

<210> SEQ ID NO 99
<211> LENGTH: 13
<212> TYPE: PRT
<213> ORGANISM: Artificial Sequence
<220> FEATURE:
<223> OTHER INFORMATION: HCV peptide

<400> SEQUENCE: 99

```
Pro Ile Lys Trp Glu Tyr Val Leu Leu Leu Phe Leu Leu
```

```
<210> SEQ ID NO 100
<211> LENGTH: 13
<212> TYPE: PRT
<213> ORGANISM: Artificial Sequence
<220> FEATURE:
<223> OTHER INFORMATION: HCV peptide

<400> SEQUENCE: 100

Ala Ile Lys Trp Glu Tyr Val Leu Leu Leu Phe Leu Leu
1               5                   10

<210> SEQ ID NO 101
<211> LENGTH: 13
<212> TYPE: PRT
<213> ORGANISM: Artificial Sequence
<220> FEATURE:
<223> OTHER INFORMATION: HCV peptide

<400> SEQUENCE: 101

Lys Ile Lys Trp Glu Tyr Val Leu Leu Leu Phe Leu Leu
1               5                   10

<210> SEQ ID NO 102
<211> LENGTH: 13
<212> TYPE: PRT
<213> ORGANISM: Artificial Sequence
<220> FEATURE:
<223> OTHER INFORMATION: HCV peptide

<400> SEQUENCE: 102

Ala Lys Lys Trp Glu Tyr Val Leu Leu Leu Phe Leu Leu
1               5                   10

<210> SEQ ID NO 103
<211> LENGTH: 13
<212> TYPE: PRT
<213> ORGANISM: Artificial Sequence
<220> FEATURE:
<223> OTHER INFORMATION: HCV peptide

<400> SEQUENCE: 103

Ala Ile Lys Trp Lys Tyr Val Leu Leu Leu Phe Leu Leu
1               5                   10

<210> SEQ ID NO 104
<211> LENGTH: 15
<212> TYPE: PRT
<213> ORGANISM: Artificial Sequence
<220> FEATURE:
<223> OTHER INFORMATION: HCV peptide

<400> SEQUENCE: 104

Ser Phe Ala Ile Lys Trp Glu Tyr Val Leu Leu Leu Phe Leu Leu
1               5                   10                  15

<210> SEQ ID NO 105
<211> LENGTH: 14
<212> TYPE: PRT
<213> ORGANISM: Artificial Sequence
<220> FEATURE:
<223> OTHER INFORMATION: HCV peptide

<400> SEQUENCE: 105

Phe Ala Ile Lys Trp Glu Tyr Val Leu Leu Leu Phe Leu Leu
1               5                   10
```

```
<210> SEQ ID NO 106
<211> LENGTH: 13
<212> TYPE: PRT
<213> ORGANISM: Artificial Sequence
<220> FEATURE:
<223> OTHER INFORMATION: HCV peptide

<400> SEQUENCE: 106

Ala Ile Lys Trp Glu Tyr Val Leu Leu Leu Phe Leu Leu
1               5                   10

<210> SEQ ID NO 107
<211> LENGTH: 12
<212> TYPE: PRT
<213> ORGANISM: Artificial Sequence
<220> FEATURE:
<223> OTHER INFORMATION: HCV peptide

<400> SEQUENCE: 107

Ile Lys Trp Glu Tyr Val Leu Leu Leu Phe Leu Leu
1               5                   10

<210> SEQ ID NO 108
<211> LENGTH: 11
<212> TYPE: PRT
<213> ORGANISM: Artificial Sequence
<220> FEATURE:
<223> OTHER INFORMATION: HCV peptide

<400> SEQUENCE: 108

Lys Trp Glu Tyr Val Leu Leu Leu Phe Leu Leu
1               5                   10

<210> SEQ ID NO 109
<211> LENGTH: 10
<212> TYPE: PRT
<213> ORGANISM: Artificial Sequence
<220> FEATURE:
<223> OTHER INFORMATION: HCV peptide

<400> SEQUENCE: 109

Trp Glu Tyr Val Leu Leu Leu Phe Leu Leu
1               5                   10

<210> SEQ ID NO 110
<211> LENGTH: 16
<212> TYPE: PRT
<213> ORGANISM: Artificial  Sequence
<220> FEATURE:
<223> OTHER INFORMATION: HCV peptide

<400> SEQUENCE: 110

Val Ser Phe Ala Ile Lys Trp Glu Tyr Val Leu Leu Leu Phe Leu Leu
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: HCV peptide

<400> SEQUENCE: 111

Val Ser Phe Ala Ile Lys Trp Glu Tyr Val Leu Leu Leu Phe Leu
1               5                   10                  15
```

```
<210> SEQ ID NO 112
<211> LENGTH: 14
<212> TYPE: PRT
<213> ORGANISM: Artificial Sequence
<220> FEATURE:
<223> OTHER INFORMATION: HCV peptide

<400> SEQUENCE: 112

Val Ser Phe Ala Ile Lys Trp Glu Tyr Val Leu Leu Leu Phe
1               5                   10

<210> SEQ ID NO 113
<211> LENGTH: 13
<212> TYPE: PRT
<213> ORGANISM: Artificial  Sequence
<220> FEATURE:
<223> OTHER INFORMATION: HCV peptide

<400> SEQUENCE: 113

Val Ser Phe Ala Ile Lys Trp Glu Tyr Val Leu Leu Leu
1               5                   10

<210> SEQ ID NO 114
<211> LENGTH: 12
<212> TYPE: PRT
<213> ORGANISM: Artificial Sequence
<220> FEATURE:
<223> OTHER INFORMATION: HCV peptide

<400> SEQUENCE: 114

Val Ser Phe Ala Ile Lys Trp Glu Tyr Val Leu Leu
1               5                   10

<210> SEQ ID NO 115
<211> LENGTH: 11
<212> TYPE: PRT
<213> ORGANISM: Artificial Sequence
<220> FEATURE:
<223> OTHER INFORMATION: HCV peptide

<400> SEQUENCE: 115

Val Ser Phe Ala Ile Lys Trp Glu Tyr Val Leu
1               5                   10

<210> SEQ ID NO 116
<211> LENGTH: 10
<212> TYPE: PRT
<213> ORGANISM: Artificial Sequence
<220> FEATURE:
<223> OTHER INFORMATION: HCV peptide

<400> SEQUENCE: 116

Val Ser Phe Ala Ile Lys Trp Glu Tyr Val
1               5                   10

<210> SEQ ID NO 117
<211> LENGTH: 13
<212> TYPE: PRT
<213> ORGANISM: Artificial Sequence
<220> FEATURE:
<223> OTHER INFORMATION: HCV peptide

<400> SEQUENCE: 117

Ala Ile Pro Trp Glu Tyr Val Leu Leu Leu Phe Leu Leu
1               5                   10
```

```
<210> SEQ ID NO 118
<211> LENGTH: 13
<212> TYPE: PRT
<213> ORGANISM: Artificial Sequence
<220> FEATURE:
<223> OTHER INFORMATION: HCV peptide

<400> SEQUENCE: 118

Ala Ile Lys Pro Glu Tyr Val Leu Leu Leu Phe Leu Leu
1               5                   10

<210> SEQ ID NO 119
<211> LENGTH: 13
<212> TYPE: PRT
<213> ORGANISM: Artificial Sequence
<220> FEATURE:
<223> OTHER INFORMATION: HCV peptide

<400> SEQUENCE: 119

Ala Ile Lys Trp Pro Tyr Val Leu Leu Leu Phe Leu Leu
1               5                   10

<210> SEQ ID NO 120
<211> LENGTH: 13
<212> TYPE: PRT
<213> ORGANISM: Artificial Sequence
<220> FEATURE:
<223> OTHER INFORMATION: HCV peptide

<400> SEQUENCE: 120

Ala Ile Lys Trp Glu Pro Val Leu Leu Leu Phe Leu Leu
1               5                   10

<210> SEQ ID NO 121
<211> LENGTH: 13
<212> TYPE: PRT
<213> ORGANISM: Artificial Sequence
<220> FEATURE:
<223> OTHER INFORMATION: HCV peptide

<400> SEQUENCE: 121

Ala Ile Lys Trp Glu Tyr Pro Leu Leu Leu Phe Leu Leu
1               5                   10

<210> SEQ ID NO 122
<211> LENGTH: 13
<212> TYPE: PRT
<213> ORGANISM: Artificial Sequence
<220> FEATURE:
<223> OTHER INFORMATION: HCV peptide

<400> SEQUENCE: 122

Ala Ile Lys Trp Glu Tyr Val Pro Leu Leu Phe Leu Leu
1               5                   10

<210> SEQ ID NO 123
<211> LENGTH: 13
<212> TYPE: PRT
<213> ORGANISM: Artificial Sequence
<220> FEATURE:
<223> OTHER INFORMATION: HCV peptide

<400> SEQUENCE: 123

Ala Ile Lys Trp Glu Tyr Val Leu Pro Leu Phe Leu Leu
1               5                   10

<210> SEQ ID NO 124
```

```
<211> LENGTH: 13
<212> TYPE: PRT
<213> ORGANISM: Artificial Sequence
<220> FEATURE:
<223> OTHER INFORMATION: HCV peptide

<400> SEQUENCE: 124

Ala Ile Lys Trp Glu Tyr Val Leu Leu Pro Phe Leu Leu
1               5                   10

<210> SEQ ID NO 125
<211> LENGTH: 13
<212> TYPE: PRT
<213> ORGANISM: Artificial Sequence
<220> FEATURE:
<223> OTHER INFORMATION: HCV peptide

<400> SEQUENCE: 125

Ala Ile Lys Trp Glu Tyr Val Leu Leu Leu Pro Leu Leu
1               5                   10

<210> SEQ ID NO 126
<211> LENGTH: 13
<212> TYPE: PRT
<213> ORGANISM: Artificial Sequence
<220> FEATURE:
<223> OTHER INFORMATION: HCV peptide

<400> SEQUENCE: 126

Ala Ile Lys Trp Glu Tyr Val Leu Leu Leu Phe Pro Leu
1               5                   10

<210> SEQ ID NO 127
<211> LENGTH: 13
<212> TYPE: PRT
<213> ORGANISM: Artificial Sequence
<220> FEATURE:
<223> OTHER INFORMATION: HCV peptide

<400> SEQUENCE: 127

Ala Ile Lys Trp Glu Tyr Val Leu Leu Leu Phe Leu Pro
1               5                   10

<210> SEQ ID NO 128
<211> LENGTH: 13
<212> TYPE: PRT
<213> ORGANISM: Artificial Sequence
<220> FEATURE:
<223> OTHER INFORMATION: HCV peptide

<400> SEQUENCE: 128

Ala Ile Lys Lys Glu Tyr Val Leu Leu Leu Phe Leu Leu
1               5                   10

<210> SEQ ID NO 129
<211> LENGTH: 13
<212> TYPE: PRT
<213> ORGANISM: Artificial  Sequence
<220> FEATURE:
<223> OTHER INFORMATION: HCV peptide

<400> SEQUENCE: 129

Ala Ile Lys Trp Lys Tyr Val Leu Leu Leu Phe Leu Leu
1               5                   10

<210> SEQ ID NO 130
<211> LENGTH: 13
```

```
<212> TYPE: PRT
<213> ORGANISM: Artificial Sequence
<220> FEATURE:
<223> OTHER INFORMATION: HCV peptide

<400> SEQUENCE: 130

Ala Ile Lys Trp Glu Lys Val Leu Leu Phe Leu Leu
1               5                   10

<210> SEQ ID NO 131
<211> LENGTH: 13
<212> TYPE: PRT
<213> ORGANISM: Artificial Sequence
<220> FEATURE:
<223> OTHER INFORMATION: HCV peptide

<400> SEQUENCE: 131

Ala Ile Lys Trp Glu Tyr Lys Leu Leu Phe Leu Leu
1               5                   10

<210> SEQ ID NO 132
<211> LENGTH: 13
<212> TYPE: PRT
<213> ORGANISM: Artificial Sequence
<220> FEATURE:
<223> OTHER INFORMATION: HCV peptide

<400> SEQUENCE: 132

Ala Ile Lys Trp Glu Tyr Val Lys Leu Leu Phe Leu Leu
1               5                   10

<210> SEQ ID NO 133
<211> LENGTH: 13
<212> TYPE: PRT
<213> ORGANISM: Artificial Sequence
<220> FEATURE:
<223> OTHER INFORMATION: HCV peptide

<400> SEQUENCE: 133

Ala Ile Lys Trp Glu Tyr Val Leu Lys Leu Phe Leu Leu
1               5                   10

<210> SEQ ID NO 134
<211> LENGTH: 13
<212> TYPE: PRT
<213> ORGANISM: Artificial Sequence
<220> FEATURE:
<223> OTHER INFORMATION: HCV peptide

<400> SEQUENCE: 134

Ala Ile Lys Trp Glu Tyr Val Leu Leu Lys Phe Leu Leu
1               5                   10

<210> SEQ ID NO 135
<211> LENGTH: 13
<212> TYPE: PRT
<213> ORGANISM: Artificial Sequence
<220> FEATURE:
<223> OTHER INFORMATION: HCV peptide

<400> SEQUENCE: 135

Ala Ile Lys Trp Glu Tyr Val Leu Leu Leu Lys Leu Leu
1               5                   10

<210> SEQ ID NO 136
<211> LENGTH: 13
<212> TYPE: PRT
```

```
<213> ORGANISM: Artificial Sequence
<220> FEATURE:
<223> OTHER INFORMATION: HCV peptide

<400> SEQUENCE: 136

Ala Ile Lys Trp Glu Tyr Val Leu Leu Leu Phe Lys Leu
1               5                   10

<210> SEQ ID NO 137
<211> LENGTH: 13
<212> TYPE: PRT
<213> ORGANISM: Artificial Sequence
<220> FEATURE:
<223> OTHER INFORMATION: HCV peptide

<400> SEQUENCE: 137

Ala Ile Lys Trp Glu Tyr Val Leu Leu Leu Phe Leu Lys
1               5                   10

<210> SEQ ID NO 138
<211> LENGTH: 13
<212> TYPE: PRT
<213> ORGANISM: Artificial Sequence
<220> FEATURE:
<223> OTHER INFORMATION: HCV peptide

<400> SEQUENCE: 138

Leu Lys Leu Phe Glu Val Tyr Leu Ile Leu Trp Leu Ala
1               5                   10

<210> SEQ ID NO 139
<211> LENGTH: 6
<212> TYPE: PRT
<213> ORGANISM: Artificial Sequence
<220> FEATURE:
<223> OTHER INFORMATION: HCV peptide

<400> SEQUENCE: 139

Ala Ile Lys Trp Glu Tyr
1               5

<210> SEQ ID NO 140
<211> LENGTH: 34
<212> TYPE: DNA
<213> ORGANISM: Artificial Sequence
<220> FEATURE:
<223> OTHER INFORMATION: primer

<400> SEQUENCE: 140
gatcaagctt atgggttgct cctttctat cttc                                    34

<210> SEQ ID NO 141
<211> LENGTH: 40
<212> TYPE: DNA
<213> ORGANISM: Artificial Sequence
<220> FEATURE:
<223> OTHER INFORMATION: primer

<400> SEQUENCE: 141
gatcagatct agtgataatc cggagtcgaa ctcgatagtc                              40
```